US012734214B2

(12) United States Patent
Cherpes et al.

(10) Patent No.: US 12,734,214 B2
(45) Date of Patent: Sep. 15, 2026

(54) COMPOSITIONS AND METHODS FOR INCREASING EPITHELIAL BARRIER FUNCTION

(71) Applicant: The Board of Trustees of the Leland Stanford Junior University, Stanford, CA (US)

(72) Inventors: Thomas Cherpes, Stanford, CA (US); Rodolfo Vicetti Miguel, Stanford, CA (US); Nirk Quispe Calla, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 1196 days.

(21) Appl. No.: 17/767,170

(22) PCT Filed: Oct. 7, 2020

(86) PCT No.: PCT/US2020/054624
§ 371 (c)(1),
(2) Date: Apr. 7, 2022

(87) PCT Pub. No.: WO2021/071979
PCT Pub. Date: Apr. 15, 2021

(65) Prior Publication Data

US 2022/0362330 A1 Nov. 17, 2022

Related U.S. Application Data

(60) Provisional application No. 62/912,541, filed on Oct. 8, 2019.

(51) Int. Cl.

| | |
|---|---|
| ***C07K 14/705*** | (2006.01) |
| ***A61K 31/565*** | (2006.01) |
| ***A61K 31/7088*** | (2006.01) |
| ***A61K 35/68*** | (2006.01) |
| ***A61K 35/74*** | (2015.01) |
| ***A61K 38/17*** | (2006.01) |
| ***A61K 39/00*** | (2006.01) |
| ***A61P 15/02*** | (2006.01) |
| ***A61P 17/02*** | (2006.01) |

(52) U.S. Cl.
CPC .......... *A61K 38/177* (2013.01); *A61K 31/565* (2013.01); *A61K 31/7088* (2013.01); *A61K 35/68* (2013.01); *A61K 35/74* (2013.01); *A61K 39/001196* (2018.08); *A61P 15/02* (2018.01); *A61P 17/02* (2018.01); *C07K 14/705* (2013.01); *C07K 2319/00* (2013.01); *C07K 2319/30* (2013.01)

(58) Field of Classification Search
CPC .............. C07K 14/705; C07K 2319/00; C07K 2319/30; C07K 19/00; A61K 38/177; C12Y 207/10001; C12Y 207/10
See application file for complete search history.

(56) References Cited

U.S. PATENT DOCUMENTS

| | | | | |
|---|---|---|---|---|
| 5,516,658 | A * | 5/1996 | Beckmann | A61P 35/02 435/320.1 |
| 9,714,291 | B2 * | 7/2017 | Niwa | C07K 16/32 |
| 2005/0049194 | A1 | 3/2005 | Frisen et al. | |
| 2005/0147593 | A1 * | 7/2005 | Kinch | A61K 38/1709 424/178.1 |
| 2018/0256598 | A1 | 9/2018 | Mirkin et al. | |

OTHER PUBLICATIONS

Ambrogi et al. Roles of airway and intestinal epithelia in responding to pathogens and maintaining tissue homeostasis. Front Cell Infect Microbiol 14: 1346087, 2024 (25 total pages).*
Genbank Accession No. P01863.1; Jul. 21, 1986.*
Komlosi et al. Cellular and molecular mechanisms of allergic asthma. Mol Aspects Med 85: 100995, 2022 (30 total pages).*
Liu et al. Exogenous ephrin-A3 reverses loss of vaginal epithelial barrier protection in progestin-treated mice. Mucos Immunol 18: 1072-1081, 2025.*
Said-Fernandez et al. Novel immunological and genetic factors associated with vitiligo: A review. Exp Ther Med 21: 312, 2021 (13 total pages).*
Vrana et al. Engineering Functional Epithelium for Regenerative Medicine and In Vitro Organ Models: A Review. Tissue Engin Part B 19(6): 529-543, 2013.*
Wira et al. Innate and adaptive immunity in female genital tract: cellular responses and interactions. Immunol Rev 206: 306-335, 2005.*
International Search Report corresponding to International Application No. PCT/US2020/054624, mailed Feb. 24, 2021 (5 pages).
Written Opinion corresponding to International Application No. PCT/US2020/054624 (8 pages).

* cited by examiner

*Primary Examiner* — Bridget E Bunner
(74) *Attorney, Agent, or Firm* — KDW Firm PLLC

(57) ABSTRACT

Provided herein, inter alia, are compositions for the modulation of epithelium function, the compositions comprising EphrinA3 protein or EphrinA2 protein, fusions thereof, fragments thereof, or oligonucleotides encoding the same. Also provided are methods for modulating epithelium function, the methods comprising administration of compositions provided herein, including embodiments thereof.

15 Claims, 14 Drawing Sheets

Specification includes a Sequence Listing.

COMPOSITIONS AND METHODS FOR INCREASING EPITHELIAL BARRIER FUNCTION

CROSS-REFERENCES TO RELATED APPLICATIONS

This application is a national stage entry, filed under 35 U.S.C. § 371, of International Application No. PCT/US2020/054624, filed on Oct. 7, 2020, which claims the benefit of U.S. Provisional No. 62/912,541 filed Oct. 8, 2019, the entire contents of which is hereby incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under award number R01HD094634 by Eunice Kennedy Shriver National Institute of Child Health and Human Development. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 041243-548001WO_ST25.TXT, created Sep. 7, 2020, 36,864 bytes, machine format IBM-PC, MS-Windows operating system, is hereby incorporated by reference.

BACKGROUND

The epithelial lining of the female genital mucosal barrier is a selectively semipermeable barrier, and the first mucosal surface contacted by sexually transmitted pathogens. The female genital mucosa is the site of adaptive and innate immune responses, and these responses are affected by hormonal changes. Innate immune responses of the mucosal barrier include the complement system, immune system cells, pH, mucus, and the epithelial barrier itself. The epithelial cells express proteins which form desmosomes, tight and adherens junctions, which allow ions and small proteins to pass through the mucosal barrier but reduce permeability to microbes and toxins.

Pathogens such as Human immunodeficiency Virus (HIV-1) and Herpes Simplex Virus (HSV-1 and HSV-2) must penetrate the genital mucosal barrier to establish systemic infection. Probability of male-to-female HIV transmission is about 0.1% per sex act, indicating that 1,000 exposures are needed to acquire HIV. This transmission rate implies while anti-HIV defenses in the female genital tract are moderately effective, factors compromising these defenses will promote HIV susceptibility.

Clinical studies indicate genital epithelial barrier function is decreased in women using exogenous progestins for hormonal contraception and postmenopausal women. This weakening of genital mucosal barrier function may increase susceptibility to sexual transmission of HIV-1 and other sexually transmitted infections.

The genitourinary syndrome of menopause (GSM) affects about half of all menopausal and postmenopausal women and includes symptoms of vaginal burning, dyspareunia, and urinary urgency. These symptoms stem from lower serum estrogen levels that cause reduced tissue elasticity and other genital tract changes. The hypoestrogenemia induced in reproductive age women using the progestin-only contraceptives and the hypoestrogenemia created by loss of ovarian function in menopausal women similarly decrease genital levels of the cell-cell adhesion molecules desmoglein-1 (DSG1) and desmocollin-1 (DSC1) and impairs genital epithelial barrier function. Disclosed herein, inter alia, are solutions to these and other problems in the art.

BRIEF SUMMARY OF THE INVENTION

In an aspect is provided a method for modulating epithelial barrier function in a subject in need thereof. The method includes administering to the subject an effective amount of a composition in a pharmaceutically acceptable carrier including a) a protein at least 90% identical to EphrinA3 protein (SEQ ID NO:1), a fusion thereof, or fragment thereof, or a oligonucleotide encoding the same; or b) a protein at least 90% identical to EphrinA2 protein (SEQ ID NO:2), a fusion thereof, or fragment thereof, or a oligonucleotide encoding the same. In an aspect, the fragment is a peptide at least 90% identical to the sequence of SEQ ID NO:5 or SEQ ID NO:6. In an aspect, the fusion is a peptide at least 90% identical to the sequence of SEQ ID NO:13 or SEQ ID NO:14. In an aspect, the modified protein, fusion thereof, or fragment thereof includes at least one non-natural amino acid residue.

In an aspect is provided a protein at least 90% identical to an EphrinA3 protein including the sequence of SEQ ID NO:1, a fusion thereof, or fragment thereof, or a oligonucleotide encoding the same; or a protein at least 90% identical to an EphrinA2 protein including the sequence of SEQ ID NO:2, a fusion thereof, or fragment thereof, or a oligonucleotide encoding the same.

In an aspect is provided a protein at least 90% identical to an EphrinA3 protein including the sequence of SEQ ID NO:3, a fusion thereof, or fragment thereof, or a oligonucleotide encoding the same; or a protein at least 90% identical to an EphrinA2 protein including the sequence of SEQ ID NO:4, a fusion thereof, or fragment thereof, or a oligonucleotide encoding the same.

In an aspect is provided a pharmaceutical composition including: a) a protein at least 90% identical to an EphrinA3 protein including the sequence of SEQ ID NO:1, a fusion thereof, or fragment thereof, or a oligonucleotide encoding the same; or b) a protein at least 90% identical to an EphrinA2 protein including the sequence of SEQ ID NO:2, a fusion thereof, or fragment thereof, or a oligonucleotide encoding the same.

In an aspect is provided a pharmaceutical composition for modulating epithelial barrier function in a subject. The pharmaceutical composition includes a) a protein at least 90% identical to EphrinA3 protein (SEQ ID NO:1), a fusion thereof, or fragment thereof, or a oligonucleotide encoding the same; or b) a protein at least 90% identical to EphrinA2 protein (SEQ ID NO:2), a fusion thereof, or fragment thereof, or a oligonucleotide encoding the same.

In an aspect is provided composition including: a) a protein at least 90% identical to an EphrinA3 protein comprising the sequence of SEQ ID NO:1, a fusion thereof, or fragment thereof, or a oligonucleotide encoding the same; or b) a protein at least 90% identical to an EphrinA2 protein comprising the sequence of SEQ ID NO:2, a fusion thereof, or fragment thereof, or a oligonucleotide encoding the same.

In an aspect is provided a peptide including an amino acid sequence at least 90% identical to SEQ ID NO:1, SEQ ID NO:2, SEQ ID NO:3, or SEQ ID NO:4.

In an aspect is provided a peptide including an amino acid sequence at least 90% identical to SEQ ID NO:5 or SEQ ID NO:6.

In an aspect is provided a protein including an amino acid sequence at least 90% identical to SEQ ID NO:13 or SEQ ID NO:14.

In an aspect is provided a method of treating or preventing a sexually transmitted disease in a subject in need thereof. The method includes administering to the subject an effective amount of a pharmaceutical composition provided herein including embodiments thereof.

In an aspect is provided a method of treating or preventing vaginal atrophy in a subject in need thereof. The method includes administering to the subject an effective amount of a pharmaceutical composition provided herein including embodiments thereof.

In an aspect is provided a method of treating or preventing a skin disease in a subject in need thereof. The method includes administering to the subject an effective amount of a pharmaceutical composition provided herein including embodiments thereof.

In an aspect is provided a method of treating or preventing an allergic disease in a subject in need thereof. The method includes administering to the subject an effective amount of a pharmaceutical composition provided herein including embodiments thereof.

BRIEF DESCRIPTION OF THE DRAWINGS

FIG. 2A shows Vaginal tissue from untreated mice in estrus or diestrus and mice treated with DMPA or LNG showed that exogenous progestins decrease gene expression levels of the desmosomal cadherins DSG1a (left panel) and DSC1 (right panel). FIG. 2B shows Immunofluorescent staining of vaginal tissue revealed significantly reduced DSG1a protein expression after DMPA or LNG treatment as shown in the bar graph providing between-group comparison of protein quantification.

FIG. 4A is a bar graph showing DMPA-treated mice that also received ivag E cream or systemic E displayed increased gene expression levels of desmosomal cadherins Desmogelin-1$\alpha$ (left panel) and Desmocollin-1 (right panel) compared to mice receiving DMPA alone. FIG. 4B is a Kaplan Meier survival curve showing exogenous E also rescued DMPA-treated mice from lethal ivag infection with $10^4$ pfu of HSV-2.

FIG. 5A is a bar graph showing gene expression for Ephrin A3 (Efna3) relative to pyruvate carboxylase, a housekeeping gene. FIG. 5B shows representative confocal micrograph images of mouse vaginal mucosa immunohistochemically stained to quantify EphrinA3 (EFNA3) in the mouse vaginal mucosa (upper panels) as illustrated in the bar graph (lower panel).

DETAILED DESCRIPTION

Figure 1:
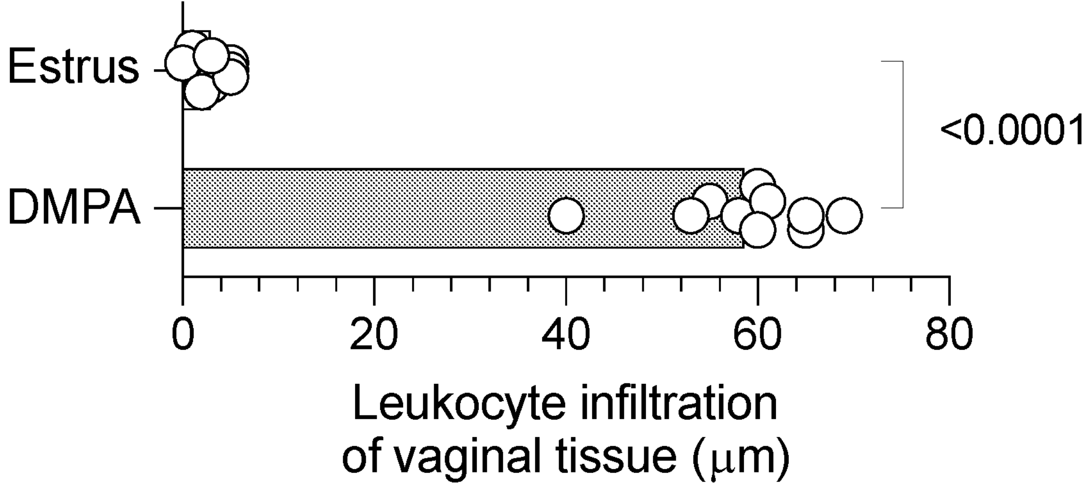
FIG. 1 illustrates DMPA facilitates entry of leukocytes into genital mucosal tissue. Estrus-stage or DMPA-treated mice were administered CFSE-labeled splenocytes intravaginally and euthanized 12 hours later. Relative leukocyte infiltration of vaginal mucosal tissue in estrus-stage vs. DMPA-treated mice was evaluated by confocal microscopy.

After reading this description it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present invention as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

I. Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Unless defined otherwise, technical and scientific terms used herein have the same meaning as commonly understood by a person of ordinary skill in the art. Any methods, devices and materials similar or equivalent to those described herein can be used in the practice of this invention. The following definitions are provided to facilitate understanding of certain terms used frequently herein and are not meant to limit the scope of the present disclosure.

As may be used herein, the terms "nucleic acid," "nucleic acid molecule," "nucleic acid oligomer," "oligonucleotide," "nucleic acid sequence," "nucleic acid fragment" and "oligonucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different oligonucleotides may have different three-dimensional structures, and may perform various functions, known or unknown. Non-limiting examples of oligonucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant oligonucleotide, a branched oligonucleotide, a plasmid, a vector, isolated DNA of a sequence, isolated RNA of a sequence, a nucleic acid probe, and a primer. Oligonucleotides useful in the methods of the disclosure may comprise natural nucleic acid sequences and variants thereof, artificial nucleic acid sequences, or a combination of such sequences.

"Nucleic acid" refers to nucleotides (e.g., deoxyribonucleotides or ribonucleotides) and polymers thereof in either single-, double- or multiple-stranded form, or complements thereof; or nucleosides (e.g., deoxyribonucleosides or ribonucleosides). In embodiments, "nucleic acid" does not include nucleosides. The terms "oligonucleotide," "oligonucleotide," "oligo" or the like refer, in the usual and customary sense, to a linear sequence of nucleotides. The term "nucleoside" refers, in the usual and customary sense, to a glycosylamine including a nucleobase and a five-carbon sugar (ribose or deoxyribose). Non limiting examples, of nucleosides include, cytidine, uridine, adenosine, guanosine, thymidine and inosine. The term "nucleotide" refers, in the usual and customary sense, to a single unit of a oligonucleotide, i.e., a monomer.

Nucleotides can be ribonucleotides, deoxyribonucleotides, or modified versions thereof. Examples of oligonucleotides contemplated herein include single and double stranded DNA, single and double stranded RNA, and hybrid molecules having mixtures of single and double stranded DNA and RNA. Examples of nucleic acid, e.g. oligonucleotides contemplated herein include any types of RNA, e.g. mRNA, shRNA, siRNA, miRNA, and guide RNA and any types of DNA, genomic DNA, plasmid DNA, and minicircle DNA, and any fragments thereof. The term "duplex" in the context of oligonucleotides refers, in the usual and customary sense, to double strandedness. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

In certain embodiments of the present invention, vectors are used to transfer a nucleic acid sequence encoding a protein to a cell. A vector is any molecule used to transfer a nucleic acid sequence to a host cell. In certain cases, an expression vector is utilized. An expression vector is a nucleic acid molecule that is suitable for introduction to and/or propagation in a host cell and contains nucleic acid sequences that direct and/or control the expression of the transferred nucleic acid sequences. Expression includes, but is not limited to, processes such as transcription, translation, and splicing, if introns are present. Expression vectors typically comprise one or more flanking sequences operably linked to a heterologous nucleic acid sequence encoding a protein. Flanking sequences may be homologous (i.e., from the same species and/or strain as the host cell), heterologous (i.e., from a species other than the host cell species or strain), hybrid (i.e., a combination of flanking sequences from more than one source), or synthetic, for example.

Construction of suitable vectors containing the nucleic acid sequences employs standard ligation and restriction techniques, which are well understood in the art (see Maniatis et al., in Molecular Cloning: A Laboratory Manual, Cold Spring Harbor Laboratory, New York (1982)). Isolated plasmids, DNA sequences, or synthesized oligonucleotides are cleaved, tailored, and re-ligated in the form desired.

In embodiments, a nucleic acid molecule encoding Ephrin-A3 protein is utilized. The nucleic acid molecule may comprise or consist of a nucleotide sequence encoding one or more Ephrin-A3 proteins, or fragments (including fragments that code for domains in any order or proteins wherein one or more domains are deleted or disrupted) or derivatives thereof, such as that contained in a DNA insert in an ATCC Deposit. In embodiments, a nucleic acid molecule encoding Ephrin-A2 protein is utilized. The nucleic acid molecule may comprise or consist of a nucleotide sequence encoding one or more Ephrin-A2 proteins, or fragments (including fragments that code for domains in any order or proteins wherein one or more domains are deleted or disrupted) or derivatives thereof, such as that contained in a DNA insert in an ATCC Deposit. The term "nucleic acid sequence" or "nucleic acid molecule" refers to a DNA or RNA sequence. The term encompasses molecules formed from any of the known base analogs of DNA and RNA such as, but not limited- to 4-acetylcytosine, 8-hydroxy-N6-methyladenosine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5' methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine, among others.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "non-natural amino acid side chain" refers to the functional substituent of compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium, allylalanine, 2-aminoisobutryric acid. Non-natural amino acids are non-proteinogenic amino acids that either occur naturally or are chemically synthesized. Non-limiting examples include exo-cis-3-Aminobicyclo[2.2.1]hept-5-ene-2-carboxylic acid hydrochloride, cis-2-Aminocycloheptanecarboxylic acid hydrochloride, cis-6-Amino-3-cyclohexene-1-carboxylic acid hydrochloride, cis-2-Amino-2-methylcyclohexanecarboxylic acid hydrochloride, cis-2-Amino-2-methylcyclopentanecarboxylic acid hydrochloride, 2-(Boc-aminomethyl)benzoic acid, 2-(Boc-amino)octanedioic acid, Boc-4,5-dehydro-Leu-OH (dicyclohexylammonium), Boc-4-(Fmoc-amino)-L-phenylalanine, Boc-β-Homopyr-OH, Boc-(2-indanyl)-Gly-OH, 4-Boc-3-morpholineacetic acid, 4-Boc-3-morpholineacetic acid, Boc-pentafluoro-D-phenylalanine, Boc-pentafluoro-L-phenylalanine, Boc-Phe(2-Br)—OH, Boc-Phe(4-Br)—OH, Boc-D-Phe(4-Br)—OH, Boc-D-Phe(3-Cl)—OH, Boc-Phe (4-NH2)-OH, Boc-Phe(3-NO2)-OH, Boc-Phe(3,5-F2)-OH, 2-(4-Boc-piperazino)-2-(3,4-dimethoxyphenyl)acetic acid purum, 2-(4-Boc-piperazino)-2-(2-fluorophenyl)acetic acid purum, 2-(4-Boc-piperazino)-2-(3-fluorophenyl)acetic acid purum, 2-(4-Boc-piperazino)-2-(4-fluorophenyl)acetic acid purum, 2-(4-Boc-piperazino)-2-(4-methoxyphenyl)acetic acid purum, 2-(4-Boc-piperazino)-2-phenylacetic acid purum, 2-(4-Boc-piperazino)-2-(3-pyridyl)acetic acid purum, 2-(4-Boc-piperazino)-2-[4-(trifluoromethyl)phenyl] acetic acid purum, Boc-β-(2-quinolyl)-Ala-OH, N-Boc-1,2,3,6-tetrahydro-2-pyridinecarboxylic acid, Boc-β-(4-thiazolyl)-Ala-OH, Boc-O-(2-thienyl)-D-Ala-OH, Fmoc-N-(4-Boc-aminobutyl)-Gly-OH, Fmoc-N-(2-Boc-aminoethyl)-Gly-OH, Fmoc-N-(2,4-dimethoxybenzyl)-Gly-OH, Fmoc-(2-indanyl)-Gly-OH, Fmoc-pentafluoro-L-phenylalanine, Fmoc-Pen(Trt)-OH, Fmoc-Phe(2-Br)—OH, Fmoc-Phe(4-Br)—OH, Fmoc-Phe(3,5-F2)-OH, Fmoc-β-(4-thiazolyl)-Ala-OH, Fmoc-β-(2-thienyl)-Ala-OH, 4-(Hydroxymethyl)-D-phenylalanine.

The term "derivative" as used herein in relation to the amino acid sequence means chemical modification of a protein of the invention. Such analogs, for example, have modified R groups (e.g., norleucine) or modified peptide backbones, but retain the same basic chemical structure as a naturally occurring amino acid. Non-limiting examples of such modifications may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine. Additional modifications can include, for example, production of a protein conjugated with polyethylene glycol (PEG), or addition of PEG during chemical synthesis of a protein of the invention.

Other derivatives of the proteins of the present invention include incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those which have molecular shapes similar to phosphate groups.

Derivatives also include proteins modified by glycosylation. These can be made by modifying glycosylation patterns during synthesis and processing in various alternative eukaryotic host expression systems, or during further processing steps. Methods for producing glycosylation modifications include exposing the Ephrin-A3 or Ephrin-A2 protein to glycosylating enzymes derived from cells that normally carry out such processing, such as mammalian glycosylation enzymes. Alternatively, deglycosylation enzymes can be used to remove carbohydrates attached during production in eukaryotic expression systems. Additionally, one can also modify the coding sequence so that glycosylations site(s) are added or glycosylation sites are deleted or disabled. Furthermore, if no glycosylation is desired, the proteins can be produced in a prokaryotic host expression system.

The term "modified," as used herein may refer to the presence of a post-translational modification on a protein. The form "(modified)" term may mean that the proteins being discussed are optionally modified, that is, the proteins under discussion can be modified or unmodified. The term "post-translationally modified" and "modified" may refer to any modification of a natural or non-natural amino acid that occurs to such an amino acid after it has been incorporated into a protein chain. The term encompasses, by way of example only, co-translational in vivo modifications, post-translational in vivo modifications, and post-translational in vitro modifications. As used herein, "co-translational in vivo modification" refers to covalently altering one or more amino acids in a protein after translation has begun but before the protein has been released from the ribosome. That is, the modification may occur during the process of protein translation. The modification occurs in the organism in which the protein is being expressed. A "a post-translational in vivo modification" refers to the covalent modification of a protein following protein biosynthesis in the organism in which the protein is being expressed. A "post-translational in vitro modification" refers to covalent modification of the protein following expression, and outside the organism in which the protein was expressed.

The terms "protein," "peptide" and "polypeptide" are used interchangeably herein to refer to a polymer of amino acid residues. As used herein, the term "peptide" may alternatively be referred to as an "amino acid sequence". Thus, the term "protein" or "peptide" may be used interchangeably with the SEQ ID NO assigned to said peptide. The terms apply to amino acid polymers in which one or more amino acid residue is an artificial chemical mimetic of a corresponding naturally occurring amino acid, as well as to naturally occurring amino acid polymers and non-naturally occurring amino acid polymer.

A "fusion protein," "fusion peptide" or use of the term "fusion" in reference to a protein or peptide refers to a chimeric protein encoding two or more separate protein sequences that are either recombinantly expressed as a single moiety or expressed as separate moieties and linked by covalent attachment. Typically, fusion proteins result from in vitro recombinatory techniques well known in the art. As used herein, "Fc-fusion" refers to a fusion protein including the Fc (i.e. fragment crystallizable region) of an immunoglobulin. The Fc-fusion may include an Fc comprising least 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a naturally occurring Fc. In embodiments, the Fc is a mouse IgG Fc. In embodiments, the Fc is a mouse $IgG_{2A}$ Fc. In embodiments, the Fc is a human IgG Fc. In embodiments, the Fc is a human $IgG_1$ Fc.

In embodiments, the fusion proteins of the present invention may further comprise one or more additional protein domains added to facilitate protein purification, to increase expression of the recombinant protein, or to increase the solubility of the recombinant protein. Such purification/expression/solubility facilitating domains include, but are not limited to, metal chelating peptides such as histidine-tryptophan modules that allow purification on immobilized metals (Porath J (1992) Protein Expr Purif 3-.26328 1), protein A domains that allow purification on immobilized immunoglobulin, and the domain utilized in the FLAGS extension/affinity purification system (Immunex Corp, Seattle, Wash.). The inclusion of a cleavable linker sequence such as Factor Xa or enterokinase (Invitrogen, San Diego, Calif.) between the purification domain and an Ephrin-A3 or Ephrin-A2 protein may be useful to facilitate purification.

Additional fusion expression vectors include pGEX (Pharmaci, a Piscataway, N.J.), pMAL (New England Biolabs, Beverly, Mass.) and pRITS (Pharmacia, Piscataway, N.J.) which fuse glutathione S transferase (GST), maltose B binding protein, or protein A, respectively, to the target recombinant protein. EBV, BKV, and other episomal expression vectors (Invitrogen) can also be used.

Assays for measuring the immunologic activity of any homolog, derivative or variant of any proteins of the present invention are well known in the art.

"Conservatively modified variants" applies to both amino acid and nucleic acid sequences. With respect to particular nucleic acid sequences, conservatively modified variants refer to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded protein. Such nucleic acid variations are "silent variations," which are one species of conservatively modified variations. Every nucleic acid sequence herein which encodes a protein also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a protein is implicit in each described sequence with respect to the expression product, but not with respect to actual probe sequences.

As to amino acid sequences, one of skill will recognize that individual substitutions, deletions or additions to a nucleic acid, peptide, protein, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

Variants and/or derivatives of the proteins of the invention can be prepared by chemical synthesis or by using site-directed mutagenesis (Gillman et al., Gene 8:81 (1979); Roberts et at, Nature 328:731 (1987) or Innis (Ed.), 1990, PCR Protocols: A Guide to Methods and Applications, Academic Press, New York, N.Y.) or the polymerase chain reaction method (PCR; Saiki et al, Science 239:487 (1988)), as exemplified by Daugherty et at (Nucleic Acids Res. 19:2471 (1991)) to modify nucleic acids encoding the Ephrin-A3 or Ephrin-A2 proteins of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

A "label" or a "detectable moiety" is a composition detectable by spectroscopic, photochemical, biochemical, immunochemical, chemical, or other physical means. For example, useful labels include 32P, fluorescent dyes, electron-dense reagents, enzymes (e.g., as commonly used in an ELISA), biotin, digoxigenin, or haptens and proteins or other entities which can be made detectable, e.g., by incorporating a radiolabel into a peptide or antibody specifically reactive with a target peptide. Any method known in the art for conjugating an antibody to the label may be employed, e.g., using methods described in Hermanson, Bioconjugate Techniques 1996, Academic Press, Inc., San Diego.

The term "recombinant" when used with reference, e.g., to a cell, or nucleic acid, protein, or vector, indicates that the cell, nucleic acid, protein or vector has been modified by or is the result of laboratory methods. Thus, for example, recombinant proteins include proteins produced by laboratory methods. Recombinant proteins can include amino acid residues not found within the native (non-recombinant) form of the protein or can be include amino acid residues that have been modified, e.g., labeled.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

In embodiments proteins of the present invention may contain a heterologous signal sequence at its N-terminus. In certain host cells (e.g., mammalian host cells), expression and/or secretion of the fusion protein can be increased through use of a heterologous signal sequence. Signal sequences are typically characterized by a core of hydrophobic amino acids, which are generally cleaved from the mature protein during secretion in one or more cleavage events. Such signal peptides contain processing sites that allow cleavage of the signal sequence from the mature proteins as they pass through the secretory pathway. Thus, the invention pertains to the described proteins having a signal sequence, as well as to proteins from which the signal sequence has been proteolytically cleaved (i.e., the cleavage products).

In order to enhance stability and/or reactivity, the proteins of the present invention can also be modified to incorporate one or more polymorphisms in the amino acid sequence resulting from natural allelic variation. Additionally, D-amino acids, non-natural amino acids or non-amino acid analogues can be substituted or added to produce a modified Ephrin-A3 or Ephrin-A2 protein within the scope of this invention.

The protein can be chemically linked to another molecule. As used herein, the terms "bioconjugate" and "bioconjugate linker" refers to the resulting association between atoms or molecules of "bioconjugate reactive groups" or "bioconjugate reactive moieties". The association can be direct or indirect. For example, a conjugate between a first bioconjugate reactive group (e.g., —NH2, —C(O)OH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g. a first linker of second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). In embodiments, bioconjugates or bioconjugate linkers are formed using bioconjugate chemistry (i.e. the association of two bioconjugate reactive groups) including, but are not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g. a sulfhydryl). In embodiments, the first bioconjugate reactive group (e.g., haloacetyl moiety) is covalently attached to the second bioconjugate reactive group (e.g. a sulfhydryl). In embodiments, the first bioconjugate reactive group (e.g., pyridyl moiety) is covalently attached to the second bioconjugate reactive group (e.g. a sulfhydryl). In embodiments, the first bioconjugate reactive group (e.g., —N-hydroxysuccinimide moiety) is covalently attached to the second bioconjugate reactive group (e.g. an amine). In embodiments, the first bioconjugate reactive group (e.g., maleimide moiety) is covalently attached to the second bioconjugate reactive group (e.g. a sulfhydryl). In embodiments, the first bioconjugate reactive group (e.g., -sulfo-N-hydroxysuccinimide moiety) is covalently attached to the second bioconjugate reactive group (e.g. an amine).

The proteins of the present invention may be produced by expression of a nucleotide sequence coding for same in a suitable expression system.

In addition, or in the alternative, the proteins can be produced using chemical methods to synthesize the desired amino acid sequence, in whole or in part. For example, proteins can be synthesized by solid phase techniques, cleaved from the resin, and purified by preparative high performance liquid chromatography (e.g., Creighton (1983) Proteins Structures And Molecular Principles, WH Freeman and Co, New York N.Y.). The composition of the synthetic proteins may be confirmed by amino acid analysis or sequencing (e.g., the Edman degradation procedure). Additionally, the amino acid sequence of an EphrinA3 or EphrinA2 protein, or any part thereof, may be altered during direct synthesis and/or combined using chemical methods with a sequence from other subunits, or any part thereof, to produce a variant protein.

The terms "identical" or percent sequence "identity," in the context of two or more nucleic acids or protein sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site at ncbi.nlm.nih.gov/BLAST/or the like). Such sequences are then said to be "substantially identical." This definition also refers to, or may be applied to, the compliment of a test sequence. The definition also includes sequences that have deletions and/or additions, as well as those that have substitutions. Employed algorithms can account for gaps and the like.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, WI), or by manual alignment and visual inspection (see, e.g., Current Protocols in Molecular Biology (Ausubel et al., eds. 1995 supplement)).

A preferred example of algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively.

The phrase "selectively (or specifically) hybridizes to" refers to the binding, duplexing, or hybridizing of a molecule only to a particular nucleotide sequence with a higher affinity, e.g., under more stringent conditions, than to other nucleotide sequences (e.g., total cellular or library DNA or RNA).

Nucleic acids may be substantially identical if the proteins which they encode are substantially identical. This occurs, for example, when a copy of a nucleic acid is created using the maximum codon degeneracy permitted by the genetic code. In such cases, the nucleic acids typically hybridize under moderately stringent hybridization conditions.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell. The level of expression of non-coding nucleic acid molecules (e.g., siRNA) may be detected by standard PCR or Northern blot methods well known in the art. See, Sambrook et al., 1989 *Molecular Cloning: A Laboratory Manual,* 18.1-18.88.

The terms "bind" and "bound" refers to the association between atoms or molecules. The association can be direct or indirect. For example, bound atoms or molecules may be direct, e.g., by covalent bond or linker (e.g. a first linker or second linker), or indirect, e.g., by non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like).

The Fc (i.e. fragment crystallizable region) refers to the "base" or "tail" of an immunoglobulin and is typically composed of two heavy chains that contribute two or three constant domains depending on the class of the antibody. For example, in IgG, IgA and IgD antibody isotypes, the Fc region may be composed of two identical protein fragments, derived from the second and third constant domains of the antibody's two heavy chains. IgM and IgE Fc regions may contain three heavy chain constant domains (CH domains 2-4) in each protein chain. In embodiments, the Fc region ensures that each antibody generates an appropriate immune response for a given antigen by binding to specific proteins. In embodiments, the Fc region binds to various cell receptors, such as Fc receptors, and other immune molecules, such as complement proteins.

The term "isolated", when applied to a nucleic acid or protein, denotes that the nucleic acid or protein is essentially free of other cellular components with which it is associated in the natural state. It can be, for example, in a homogeneous state and may be in either a dry or aqueous solution. Purity and homogeneity are typically determined using analytical chemistry techniques such as polyacrylamide gel electrophoresis or high performance liquid chromatography. A protein that is the predominant species present in a preparation is substantially purified.

"Patient," "subject," or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "control" or "standard control" refers to a sample, measurement, or value that serves as a reference, usually a known reference, for comparison to a test sample, measurement, or value. For example, a test sample can be taken from a patient suspected of having a given disease (e.g. HIV, HSV, a viral infection, a bacterial infection, or other disease) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. One of skill will recognize that standard controls can be designed for assessment of any number of parameters (e.g. tissue permeability, RNA levels, protein levels, specific cell types, specific bodily fluids, specific tissues, etc.).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

As used herein, the terms "treat" and "prevent" may refer to any delay in onset, reduction in the frequency or severity of symptoms, amelioration of symptoms, improvement in patient comfort or function (e.g. genital mucosal integrity or barrier function), decrease in severity of the disease state, etc. The effect of treatment can be compared to an individual or pool of individuals not receiving a given treatment, or to the same patient prior to, or after cessation of, treatment. The term "prevent" generally refers to a decrease in the occurrence of a given disease (e.g. HIV, HSV, or other infectious disease) or disease symptoms in a patient. As indicated above, the prevention may be complete (no detectable symptoms) or partial, such that fewer symptoms are observed than would likely occur absent treatment.

As used herein the term "effective amount" is an amount sufficient for a compound to accomplish a stated purpose relative to the absence of the compound (e.g. achieve the effect for which it is administered, treat a disease, or reduce one or more symptoms of a disease or condition). An example of an "effective amount" is an amount sufficient to contribute to the treatment, prevention, or reduction of a symptom or symptoms of a disease, which may be used interchangeably with a "therapeutically effective amount." A "reduction" of a symptom or symptoms (and grammatical equivalents of this phrase) means decreasing of the severity or frequency of the symptom(s), or elimination of the symptom(s). The exact amounts will depend on the purpose of the treatment, and will be ascertainable by one skilled in the art using known techniques.

For the methods provided herein including embodiments thereof, the subject is administered an effective amount of one or more of the compositions (e.g., an EphrinA3 protein or an EphrinA2 protein) provided herein including embodiments thereof. An "effective amount" is an amount sufficient to accomplish a stated purpose (e.g. achieve the effect for which it is administered, prevent a disease (e.g., HSV or HIV), reduce vaginal mucosal permeability, improve mucosal epithelial architecture or barrier function, reduce one or more symptoms of a disease or condition (e.g. loss of ovarian function)). An example of an "effective amount" is an amount sufficient to contribute to the treatment, prevention, or reduction of a symptom or symptoms of a disease (e.g., cancer), which could also be referred to as a "therapeutically effective amount." A "reduction" of a symptom or symptoms (and grammatical equivalents of this phrase) means decreasing of the severity or frequency of the symptom(s), or elimination of the symptom(s). Guidance can be found in the literature for appropriate dosages for given classes of pharmaceutical products. For example, for the given parameter, a therapeutically effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

As is well known in the art, therapeutically effective amounts for use in humans can also be determined from animal models. For example, a dose for humans can be formulated to achieve a dose that has been found to be effective in animals. The dosage in humans can be adjusted by monitoring effectiveness and adjusting the dosage upwards or downwards, as described herein. Adjusting the dose to achieve maximal efficacy in humans based on the methods described herein and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the composition being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the composition. Thereafter, the dosage is increased by small increments until the optimum effect under circumstances is reached. Dosage amounts and intervals can be adjusted individually to provide levels of the administered composition effective for the particular clinical indication being treated. This will provide a therapeutic regimen that is commensurate with the severity of the individual's disease state.

The term "diagnosis" refers to a relative probability that a disease is present in the subject. Similarly, the term "prognosis" refers to a relative probability that a certain future outcome may occur in the subject with respect to a disease state. For example, in the context of the present invention, prognosis can refer to the likelihood that an individual will develop a disease (e.g. HIV infection, HSV infection, or other viral or bacterial infection), or the likely severity of the disease (e.g., duration of disease). The terms are not intended to be absolute, as will be appreciated by any one of skill in the field of medical diagnostics.

"Biological sample" or "sample" refer to materials obtained from or derived from a subject or patient. A biological sample includes sections of tissues (e.g., vaginal tissue or cervical tissue) such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, immune cells, hematopoietic cells, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the tissue type to be evaluated (i.e. genital tissue, etc.), among other factors. Representative biopsy techniques include excisional biopsy, incisional biopsy, needle biopsy, surgical biopsy, and bone marrow biopsy. Biopsy techniques are discussed, for example, in Harrison's Principles of Internal Medicine, Kasper, et al., eds., 16th ed., 2005, Chapter 70, and throughout Part V.

As used herein, the term "administering" means oral administration, administration as a suppository, topical contact, intravenous, parenteral, intraperitoneal, intramuscular, intralesional, intrathecal, intra-cerebro-ventricular, intrapleural, intra-parenchymal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, etc. Administration also includes direct administration, e.g., directly to a site of inflammation. Direct administration may be via guided delivery, e.g., magnetic resonance imaging (MRI)-guided delivery. In embodiments, the administering does not include administration of any active agent other than the recited active agent.

"Co-administer" is meant that a composition described herein is administered at the same time, just prior to, or just after the administration of one or more additional therapies. The compositions provided herein can be administered alone or can be co-administered to the patient. Co-administration is meant to include simultaneous or sequential administration of the compositions individually or in combination (more than one composition). Thus, the preparations can also be combined, when desired, with other active substances.

"Pharmaceutically acceptable excipient" and "pharmaceutically acceptable carrier" refer to a substance that aids the administration of an active agent to and/or absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The proteins and oligonucleotides provided herein, including embodiments thereof, may form part of a pharmaceutical composition. Thus, in embodiments, the composition is a pharmaceutical composition. In embodiments, the pharmaceutical composition includes a pharmaceutically acceptable excipient.

As used herein, the term "pharmaceutically acceptable" is used synonymously with "physiologically acceptable" and "pharmacologically acceptable". A pharmaceutical composition will generally comprise agents for buffering and preservation in storage, and can include buffers and carriers for appropriate delivery, depending on the route of administration.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

The term "pharmaceutically acceptable salts" or "pharmaceutically acceptable carrier" is meant to include salts of the active compounds which are prepared with relatively nontoxic acids or bases, depending on the particular substituents found on the compounds described herein. When compounds of the present application contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present application contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., Journal of Pharmaceutical Science 66:1-19 (1977)). Other pharmaceutically acceptable carriers known to those of skill in the art are suitable for compositions of the present application.

The compositions for administration will commonly comprise an agent as described herein dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the subject's needs.

Solutions of the active compounds as free base or pharmacologically acceptable salt can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations can contain a preservative to prevent the growth of microorganisms.

For administration of a composition to the epithelium, the composition may be supplied as a component of a kit. In embodiments, the kit includes an applicator. In embodiments, the composition may be incorporated in or on the applicator. In some embodiments, the epithelium is the female genital tract. In embodiments, the applicator may be a tampon-like device. Dosage forms include vaginal suppositories, including capsules and tablets. Other devices for administration include but are not limited to a vaginal ring, vaginal pessary, vaginal patch, vaginal pellet or vaginal foam. The device may be coated with or combined with a dosage form of the composition, including a capsule, gel, strip, film, suppository, pellet, cream, or tablet.

For parenteral administration in an aqueous solution, for example, the solution should be suitably buffered and the liquid diluent first rendered isotonic with sufficient saline or glucose. Aqueous solutions, in particular, sterile aqueous media, are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion Sterile injectable solutions can be prepared by incorporating the active compounds or constructs in the required amount in the appropriate solvent followed by filtered sterilization. Generally, dispersions are prepared by incorporating the various sterilized active ingredients into a sterile vehicle which contains the basic dispersion medium. Vacuum-drying and freeze-drying techniques, which yield a powder of the active ingredient plus any additional desired ingredients, can be used to prepare sterile powders for reconstitution of sterile injectable solutions. The preparation of more, or highly, concentrated solutions for direct injection is also contemplated. DMSO can be used as solvent for extremely rapid penetration, delivering high concentrations of the active agents to a small area.

The formulations of compounds can be presented in unit-dose or multi-dose sealed containers, such as ampules and vials. Thus, the composition can be in unit dosage form. In such form the preparation is subdivided into unit doses containing appropriate quantities of the active component. Thus, the compositions can be administered in a variety of unit dosage forms depending upon the method of administration. For example, unit dosage forms suitable for oral administration include, but are not limited to, powder, tablets, pills, capsules and lozenges.

Oral formulations can include excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders. In some embodiments, oral pharmaceutical compositions will comprise an inert diluent or assimilable edible carrier, or they may be enclosed in hard- or soft-shell gelatin capsule, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 75% of the weight of the unit, or preferably between 25-60%. The amount of active compounds in such compositions is such that a suitable dosage can be obtained.

Compositions can be formulated to provide quick, sustained or delayed release after administration by employing procedures known in the art. Certain carriers may be more preferable depending upon, for instance, the route of administration and concentration of composition being administered. Suitable formulations for use in the provided compositions can be found in Remington: The Science and Practice of Pharmacy, 21st Edition, David B. Troy, ed., Lippincott Williams & Wilkins (2005).

The compositions and agents as described herein are useful for both prophylactic and therapeutic treatment. For prophylactic use, a therapeutically effective amount of the agents described herein are administered to a subject prior to or during early exposure (e.g., before initial exposure to viral infection). Therapeutic treatment involves administering to a subject a therapeutically effective amount of the agents described herein after diagnosis or development of disease.

The pharmaceutical compositions disclosed above may further include progestin compositions. In embodiments, the pharmaceutical composition may be applied to the female genital tract. In embodiments, the pharmaceutical composition may include estrogens. In embodiments, the estrogens may be a mixture of conjugated estrogens, which include a mixture of sodium estrone sulfate and sodium equilin sulfate and other components, including sodium sulfate conjugates: 17 $\alpha$-dihydroequilin, 17 $\alpha$-estradiol, and 17 $\beta$-dihydroequilin. A commercial example is PREMARIN® vaginal cream (Pfizer). In embodiments, the formulation may include cetyl esters wax, cetyl alcohol, white wax, glyceryl monostearate, propylene glycol monostearate, methyl stearate, benzyl alcohol, sodium lauryl sulfate, glycerin, or mineral oil. In embodiments, the treatment may include estradiol and other components, including propylene glycol, ceresin, glyceryl caprylocaprate, hypromellose 2208, sodium lauryl sulfate, methylparaben, edetate disodium, or tert-butylhydroquinone. A commercial example is ESTRACE® (estradiol vaginal cream, USP, 0.01%). In embodiments, the treatment may be coated on or placed within a device, which can be inserted within the vaginal cavity. In embodiments, the treatment may include estradiol. In embodiments, the device may be a ring. In embodiments, the ring may include estradiol, silicone polymers and barium sulfate. A commercial example is ESTRING® (Pfizer).

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the protein including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "microbe" or "microbiota" as used herein refers to microorganisms that exist on or within a host organism. The microbes may include bacteria, fungi, protozoa, and viruses. The microbe may be on or within the skin, the respiratory tract, the gastrointestinal tract, or the female genital tract of the host organism. The microbe may normally inhabit the host organism, or be invasive to the host organism. The microbes may be invasive to parts of the host wherein they are not normally present. Microbiota can include beneficial microorgainsms, pathogenic microoranisms, or a combination of beneficial and pathogenic microorganisms. In embodiments, invasion of the microbe (e.g. Human immunodeficiency virus type 1, *Neisseria gonorrhoeae, Chlamydia trachomatis*, Zika virus, or Ebola virus) causes disease.

"Progestin therapy" refers to administration of progestin and/or derivatives thereof. Progestin therapy as used herein includes the administration of progestin and derivatives thereof that bind to the progesterone receptor to mimic effects of progesterone. Progestin may be administered for use as a contraceptive, to regulate the menstrual cycle, for ovarian hormone therapy, or to treat endometriosis. Progestin may be administered to treat symptoms of menopause. Progestin may be administered as a tablet, suspension, gel, jelly, capsule, suppository, in a kit, or in a device. Progestin may be administered as an implant, intrauterine device, patch, vaginal ring, or injectable.

"Peri-menopause" or "perimenopause" is used in accordance with its plain ordinary meaning and refers to the transition into menopause. During peri-menopause changes in production of hormones by the ovaries, including progesterone and estrogen may occur. Ovaries may stop releasing eggs and menstrual cycles may become irregular before stopping. For example, peri-menopause is followed by menopause, wherein a female stops menstruating.

"Menopause" is used in accordance with its plain ordinary meaning and refers to when a female has not had vaginal bleeding for twelve months. Symptoms of menopause may include atrophic vaginitis, vaginal dryness, and painful intercourse.

The term "vaginal atrophy" is used in accordance with its plain ordinary meaning and refers to thinning of the walls of the vagina caused by decreased estrogen levels, and is part of the genitourinary syndrome of menopause. Decreased estrogen levels may also occur during menopause, after menopause, during breastfeeding, after surgical menopause, following chemotherapy, during hormonal therapy, or after hormonal therapy. Symptoms of vaginal atrophy, are part of the genitourinary syndrome of menopause, and include, but are not limited to vaginal wall thinning, tightening and shortening of the vaginal canal, vaginal dryness, vaginal burning, post-intercourse spotting, painful intercourse, pain or burning during urination, increased urinary tract infections, and urinary incontinence.

"Epithelial function" or "epithelial barrier function" are used interchangeably and refer to the epithelium protecting or regulating the underlying tissues. For example, epithelial function may refer to the epithelium protecting the tissue from radiation, desiccation, toxins, invasion by pathogens, allergens, and physical trauma. Epithelial function may refer to the regulation and exchange of chemicals and nutrients between the underlying tissues and the epithelial surface. However, it may rely on a variety of elements, including robust innate immune responses, epithelial barrier function, epithelial cell integrity, as well as the production of mucus. For example, the function may be secretion of hormones into the circulatory system, as well as the secretion of sweat, mucus, enzymes, and other products delivered by ducts. Epithelial barrier function may refer to a protective physical barrier that resists penetration of commensal and pathogenic microorganisms, immune cells, proteins, drugs, toxins, and other unwanted materials. Epithelial barrier function is essential for the maintenance of host homeostasis.

In embodiments, the epithelium is skin. Thus, epithelial barrier function may refer to skin barrier function. Skin barrier function may refer to decreasing permeability of the skin microbiota or molecules. For example, modulating skin barrier function may prevent contact dermatitis, since modulation may prevent penetration of the antigen through the epithelium. Modulating skin barrier function may further reduce psoriasis flares, since it has been shown that psoriasis is caused in part by a defect in skin barrier function In embodiments, the epithelium is a mucous membrane. Mucous membranes line the digestive, respiratory, and reproductive tracts and are the primary barrier between the external world and the interior of the body.

In embodiments, epithelial barrier function is gastrointestinal tract barrier function. Gastrointestinal tract function maintains host homeostasis by regulating nutrient absorption and/or preventing the invasion of pathogenic microbiota, allergens, or toxins in the host. Thus, epithelial barrier function may refer to preventing diseases including eosinophilic esophagitis. Eosinophilic esophagitis refers to a disease in which white blood cells build up on the epithelium of the esophagus. This buildup, which may be a reaction to bacteria, foods, allergens or acid reflux, can inflame or injure the esophageal tissue. Thus, epithelial barrier function refers to preventing or decreasing risk of diseases including eosinophilic esophagitis.

"Female genital mucosal barrier", "female genital barrier", or "genital mucosal barrier" are used interchangeably and refer to protective properties and responses of the vaginal and ectocervical mucosa against toxins and pathogens. Genital mucosal barrier may refer to the epithelial lining of the female reproductive tract that forms a selectively permeable barrier to molecules. Protective properties include the epithelium, pH, mucus, immune system cells, complement system, and the immune system. Protective properties may include physicochemical properties. For example, cells of the genital epithelium are held together by proteins, which decrease its permeability to microbiota (e.g.

HIV or RSV). In another example, the aqueous portion of the vaginal mucosa includes antimicrobial peptides, which form a protective barrier. The female genital mucosal barrier may allow transcellular and paracellular transport of molecules while preventing passage of pathogenic microbes and toxins. Expression of cell-cell adhesion molecules, including desmosomal cadherins in genital epithelial cells may increase barrier function.

"Female genital barrier function" or "mucosal barrier function" or "genital mucosal barrier function" are used interchangeably and refer to the ability of said barrier to resist penetration of toxins and/or pathogens (i.e. HIV or HSV). For example, increasing female genital barrier function may refer to decreasing epithelial permeability to viruses (e.g. HIV).

"Modulating female genital permeability" as used herein refers to affecting the ability of molecules and cells to penetrate the genital mucosal epithelial barrier, and particularly to decreasing the ability of molecules (i.e. drugs and toxins) and microbiota (i.e. viruses, bacteria, fungi, and protozoa) to penetrate the genital mucosal epithelial barrier. Modulation may include administration of EphrinA2 or EphrinA3, or fusion proteins including fragments of EphrinA2 or EphrinA3, fragments of EphrinA2 or EphrinA3, or derived peptides of EphrinA2 or EphrinA3. Modulating female genital mucosal permeability may include increasing expression of desmosomal cadherins desmoglein-1 (DSG1) and/or desmocollin-1 (DSC1), accompanied by epithelial cell proliferation and differentiation, which can lead to increased epithelial thickness, integrity and barrier function. DSC1 and/or DSC1 expression, and/or genital epithelial integrity and barrier function may be increased by administration of EphrinA2 or EphrinA3, fusion proteins thereof, fragments thereof, or derived peptides thereof. Modulation may further include targeting one or more of ABCA12, DSC1, DSG1, EFNA3, FOXA2, KLK7, KRT16, FAS, PPL, or SCEL. Modulation may include administration or targeting of an upstream regulator of ABCA12, DSC1, DSG1, EFNA3, FOXA2, KLK7, KRT16, FAS, PPL, or SCEL (i.e. EphrinA3 or ROCK2). Modulation of female genital permeability may include increased expression of cell-cell adhesion molecules and formation of intercellular adhesion complexes in the genital mucosal epithelium. Increasing intercellular adhesion complexes may result in decreased entry of the vaginal microbiota into mucosal tissue. Modulating female genital permeability may also include reducing penetration of small molecules, toxins and proteins, Modulating female genital permeability may further include reducing inflammation in female genital tissue. Modulating female genital permeability may be measured by decreased sexual transmission of HIV or other sexually transmitted infections. Modulating female genital permeability may be measured by increased expression of one or more of ABCA12, DSC1, DSG1, EFNA3, FOXA2, KLK7, KRT16, FAS, PPL, or SCEL.

"Modulating vaginal atrophy", whose presence contributes to the clinical presentation of women suffering from the genitourinary syndrome of menopause, as used herein refers to improving the epithelial architecture or barrier function of the vaginal mucosal epithelial barrier in menopausal or postmenopausal women. Modulating vaginal atrophy may include administrating EphrinA2 or EphrinA3, fusion proteins thereof, fragments thereof, or derived peptides thereof. Modulating vaginal atrophy may include decreasing symptoms or treating symptoms of vaginal wall thinning. Modulation may include increasing expression of DSG1, DSC1, and epithelial cell proliferation and differentiation, which can lead to increased epithelial thickness, integrity and barrier function. DSC1 and/or DSC1 expression, and/or genital epithelial integrity and barrier function may be increased by administration of EphrinA2 or EphrinA3, or fusion proteins including fragments of the proteins, fragments of the proteins, or derived peptides of the proteins. Modulation may further include targeting one or more of ABCA12, DSC1, DSG1, EFNA3, FOXA2, KLK7, KRT16, FAS, PPL, or SCEL. Modulation may include administration or targeting of an upstream regulator of ABCA12, DSC1, DSG1, EFNA3, FOXA2, KLK7, KRT16, FAS, PPL, or SCEL (i.e. EphrinA3 or ROCK2). Modulating female genital permeability may be measured by increased expression of one or more of ABCA12, DSC1, DSG1, EFNA3, FOXA2, KLK7, KRT16, FAS, PPL, or SCEL. Together, the changes detailed above that can be induced by administration of EphrinA2 or EphrinA3, or fusion proteins including fragments of the proteins, fragments of the proteins, or derived peptides of the proteins, and lead to resolution of symptoms associated with the genitourinary syndrome of menopause, such as dyspareunia and increased susceptibility to urinary tract infection.

Female genital structures include but are not limited to the vulva, vagina, urethra, ectocervix, endocervix, and endometrium. "Vulva" is used in accordance with its plain ordinary meaning and refers to external genital structures and tissues, and includes the mons pubis, pudendal cleft, labia majora, labia minora, Bartholin's glands, clitoris, and vaginal opening. "Vagina" is used in accordance with its plain ordinary meaning and refers to the canal comprising fibrous and muscular tissue leading from the outside of the body to the cervix of the uterus or womb. "Urethra" is used in accordance with its plain ordinary meaning and refers to the tube that connects the urinary bladder to the urinary meatus for the removal of urine from the body. In human females, the urethra connects to the urinary meatus above the vagina. "Cervix" is used in accordance with its plain ordinary meaning and refers to the lower part of the uterus in the human female reproductive system. "Ectocervix" is used in accordance with its plain ordinary meaning and refers to the lower part of the cervix, which swells into the top of the vagina, and "endocervix" refers to the inner part of the cervix that forms a canal connecting the vagina to the uterus. "Endometrium" is used in accordance with its plain ordinary meaning and refers to the inner epithelial layer and mucous membrane, of the mammalian uterus.

As used herein, "sexually transmitted disease" or "STD" are interchangeable and are used in accordance with their plain ordinary meaning and refer to infections that are commonly spread by sexual activity. The infections may be caused by microbiota, including bacteria, viruses, and/or parasites, which are transmitted through sexual activity. Bacterial STDs include *Chlamydia*, gonorrhea, and syphilis. Viral STDs include genital herpes, HIV/AIDS, and genital warts. Parasitic STDs include trichomoniasis. Because STDs are commonly transmitted through the mucous epithelial membranes of the penis, vulva, rectum, urinary tract, mouth, throat, respiratory tract and eyes, improving mucosal epithelial barrier function may decrease risk of STD infection.

As used herein, "allergic diseases" or "allergies" are interchangeable and are used in accordance with their plain ordinary meaning and refer to conditions causes by hypersensitivity of the immune system to typically non-pathogenic or harmless substances. Allergic diseases may be caused by exposure of the skin to irritants and allergens, including microbiota such as bacteria. Allergic diseases may result from the inability of skin to provide protection from said irritants and allergens. The diseases include hives, contact dermatitis, hay fever, food allergies, atopic dermatitis, allergic asthma, and anaphylaxis. Atopic dermatitis, for example, is characterized by one or more of dry skin, red or brown skin patches, raised bumps, raw or sensitive skin, itchy skin, scaly skin, skin infections, asthma, hay fever and sleep problems.

Allergic diseases are a group of immune-mediated disorders mainly caused by an immunological reaction to an innocuous environmental antigen (i.e. an allergen). Based on the site of contact with the allergen, different clinical manifestations may develop in the respiratory tract, integument, or gastrointestinal tract. For example, allergic asthma is an allergic disease generated by allergen contact in the respiratory tract.

As used herein, "skin disease" is used in accordance with its plain ordinary meaning and refers to conditions that affect the skin or show symptoms on the skin. In some instances, an allergy may also be a skin disease. Skin diseases include lupus, psoriasis, eczema, vitiligo, hives, warts, fungal nail infections, cold sores, candidiasis, or cellulitis.

A "EphrinA3" or "EphrinA3 protein" as referred to herein includes any of the recombinant or naturally occurring forms of EphrinA3, or variants or homologs thereof that maintain EphrinA3 activity (e.g. within at least 50%, 80%, 90%, 95%, 96%, 97%, 98%, 99% or 100% activity compared to EphrinA3). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EphrinA3 protein. In embodiments, the EphrinA3 protein is substantially identical to the protein identified by the NCBI reference number GI: 117935036 or a variant or homolog having substantial identity thereto. In embodiments, the EphrinA3 protein is substantially identical to the protein identified by the NCBI reference number GI: 111494020 or a variant or homolog having substantial identity thereto. In embodiments, the EphrinA3 protein is substantially identical to the protein identified by the NCBI reference number GI: 17389357 or a variant or homolog having substantial identity thereto. In embodiments, the EphrinA3 protein is substantially identical to the protein identified by the NCBI reference number GI: 1706671 or a variant or homolog having substantial identity thereto. In embodiments, the EphrinA3 protein has the sequence of SEQ ID NO:1.

In embodiments, the EphrinA3 protein has at least 85%, 86%, 87%, 88%, 89%, 90%, 91%, 92%, 93%, 94%, 95%, 96%, 97%, 98%, 99%, or 100% sequence identity across the whole sequence or a portion of the sequence of SEQ ID NO: 1. In embodiments, the EphrinA3 protein has 85-86%, 86-87%, 87-88%, 88-89%, 89-90%, 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:1.

In embodiments, the EphrinA3 protein has at least 85%, 86%, 87%, 88%, 89%, 90%, 91%, 92%, 93%, 94%, 95%, 96%, 97%, 98%, 99%, or 100% sequence identity across the whole sequence or a portion of the sequence of SEQ ID NO:3. In embodiments, the EphrinA3 protein has 85-86%, 86-87%, 87-88%, 88-89%, 89-90%, 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:3.

A "EphrinA2" or "EphrinA2 protein" as referred to herein includes any of the recombinant or naturally occurring forms of EphrinA2, or variants or homologs thereof that maintain EphrinA2 activity (e.g. within at least 50%, 80%, 90%, 95%, 96%, 97%, 98%, 99% or 100% activity compared to EphrinA2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EphrinA2 protein. In embodiments, the EphrinA2 protein is substantially identical to the protein identified by the NCBI reference number GI: 1706676 or a variant or homolog having substantial identity thereto. In embodiments, the EphrinA2 protein is substantially identical to the protein identified by the NCBI reference number GI: 262118440 or a variant or homolog having substantial identity thereto. In embodiments, the EphrinA2 protein is substantially identical to the protein identified by the NCBI reference number GI: 119589923 or a variant or homolog having substantial identity thereto. In embodiments, the EphrinA2 protein is substantially identical to the protein identified by the NCBI reference number GI: 3913573 or a variant or homolog having substantial identity thereto. In embodiments, the EphrinA2 protein has the sequence of SEQ ID NO:2.

In embodiments, the EphrinA2 protein has at least 85%, 86%, 87%, 88%, 89%, 90%, 91%, 92%, 93%, 94%, 95%, 96%, 97%, 98%, 99%, or 100% sequence identity across the whole sequence or a portion of the sequence of SEQ ID NO:2. In embodiments, the EphrinA2 protein has 85-86%, 86-87%, 87-88%, 88-89%, 89-90%, 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:2.

In embodiments, the EphrinA2 protein has at least 85%, 86%, 87%, 88%, 89%, 90%, 91%, 92%, 93%, 94%, 95%, 96%, 97%, 98%, 99%, or 100% sequence identity across the whole sequence or a portion of the sequence of SEQ ID NO:4. In embodiments, the EphrinA2 protein has 85-86%, 86-87%, 87-88%, 88-89%, 89-90%, 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:4.

II. Methods of Use

In an aspect is provided a method for modulating epithelial barrier function in a subject. The method includes administering to the subject an effective amount of a composition in a pharmaceutically acceptable carrier including: a) a protein at least 90% identical to an EphrinA3 protein including the sequence of SEQ ID NO:1, a fusion thereof, or fragment thereof, or a oligonucleotide encoding the same; or b) a protein at least 90% identical to an EphrinA2 protein comprising the sequence of SEQ ID NO:2, a fusion thereof, or fragment thereof, or a oligonucleotide encoding the same.

In an aspect is provided a method for modulating epithelial barrier function in a subject. The method includes administering to the subject an effective amount of a composition in a pharmaceutically acceptable carrier including: a) a protein at least 90% identical to an EphrinA3 protein including the sequence of SEQ ID NO:3, a fusion thereof, or fragment thereof, or a oligonucleotide encoding the same; or b) a protein at least 90% identical to an EphrinA2 protein comprising the sequence of SEQ ID NO:4, a fusion thereof, or fragment thereof, or a oligonucleotide encoding the same.

In an aspect is provided a method for modulating epithelial barrier function in a subject in need thereof. The method includes administering to the subject an effective amount of:

a) a protein including an amino acid sequence at least 90% identical to SEQ ID NO:1, a fusion thereof, or fragment thereof, or an oligonucleotide encoding the same; or b) a protein including an amino acid sequence at least 90% identical to SEQ ID NO:2, a fusion thereof, or fragment thereof, or an oligonucleotide encoding the same.

In an aspect is provided a method for modulating epithelial barrier function in a subject in need thereof. The method includes administering to the subject an effective amount of: a) a protein including an amino acid sequence at least 90% identical to SEQ ID NO:3, a fusion thereof, or fragment thereof, or an oligonucleotide encoding the same; or b) a protein including an amino acid sequence at least 90% identical to SEQ ID NO:4, a fusion thereof, or fragment thereof, or an oligonucleotide encoding the same.

In embodiments, the protein is at least 90% identical to the EphrinA3 protein including the sequence of SEQ ID NO:1. In embodiments, the EphrinA3 protein has at least 91%, 92%, 93%, 94%, 95%, 96%, 97%, 98%, 99%, or 100% sequence identity across the whole sequence or a portion of the sequence of SEQ ID NO:1. In embodiments, the EphrinA3 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:1.

In embodiments, the EphrinA3 protein has a sequence identity of at least 90% to SEQ ID NO:1. In embodiments, the EphrinA3 protein has a sequence identity of at least 91% to SEQ ID NO:1. In embodiments, the EphrinA3 protein has a sequence identity of at least 92% to SEQ ID NO:1. In embodiments, the EphrinA3 protein has sequence identity of at least 93% to SEQ ID NO:1. In embodiments, the EphrinA3 protein has a sequence identity of at least 94% to SEQ ID NO:1. In embodiments, the EphrinA3 protein has a sequence identity of at least 95% to SEQ ID NO:1. In embodiments, the EphrinA3 protein has a sequence identity of at least 96% to SEQ ID NO:1. In embodiments, the EphrinA3 protein has a sequence identity of at least 97% to SEQ ID NO:1. In embodiments, the EphrinA3 protein has a sequence identity of at least 98% to SEQ ID NO:1. In embodiments, the EphrinA3 protein has a sequence identity of at least 99% to SEQ ID NO:1. In embodiments, the EphrinA3 protein is the sequence of SEQ ID NO:1.

In embodiments, the protein is at least 90% identical to the EphrinA3 protein including the sequence of SEQ ID NO:3. In embodiments, the EphrinA3 protein has at least 91%, 92%, 93%, 94%, 95%, 96%, 97%, 98%, 99%, or 100% sequence identity across the whole sequence or a portion of the sequence of SEQ ID NO:3. In embodiments, the EphrinA3 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:3.

In embodiments, the EphrinA3 protein has a sequence identity of at least 90% to SEQ ID NO:3. In embodiments, the EphrinA3 protein has a sequence identity of at least 91% to SEQ ID NO: 3. In embodiments, the EphrinA3 protein has a sequence identity of at least 92% to SEQ ID NO:3. In embodiments, the EphrinA3 protein has sequence identity of at least 93% to SEQ ID NO:3. In embodiments, the EphrinA3 protein has a sequence identity of at least 94% to SEQ ID NO:3. In embodiments, the EphrinA3 protein has a sequence identity of at least 95% to SEQ ID NO:3. In embodiments, the EphrinA3 protein has a sequence identity of at least 96% to SEQ ID NO:3. In embodiments, the EphrinA3 protein has a sequence identity of at least 97% to SEQ ID NO:3. In embodiments, the EphrinA3 protein has a sequence identity of at least 98% to SEQ ID NO:3. In embodiments, the EphrinA3 protein has a sequence identity of at least 99% to SEQ ID NO:3. In embodiments, the EphrinA3 protein is the sequence of SEQ ID NO:3.

In embodiments, the fusion protein includes a protein at least 90% identical to the EphrinA3 protein including the sequence of SEQ ID NO:1. In embodiments, the fusion protein includes a protein at least 90% identical to the EphrinA3 protein including the sequence of SEQ ID NO:3.

In embodiments, the fusion protein is an Fc-fusion. In embodiments, the Fc-fusion is at least 90% identical to the sequence of SEQ ID NO 13. In embodiments, the Fc-fusion has at least 91%, 92%, 93%, 94%, 95%, 96%, 97%, 98%, 99%, or 100% sequence identity across the whole sequence or a portion of the sequence of SEQ ID NO:13. In embodiments, the Fc-fusion has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:13.

In embodiments, the Fc-fusion has a sequence identity of at least 90% to SEQ ID NO:13. In embodiments, the Fc-fusion has a sequence identity of at least 91% to SEQ ID NO:13. In embodiments, the Fc-fusion has a sequence identity of at least 92% to SEQ ID NO:13. In embodiments, the Fc-fusion has sequence identity of at least 93% to SEQ ID NO:13. In embodiments, the Fc-fusion has a sequence identity of at least 94% to SEQ ID NO:13. In embodiments, the Fc-fusion has a sequence identity of at least 95% to SEQ ID NO:13. In embodiments, the Fc-fusion has a sequence identity of at least 96% to SEQ ID NO:13. In embodiments, the Fc-fusion has a sequence identity of at least 97% to SEQ ID NO:13. In embodiments, the Fc-fusion has a sequence identity of at least 98% to SEQ ID NO:13. In embodiments, the Fc-fusion has a sequence identity of at least 99% to SEQ ID NO:13. In embodiments, the Fc-fusion is the sequence of SEQ ID NO:13.

In embodiments, the fragment of a protein is at least 90% identical to a fragment of the EphrinA3 protein provided herein. In embodiments, the fragment of a protein is at least 90% identical to a fragment of the EphrinA3 protein having the sequence of SEQ ID NO:1. In embodiments, the fragment of a protein is at least 90% identical to a fragment of the EphrinA3 protein having the sequence of SEQ ID NO:3.

In embodiments, the fragment of the protein is from about 10 amino acids residues in length to about 235 amino acid residues in length. In embodiments, the fragment of the protein is about 35 residues in length to about 235 amino acid residues in length. In embodiments, the fragment of the protein is about 60 residues in length to about 235 amino acid residues in length. In embodiments, the fragment of the protein is about 85 residues in length to about 235 amino acid residues in length. In embodiments, the fragment of the protein is about 110 residues in length to about 235 amino acid residues in length. In embodiments, the fragment of the protein is about 135 residues in length to about 235 amino acid residues in length. In embodiments, the fragment of the protein is about 160 residues in length to about 235 amino acid residues in length. In embodiments, the fragment of the protein is about 185 residues in length to about 235 amino acid residues in length. In embodiments, the fragment of the protein is about 210 residues in length to about 235 amino acid residues in length.

In embodiments, the fragment of the protein is about 35 residues in length to about 235 amino acid residues in length. In embodiments, the fragment of the protein is about 35 residues in length to about 210 amino acid residues in length. In embodiments, the fragment of the protein is about 35 residues in length to about 185 amino acid residues in length. In embodiments, the fragment of the protein is about 35 residues in length to about 160 amino acid residues in length. In embodiments, the fragment of the protein is about 35 residues in length to about 135 amino acid residues in length. In embodiments, the fragment of the protein is about 35 residues in length to about 110 amino acid residues in length. In embodiments, the fragment of the protein is about 35 residues in length to about 85 amino acid residues in length. In embodiments, the fragment of the protein is about 35 residues in length to about 60 amino acid residues in length. In embodiments, the fragment of the protein is about 10, about 35, about 60, about 85, about 110, about 135, about 160, about 185, about 210, or about 235 residues in length.

In embodiments, the oligonucleotide encodes a protein at least 90% identical to the EphrinA3 protein including the sequence of SEQ ID NO:1. In embodiments, the oligonucleotide encodes a protein at least 90% identical to the EphrinA3 protein including the sequence of SEQ ID NO:3. In embodiments, the oligonucleotide comprises an expression vector.

In embodiments, the oligonucleotide includes the sequence of SEQ ID NO:9. In aspects, the oligonucleotide has a sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:9. In aspects, the oligonucleotide has a sequence that has at least 85% sequence identity to SEQ ID NO:9. In aspects, the oligonucleotide has a sequence that has at least 90% sequence identity to SEQ ID NO:19. In aspects, the oligonucleotide has a sequence that has at least 95% sequence identity to SEQ ID NO:9. In aspects, the oligonucleotide has a sequence that has at least 98% sequence identity to SEQ ID NO:9. In embodiments, the oligonucleotide is the sequence of SEQ ID NO:9.

In embodiments, oligonucleotide includes the sequence of SEQ ID NO:11. In aspects, the oligonucleotide has a sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:11. In aspects, the oligonucleotide has a sequence that has at least 85% sequence identity to SEQ ID NO:11. In aspects, the oligonucleotide has a sequence that has at least 90% sequence identity to SEQ ID NO:11. In aspects, the oligonucleotide has a sequence that has at least 95% sequence identity to SEQ ID NO:11. In aspects, the oligonucleotide has a sequence that has at least 98% sequence identity to SEQ ID NO:11. In embodiments, oligonucleotide is the sequence of SEQ ID NO:11.

In embodiments, the protein is at least 90% identical to the EphrinA2 protein including the sequence of SEQ ID NO:2. In embodiments, the EphrinA2 protein has at least 91%, 92%, 93%, 94%, 95%, 96%, 97%, 98%, 99%, or 100% sequence identity across the whole sequence or a portion of the sequence of SEQ ID NO:2. In embodiments, the EphrinA2 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:2.

In embodiments, the EphrinA2 protein has a sequence identity of at least 90% to SEQ ID NO:2. In embodiments, the EphrinA2 protein has a sequence identity of at least 91% to SEQ ID NO:2. In embodiments, the EphrinA2 protein has a sequence identity of at least 92% to SEQ ID NO:2. In embodiments, the EphrinA2 protein has sequence identity of at least 93% to SEQ ID NO:2. In embodiments, the EphrinA2 protein has a sequence identity of at least 94% to SEQ ID NO:2. In embodiments, the EphrinA2 protein has a sequence identity of at least 95% to SEQ ID NO:2. In embodiments, the EphrinA2 protein has a sequence identity of at least 96% to SEQ ID NO:2. In embodiments, the EphrinA2 protein has a sequence identity of at least 97% to SEQ ID NO:2. In embodiments, the EphrinA2 protein has a sequence identity of at least 98% to SEQ ID NO:2. In embodiments, the EphrinA2 protein has a sequence identity of at least 99% to SEQ ID NO:2. In embodiments, the EphrinA2 protein is the sequence of SEQ ID NO:2

In embodiments, the protein is at least 90% identical to the EphrinA2 protein including the sequence of SEQ ID NO:4. In embodiments, the EphrinA2 protein has at least 91%, 92%, 93%, 94%, 95%, 96%, 97%, 98%, 99%, or 100% sequence identity across the whole sequence or a portion of the sequence of SEQ ID NO:4. In embodiments, the EphrinA2 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:4.

In embodiments, the EphrinA2 protein has a sequence identity of at least 90% to SEQ ID NO:4. In embodiments, the EphrinA2 protein has a sequence identity of at least 91% to SEQ ID NO:4. In embodiments, the EphrinA2 protein has a sequence identity of at least 92% to SEQ ID NO:4. In embodiments, the EphrinA2 protein has sequence identity of at least 93% to SEQ ID NO:4. In embodiments, the EphrinA2 protein has a sequence identity of at least 94% to SEQ ID NO:4. In embodiments, the EphrinA2 protein has a sequence identity of at least 95% to SEQ ID NO:4. In embodiments, the EphrinA2 protein has a sequence identity of at least 96% to SEQ ID NO:4. In embodiments, the EphrinA2 protein has a sequence identity of at least 97% to SEQ ID NO:4. In embodiments, the EphrinA2 protein has a sequence identity of at least 98% to SEQ ID NO:4. In embodiments, the EphrinA2 protein has a sequence identity of at least 99% to SEQ ID NO:4. In embodiments, the EphrinA2 protein is the sequence of SEQ ID NO:4.

In embodiments, the fusion protein includes a protein at least 90% identical to the EphrinA2 protein including the sequence of SEQ ID NO:2. In embodiments, the fusion protein includes a protein at least 90% identical to the EphrinA2 protein including the sequence of SEQ ID NO:4.

In embodiments, the fusion is an Fc-fusion. In embodiments, the Fc-fusion is at least 90% identical to the sequence of SEQ ID NO:14. In embodiments, the Fc-fusion has at least 91%, 92%, 93%, 94%, 95%, 96%, 97%, 98%, 99%, or 100% sequence identity across the whole sequence or a portion of the sequence of SEQ ID NO:14. In embodiments, the Fc-fusion has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:14.

In embodiments, the Fc-fusion has a sequence identity of at least 90% to SEQ ID NO:14. In embodiments, the Fc-fusion has a sequence identity of at least 91% to SEQ ID NO:14. In embodiments, the Fc-fusion has a sequence identity of at least 92% to SEQ ID NO:14. In embodiments, the Fc-fusion has sequence identity of at least 93% to SEQ ID NO:14. In embodiments, the Fc-fusion has a sequence identity of at least 94% to SEQ ID NO:14. In embodiments, the Fc-fusion has a sequence identity of at least 95% to SEQ ID NO:14. In embodiments, the Fc-fusion has a sequence identity of at least 96% to SEQ ID NO:14. In embodiments, the Fc-fusion has a sequence identity of at least 97% to SEQ ID NO:14. In embodiments, the Fc-fusion has a sequence identity of at least 98% to SEQ ID NO:14. In embodiments, the Fc-fusion has a sequence identity of at least 99% to SEQ ID NO:14. In embodiments, the Fc-fusion is the sequence of SEQ ID NO:14.

In embodiments, the fragment of a protein is at least 90% identical to a fragment of the EphrinA2 protein provided herein. In embodiments, the fragment of a protein is at least 90% identical to a fragment of the EphrinA2 protein having the sequence of SEQ ID NO:2. In embodiments, the fragment of a protein is at least 90% identical to a fragment of the EphrinA2 protein having the sequence of SEQ ID NO:4.

In embodiments, the fragment of the protein provided herein is from about 10 amino acids residues in length to about 235 amino acid residues in length. In embodiments, the fragment of the protein is about 35 residues in length to about 235 amino acid residues in length.

In embodiments, the fragment of the protein is about 60 residues in length to about 235 amino acid residues in length. In embodiments, the fragment of the protein is about 85 residues in length to about 235 amino acid residues in length. In embodiments, the fragment of the protein is about 110 residues in length to about 235 amino acid residues in length. In embodiments, the fragment of the protein is about 135 residues in length to about 235 amino acid residues in length. In embodiments, the fragment of the protein is about 160 residues in length to about 235 amino acid residues in length. In embodiments, the fragment of the protein is about 185 residues in length to about 235 amino acid residues in length. In embodiments, the fragment of the protein is about 210 residues in length to about 235 amino acid residues in length.

In embodiments, the fragment of the protein is about 35 residues in length to about 235 amino acid residues in length. In embodiments, the fragment of the protein is about 35 residues in length to about 210 amino acid residues in length. In embodiments, the fragment of the protein is about 35 residues in length to about 185 amino acid residues in length. In embodiments, the fragment of the protein is about 35 residues in length to about 160 amino acid residues in length. In embodiments, the fragment of the protein is about 35 residues in length to about 135 amino acid residues in length. In embodiments, the fragment of the protein is about 35 residues in length to about 110 amino acid residues in length. In embodiments, the fragment of the protein is about 35 residues in length to about 85 amino acid residues in length. In embodiments, the fragment of the protein is about 35 residues in length to about 60 amino acid residues in length. In embodiments, the fragment of the protein is about 10, about 35, about 60, about 85, about 110, about 135, about 160, about 185, about 210, or about 235 residues in length.

In embodiments, the fusion protein includes a protein at least 90% identical to the EphrinA2 protein having the sequence of SEQ ID NO:4.

In embodiments, the oligonucleotide encodes a protein at least 90% identical to the EphrinA2 protein having the sequence of SEQ ID NO:2.

In embodiments, the oligonucleotide includes the sequence of SEQ ID NO:10. In aspects, the oligonucleotide has a sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:10. In aspects, the oligonucleotide has a sequence that has at least 85% sequence identity to SEQ ID NO:10. In aspects, the oligonucleotide has a sequence that has at least 90% sequence identity to SEQ ID NO:10. In aspects, the oligonucleotide has a sequence that has at least 95% sequence identity to SEQ ID NO:10. In aspects, the oligonucleotide has a sequence that has at least 98% sequence identity to SEQ ID NO:10. In embodiments, the oligonucleotide is the sequence of SEQ ID NO:10.

In embodiments, the oligonucleotide has the sequence of SEQ ID NO:12. In aspects, the oligonucleotide has a sequence that has at least 50%, 55%, 60%, 65%, 70%, 75%, 80%, 85%, 90%, 91%, 92%, 93%, 94%, 95%, 96%, 97%, 98%, 99% or 100% sequence identity to SEQ ID NO:12. In aspects, the oligonucleotide has a sequence that has at least 85% sequence identity to SEQ ID NO:12. In aspects, the oligonucleotide has a sequence that has at least 90% sequence identity to SEQ ID NO:12. In aspects, the oligonucleotide has a sequence that has at least 95% sequence identity to SEQ ID NO:12. In aspects, the oligonucleotide has a sequence that has at least 98% sequence identity to SEQ ID NO:12. In aspects, the oligonucleotide is the sequence of SEQ ID NO:12.

In embodiments, the protein provided herein, fragment thereof, or fusion thereof includes a post-translational modification. In embodiments, the protein provided herein includes a post-translational modification. In embodiments, the fragment provided herein includes a post-translational modification. In embodiments, the fusion provided herein includes a post-translational modification.

In embodiments, the post-translational modification is a co-translational in vivo modification, a post-translational in vivo modification, or a post-translational in vitro modification. In embodiments, the post-translational modification is a co-translational in vivo modification. In embodiments, the post-translational modification is a post-translational in vivo modification. In embodiments, the post-translational modification is a post-translational in vitro modification.

In embodiments, the protein provided herein, fusion thereof, or fragment thereof includes a bioconjugate. In embodiments, the protein provided herein includes a bioconjugate. In embodiments, the fusion provided herein includes a bioconjugate. In embodiments, the fragment provided herein includes a bioconjugate.

In embodiments, the protein, fusion thereof, or fragment thereof comprises a derivative of the protein, fusion thereof, or fragment thereof. In embodiments, the protein comprises a derivative of the protein. In embodiments, the fusion comprises a derivative of the fusion thereof. In embodiments, the fragment comprises a derivative of the fragment.

In embodiments, the fragment is a peptide comprising the sequence of SEQ ID NO:5 or SEQ ID NO:6. In embodiments, the fragment is a peptide comprising the sequence of SEQ ID NO:5. In embodiments, the fragment is a peptide comprising the sequence of SEQ ID NO:6. In embodiments the peptide comprises at least one non-natural amino acid residue. In embodiments, the non-natural amino acid residue is aminohexanoic acid.

In embodiments, the fragment of the EphrinA3 protein includes a peptide including the sequence of SEQ ID NO:5 or SEQ ID NO:6. In embodiments, the fragment includes a peptide having the sequence of SEQ ID NO:5. In embodiments, the fragment includes a peptide having the sequence of SEQ ID NO:6. In embodiments, the fragment includes a peptide having at least 80% sequence identity to SEQ ID NO:5. In embodiments, the fragment includes a peptide having at least 90% sequence identity to SEQ ID NO:5. In embodiments, the fragment includes a peptide having at least 95% sequence identity to SEQ ID NO:5. In embodiments, the fragment is the sequence of SEQ ID NO:5. In embodiments, the fragment includes a peptide having at least 80% sequence identity to SEQ ID NO:6. In embodiments, the fragment includes a peptide having at least 90% sequence identity to SEQ ID NO:6. In embodiments, the fragment includes a peptide having at least 95% sequence identity to SEQ ID NO:6. In embodiments, the fragment is the sequence of SEQ ID NO:6.

In embodiments, the method further includes administering a progestin. In embodiments, the progestin includes conjugated estrogens. In embodiments, the method does not include administering progestin.

In embodiments, the subject previously received progestin therapy. In embodiments, the subject has not previously received progestin therapy.

In embodiments, the subject is pen-menopausal or post-menopausal. In embodiments, the subject is pen-menopausal. In embodiments, the subject is post-menopausal.

In embodiments, the subject previously received or is receiving chemotherapy. In embodiments, the subject previously received chemotherapy. In embodiments, the subject is receiving chemotherapy.

In embodiments, epithelial barrier function is skin barrier function In embodiments, skin barrier function includes wound healing. In embodiments, epithelial barrier function includes respiratory tract barrier function. In embodiments, epithelial barrier function is gastrointestinal tract barrier function. In embodiments, gastrointestinal tract barrier function includes decreased risk of eosinophilic esophagitis.

In embodiments, skin barrier function includes decreased risk of skin diseases or allergic diseases. In embodiments, skin barrier function includes decreased risk of skin diseases. In embodiments, skin barrier function includes decreased risk of allergic diseases. In embodiments, the skin disease is atopic dermatitis.

In embodiments, modulating epithelial barrier function includes modulating female genital permeability or modulating vaginal atrophy. Vaginal atrophy is a change induced by decreased levels of estrogen in menopausal and post-menopausal women that is an important contributor to the signs and symptoms that is termed the genitourinary syndrome of menopause.

In embodiments, modulating epithelial barrier function includes modulating female genital permeability. In embodiments, modulating epithelial barrier function includes modulating vaginal atrophy. In embodiments, the method for modulating epithelial barrier function includes methods for reducing female genital barrier permeability. In embodiments, the method for modulating epithelial barrier function includes methods for reducing vaginal atrophy. The methods include administering to the subject the compositions described herein, including embodiments thereof.

In embodiments, methods for reducing female genital barrier permeability comprises contacting structures of the female genital tract with an effective amount of a composition in a pharmaceutically acceptable carrier. In embodiments, the structures of the female genital tract include, but are not limited to, the vulva, vagina, urethra, ectocervix and endocervix, or endometrium.

In embodiments, the methods provided herein reduce skin, esophagus, or respiratory tract permeability to microbiota in a subject. In embodiments, the methods reduce skin permeability to microbiota in a subject. In embodiments, the methods reduce esophagus permeability to microbiota in a subject. In embodiments, the methods reduce respiratory tract permeability to microbiota in a subject. In embodiments, the methods include administering to the subject an effective amount of a protein provided herein, a fusion thereof, or fragment thereof, or a oligonucleotide encoding the same in a pharmaceutically acceptable carrier.

In embodiments, methods for modulating epithelial barrier function includes methods for reducing epithelial barrier permeability to microbiota. In embodiments, the microbiota are bacterial, viral, protozoan, or fungi. In embodiments, the microbiota are bacterial. In embodiments, the microbiota are viral. In embodiments, the microbiota are protozoan. In embodiments, the microbiota are fungi.

In embodiments, bacteria include one or more of *Neisseria gonorrhoeae, Chlamydia trachomatis, Mycoplasma hominis, Ureaplasma urealyncum, Treponema pallidum, Gardnerella vaginalis, Haemophilus ducreyi*, or *Klebsiella granulomatis*. In embodiments, the bacteria is *N. gonorrhoeae*. In embodiments, the bacteria is *C. trachomatis*. In embodiments, the bacteria is *M. hominis*. In embodiments, the bacteria is *U. urealyticum*. In embodiments, the bacteria is *T. pallidum*. In embodiments, the bacteria is *G. vaginalis*. In embodiments, the bacteria is *H. ducreyi*. In embodiments, the bacteria is *K. granulomatis*.

In embodiments, the virus includes one or more of human immunodeficiency virus types 1 or 2, herpes simplex virus types 1 or 2, human papillomavirus, hepatitis B virus, hepatitis C virus, molluscum contagiosum virus, human T-cell lymphotropic virus types I or II, human herpes virus type 8, zika virus, or Ebola virus. In embodiments, the virus is human immunodeficiency virus type 1. In embodiments, the virus is human immunodeficiency virus type 2. In embodiments, the virus is herpes simplex virus type 1. In embodiments, the virus is herpes simplex virus type 2. In embodiments, the virus is human papillomavirus. In embodiments, the virus is hepatitis B virus. In embodiments, the virus is hepatitis C virus. In embodiments, the virus is molluscum contagiosum virus. In embodiments, the virus is human T-cell lymphotropic virus type I. In embodiments, the virus is human T-cell lymphotropic virus type II. In embodiments, the virus is human herpes virus type 8. In embodiments, the virus is zika virus. In embodiments, the virus is Ebola virus.

In embodiments, the Protozoa includes one or more of *Trichomonas vaginalis.*

In embodiments, the Fungi includes *Candida albicans.*

For the methods provided herein, including embodiments thereof the effective amount of one or more of the agents (e.g., an EphrinA3 protein or an EphrinA2 protein or a fusion thereof, or fragment thereof, or a oligonucleotide encoding the same) may be used in combination with one or more systemic or locally administered estrogen or estrogen receptor modulator. In embodiments, the estrogen includes PREMARIN™, VAGIFEM™, ESTRACE™, ESTRING™ and FEMRING™. In embodiments, the estrogen includes PREMARIN™. In embodiments, the estrogen includes VAGIFEM™. In embodiments, the estrogen includes ESTRACE™. In embodiments, the estrogen includes ESTRING™. In embodiments, the estrogen FEMRING™. In embodiments, the estrogen receptor modulator includes OSPHENA™.

In an aspect is provided a method of treating or preventing a sexually transmitted disease in a subject in need thereof. The method includes administering to the subject an effective amount of a pharmaceutical composition provided herein including embodiments thereof.

In an aspect is provided a method of treating or preventing vaginal atrophy in a subject in need thereof. The method includes administering to the subject an effective amount of a pharmaceutical composition provided herein including embodiments thereof.

In an aspect is provided a method of treating or preventing a skin disease in a subject in need thereof. The method includes administering to the subject an effective amount of a pharmaceutical composition provided herein including embodiments thereof.

In an aspect is provided a method of treating or preventing an allergic disease in a subject in need thereof. The method includes administering to the subject an effective amount of a pharmaceutical composition provided herein including embodiments thereof.

In an aspect is provided a method of treating or preventing a sexually transmitted disease in a subject in need thereof. The method includes administering to the subject an effective amount of a protein, fragment thereof, fusion thereof, or oligonucleotide encoding the same, as provided herein including embodiments thereof.

In an aspect is provided a method of treating or preventing vaginal atrophy in a subject in need thereof. The method includes administering to the subject an effective amount of a protein, fragment thereof, fusion thereof, or oligonucleotide encoding the same, as provided herein including embodiments thereof.

In an aspect is provided a method of treating or preventing a skin disease in a subject in need thereof. The method includes administering to the subject an effective amount of a pharmaceutical composition provided herein including embodiments thereof. The method includes administering to the subject an effective amount of a protein, fragment thereof, fusion thereof, or oligonucleotide encoding the same, as provided herein including embodiments thereof.

In an aspect is provided a method of treating or preventing an allergic disease in a subject in need thereof. The method includes administering to the subject an effective amount of a pharmaceutical composition provided herein including embodiments thereof. The method includes administering to the subject an effective amount of a protein, fragment thereof, fusion thereof, or oligonucleotide encoding the same, as provided herein including embodiments thereof.

III. Pharmaceutical Compositions

In an aspect is provided a pharmaceutical composition including: a) a protein at least 90% identical to an EphrinA3 protein including the sequence of SEQ ID NO:1, a fusion thereof, or fragment thereof, or a oligonucleotide encoding the same; or b) a protein at least 90% identical to an EphrinA2 protein including the sequence of SEQ ID NO:2, a fusion thereof, or fragment thereof, or a oligonucleotide encoding the same.

In an aspect is provided a pharmaceutical composition including: a) a protein at least 90% identical to an EphrinA3 protein including the sequence of SEQ ID NO:3, a fusion thereof, or fragment thereof, or a oligonucleotide encoding the same; or b) a protein at least 90% identical to an EphrinA2 protein including the sequence of SEQ ID NO:4, a fusion thereof, or fragment thereof, or a oligonucleotide encoding the same, In an aspect is provided a pharmaceutical composition for modulating epithelial barrier function in a subject. The pharmaceutical composition includes a protein at least 90% identical to an EphrinA3 protein including the sequence of SEQ ID NO:1, a fusion thereof, or fragment thereof, or a oligonucleotide encoding the same; or b) a protein at least 90% identical to an EphrinA2 protein including the sequence of SEQ ID NO:2, a fusion thereof, or fragment thereof, or a oligonucleotide encoding the same.

In an aspect is provided a pharmaceutical composition for modulating epithelial barrier function in a subject. The pharmaceutical composition includes a protein at least 90% identical to an EphrinA3 protein including the sequence of SEQ ID NO:3, a fusion thereof, or fragment thereof, or a oligonucleotide encoding the same; or b) a protein at least 90% identical to an EphrinA2 protein including the sequence of SEQ ID NO:4, a fusion thereof, or fragment thereof, or a oligonucleotide encoding the same.

In an aspect is provided a composition including: a protein at least 90% identical to an EphrinA3 protein including the sequence of SEQ ID NO:1, a fusion thereof, or fragment thereof, or a oligonucleotide encoding the same; or b) a protein at least 90% identical to an EphrinA2 protein including the sequence of SEQ ID NO:2, a fusion thereof, or fragment thereof, or a oligonucleotide encoding the same.

In an aspect is provided a composition including: a protein at least 90% identical to an EphrinA3 protein including the sequence of SEQ ID NO:3, a fusion thereof, or fragment thereof, or a oligonucleotide encoding the same; or b) a protein at least 90% identical to an EphrinA2 protein including the sequence of SEQ ID NO:4, a fusion thereof, or fragment thereof, or a oligonucleotide encoding the same.

In embodiments, the protein is at least 90% identical to the EphrinA3 protein including the sequence of SEQ ID NO:1. In embodiments, the EphrinA3 protein has at least 91%, 92%, 93%, 94%, 95%, 96%, 97%, 98%, 99%, or 100% sequence identity across the whole sequence or a portion of the sequence of SEQ ID NO:1. In embodiments, the EphrinA3 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:1.

In embodiments, the protein is at least 90% identical to the EphrinA3 protein including the sequence of SEQ ID NO:3. In embodiments, the EphrinA3 protein has at least 91%, 92%, 93%, 94%, 95%, 96%, 97%, 98%, 99%, or 100% sequence identity across the whole sequence or a portion of the sequence of SEQ ID NO:3. In embodiments, the EphrinA3 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:3.

In embodiments, the fusion protein includes a protein at least 90% identical to the EphrinA3 protein having the sequence of SEQ ID NO:1. In embodiments, the fusion protein includes a protein at least 90% identical to the EphrinA3 protein having the sequence of SEQ ID NO:3.

In embodiments, the fusion protein is the fusion is an Fc-fusion. In embodiments, the Fc-fusion is at least 90% identical to the sequence of SEQ ID NO:13. In embodiments, the Fc-fusion is at least 90% identical to the sequence of SEQ ID NO:13. In embodiments, the Fc-fusion has at least 91%, 92%, 93%, 94%, 95%, 96%, 97%, 98%, 99%, or 100% sequence identity across the whole sequence or a portion of the sequence of SEQ ID NO:13. In embodiments, the Fc-fusion has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:13.

In embodiments, the fragment of a protein is at least 90% identical to a fragment of a EphrinA3 protein. In embodiments, the fragment of the protein is from about 5 amino acids residues in length to about 235 amino acid residues in length.

In embodiments, the oligonucleotide encodes a protein at least 90% identical to EphrinA3 protein having the sequence of SEQ ID NO:1. In embodiments, the oligonucleotide encodes a protein at least 90% identical to EphrinA3 protein having the sequence of SEQ ID NO:3. In embodiments, the oligonucleotide comprises an expression vector.

In embodiments, the protein is at least 90% identical to EphrinA2 protein including the sequence of SEQ ID NO:2. In embodiments, the EphrinA2 protein has at least 91%, 92%, 93%, 94%, 95%, 96%, 97%, 98%, 99%, or 100% sequence identity across the whole sequence or a portion of the sequence of SEQ ID NO:2. In embodiments, the EphrinA2 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:2.

In embodiments, the protein is at least 90% identical to EphrinA2 protein including the sequence of SEQ ID NO:4. In embodiments, the EphrinA2 protein has at least 91%, 92%, 93%, 94%, 95%, 96%, 97%, 98%, 99%, or 100% sequence identity across the whole sequence or a portion of the sequence of SEQ ID NO:4. In embodiments, the EphrinA2 protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:4.

In embodiments, the fusion protein includes a protein at least 90% identical to the EphrinA2 protein including the sequence of SEQ ID NO:2. In embodiments, the fusion protein includes a protein at least 90% identical to the EphrinA2 protein including the sequence of SEQ ID NO:4. In embodiments, the fusion is an Fc-fusion. In embodiments, the Fc-fusion is at least 90% identical to the sequence of SEQ ID NO:14. In embodiments, the Fc-fusion has at least 91%, 92%, 93%, 94%, 95%, 96%, 97%, 98%, 99%, or 100% sequence identity across the whole sequence or a portion of the sequence of SEQ ID NO:14. In embodiments, the Fc-fusion has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:14.

In embodiments, the fragment of a protein is at least 90% identical to a fragment of EphrinA2 protein having the sequence of SEQ ID NO:2. In embodiments, the fusion protein includes a protein at least 90% identical to the EphrinA2 protein having the sequence of SEQ ID NO:4.

In embodiments, the oligonucleotide encodes a protein at least 90% identical to EphrinA2 protein including the sequence of SEQ ID NO:2. In embodiments, the fusion protein includes a protein at least 90% identical to the EphrinA2 protein including the sequence of SEQ ID NO:4.

In embodiments, the fragment is a peptide at least 90% identical to the sequence of SEQ ID NO:5 or SEQ ID NO:6. In embodiments, the fragment is a peptide at least 90% identical to the sequence of SEQ ID NO:5. In embodiments, the fragment is a peptide at least 90% identical to the sequence of SEQ ID NO:6. In embodiments, the fragment is a peptide comprising the sequence of SEQ ID NO:5 or SEQ ID NO:6. In embodiments, the fragment is a peptide comprising the sequence of SEQ ID NO:5. In embodiments, the fragment is a peptide comprising the sequence of SEQ ID NO:6. In embodiments the peptide comprises at least one non-natural amino acid residue. In embodiments, the non-natural amino acid residue is aminohexanoic acid.

In embodiments, the pharmaceutical composition further includes a progestin. In embodiments, the progestin comprises conjugated estrogens.

IV. Compounds

In an aspect is provided a protein at least 90% identical to an EphrinA3 protein including the sequence of SEQ ID NO:1, a fusion thereof, or fragment thereof, or a oligonucleotide encoding the same; or a protein at least 90% identical to an EphrinA2 protein including the sequence of SEQ ID NO:2, a fusion thereof, or fragment thereof, or a oligonucleotide encoding the same.

In an aspect is provided a protein at least 90% identical to an EphrinA3 protein including the sequence of SEQ ID NO:3, a fusion thereof, or fragment thereof, or a oligonucleotide encoding the same; or a protein at least 90% identical to an EphrinA2 protein including the sequence of SEQ ID NO:4, a fusion thereof, or fragment thereof, or a oligonucleotide encoding the same.

In an aspect is provided a peptide including an amino acid sequence at least 90% identical to SEQ ID NO:1, SEQ ID NO:2, SEQ ID NO:3, or SEQ ID NO:4. In an aspect is provided a peptide including an amino acid sequence at least 90% identical to SEQ ID NO:1. In an aspect is provided a peptide including an amino acid sequence at least 90% identical to SEQ ID NO:2. In an aspect is provided a peptide including an amino acid sequence at least 90% identical to SEQ ID NO:3. In an aspect is provided a peptide comprising an amino acid sequence at least 90% identical to SEQ ID NO:4.

In embodiments, the peptide has a sequence identity of at least 90% to SEQ ID NO:1. In embodiments, the peptide has a sequence identity of at least 91% to SEQ ID NO:1. In embodiments, the peptide has a sequence identity of at least 92% to SEQ ID NO:1. In embodiments, the peptide has sequence identity of at least 93% to SEQ ID NO:1. In embodiments, the peptide has a sequence identity of at least 94% to SEQ ID NO:1. In embodiments, the peptide has a sequence identity of at least 95% to SEQ ID NO:1. In embodiments, the peptide has a sequence identity of at least 96% to SEQ ID NO:1. In embodiments, the peptide has a sequence identity of at least 97% to SEQ ID NO:1. In embodiments, the peptide has a sequence identity of at least 98% to SEQ ID NO:1. In embodiments, the peptide has a sequence identity of at least 99% to SEQ ID NO:1. In embodiments, the peptide is the sequence of SEQ ID NO:1.

In embodiments, the peptide has a sequence identity of at least 90% to SEQ ID NO:2. In embodiments, the peptide has a sequence identity of at least 91% to SEQ ID NO:2. In embodiments, the peptide has a sequence identity of at least 92% to SEQ ID NO:2. In embodiments, the peptide has sequence identity of at least 93% to SEQ ID NO:2. In embodiments, the peptide has a sequence identity of at least 94% to SEQ ID NO:2. In embodiments, the peptide has a sequence identity of at least 95% to SEQ ID NO:2. In embodiments, the peptide has a sequence identity of at least 96% to SEQ ID NO:2. In embodiments, the peptide has a sequence identity of at least 97% to SEQ ID NO:2. In embodiments, the peptide has a sequence identity of at least 98% to SEQ ID NO:2. In embodiments, the peptide has a sequence identity of at least 99% to SEQ ID NO:2. In embodiments, the peptide is the sequence of SEQ ID NO:2.

In embodiments, the peptide has a sequence identity of at least 90% to SEQ ID NO:3. In embodiments, the peptide has a sequence identity of at least 91% to SEQ ID NO:3. In embodiments, the peptide has a sequence identity of at least 92% to SEQ ID NO:3. In embodiments, the peptide has sequence identity of at least 93% to SEQ ID NO:3. In embodiments, the peptide has a sequence identity of at least 94% to SEQ ID NO:3. In embodiments, the peptide has a sequence identity of at least 95% to SEQ ID NO:3. In embodiments, the peptide has a sequence identity of at least 96% to SEQ ID NO:3. In embodiments, the peptide has a sequence identity of at least 97% to SEQ ID NO:3. In embodiments, the peptide has a sequence identity of at least 98% to SEQ ID NO:3. In embodiments, the peptide has a sequence identity of at least 99% to SEQ ID NO:3. In embodiments, the peptide is the sequence of SEQ ID NO:3.

In embodiments, the peptide has a sequence identity of at least 90% to SEQ ID NO:4. In embodiments, the peptide has a sequence identity of at least 91% to SEQ ID NO:4. In embodiments, the peptide has a sequence identity of at least 92% to SEQ ID NO:4. In embodiments, the peptide has sequence identity of at least 93% to SEQ ID NO:4. In embodiments, the peptide has a sequence identity of at least 94% to SEQ ID NO:4. In embodiments, the peptide has a sequence identity of at least 95% to SEQ ID NO:4. In embodiments, the peptide has a sequence identity of at least 96% to SEQ ID NO:4. In embodiments, the peptide has a sequence identity of at least 97% to SEQ ID NO:4. In embodiments, the peptide has a sequence identity of at least 98% to SEQ ID NO:4. In embodiments, the peptide has a sequence identity of at least 99% to SEQ ID NO:4. In embodiments, the peptide is the sequence of SEQ ID NO:4.

In an aspect is provided a peptide comprising an amino acid sequence at least 90% identical to SEQ ID NO:5 or SEQ ID NO:6. In embodiments, the peptide has a sequence identity of at least 90% to SEQ ID NO:5. In embodiments, the peptide has a sequence identity of at least 95% to SEQ ID NO:5. In embodiments, the peptide is the sequence of SEQ ID NO:5. In embodiments, the peptide has a sequence identity of at least 90% to SEQ ID NO:6. In embodiments, the peptide has a sequence identity of at least 95% to SEQ ID NO:6. In embodiments, the peptide is the sequence of SEQ ID NO:6.

In an aspect is provided a protein at least 90% identical to the sequence of SEQ ID NO:13. In embodiments, the protein has at least 91%, 92%, 93%, 94%, 95%, 96%, 97%, 98%, 99%, or 100% sequence identity across the whole sequence or a portion of the sequence of SEQ ID NO:13. In embodiments, the protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:13.

In embodiments, the protein has a sequence identity of at least 90% to SEQ ID NO:13. In embodiments, the protein has a sequence identity of at least 91% to SEQ ID NO:13. In embodiments, the protein has a sequence identity of at least 92% to SEQ ID NO:13. In embodiments, the protein has sequence identity of at least 93% to SEQ ID NO:13. In embodiments, the protein has a sequence identity of at least 94% to SEQ ID NO:13. In embodiments, the protein has a sequence identity of at least 95% to SEQ ID NO:13. In embodiments, the protein has a sequence identity of at least 96% to SEQ ID NO:13. In embodiments, the protein has a sequence identity of at least 97% to SEQ ID NO:13. In embodiments, the protein has a sequence identity of at least 98% to SEQ ID NO:13. In embodiments, the protein has a sequence identity of at least 99% to SEQ ID NO:13. In embodiments, the protein is the sequence of SEQ ID NO:13.

In an aspect is provided a protein at least 90% identical to the sequence of SEQ ID NO:14. In embodiments, the protein has at least 91%, 92%, 93%, 94%, 95%, 96%, 97%, 98%, 99%, or 100% sequence identity across the whole sequence or a portion of the sequence of SEQ ID NO:14. In embodiments, the protein has 90-91%, 91-92%, 92-93%, 93-94%, 94-95%, 95-96%, 96-97%, 97-98%, 98-99%, or 99-100% sequence identity across the whole sequence or a portion of the sequence of SEQ ID NO:14.

In embodiments, the protein has a sequence identity of at least 90% to SEQ ID NO:14. In embodiments, the protein has a sequence identity of at least 91% to SEQ ID NO:14. In embodiments, the protein has a sequence identity of at least 92% to SEQ ID NO:14. In embodiments, the protein has sequence identity of at least 93% to SEQ ID NO:14. In embodiments, the protein has a sequence identity of at least 94% to SEQ ID NO:14. In embodiments, the protein has a sequence identity of at least 95% to SEQ ID NO:14. In embodiments, the protein has a sequence identity of at least 96% to SEQ ID NO:14. In embodiments, the protein has a sequence identity of at least 97% to SEQ ID NO:14. In embodiments, the protein has a sequence identity of at least 98% to SEQ ID NO:14. In embodiments, the protein has a sequence identity of at least 99% to SEQ ID NO:14. In embodiments, the protein is the sequence of SEQ ID NO:14.

EMBODIMENTS

Embodiment 1. A method for modulating epithelial barrier function in a subject in need thereof comprising administering to the subject an effective amount of a composition in a pharmaceutically acceptable carrier comprising: a) a protein at least 90% identical to an EphrinA3 protein comprising the sequence of SEQ ID NO:1, a fusion thereof, or fragment thereof, or a oligonucleotide encoding the same; or b) a protein at least 90% identical to an EphrinA2 protein comprising the sequence of SEQ ID NO:2, a fusion thereof, or fragment thereof, or a oligonucleotide encoding the same.

Embodiment 2. The method of embodiment 1, wherein the protein, fusion thereof, or fragment thereof comprises a post-translational modification.

Embodiment 3. The method of embodiment 2, wherein the post-translational modification is a co-translational in vivo modification, a post-translational in vivo modification, or a post-translational in vitro modification.

Embodiment 4. The method of any one of embodiments 1-3 wherein the fragment is a peptide at least 90% identical to the sequence of SEQ ID NO:5 or SEQ ID NO:6.

Embodiment 5. The method of any one of embodiments 1-4, wherein the protein, fusion thereof, or fragment thereof comprises at least one non-natural amino acid residue.

Embodiment 6. The method of any one of embodiments 1-5, wherein the protein, fusion thereof, or fragment thereof comprises a derivative of the protein, fusion thereof, or fragment thereof.

Embodiment 7. The method of any one of embodiments 1-6, wherein the protein, fusion thereof, or fragment thereof comprises a bioconjugate.

Embodiment 8. The method of any one of embodiments 1-7, wherein the fusion is an Fc-fusion.

Embodiment 9. The method of embodiment 8, wherein the Fc-fusion is at least 90% identical to SEQ ID NO:13.

Embodiment 10. The method of embodiment 8, wherein the Fc-fusion is at least 90% identical to SEQ ID NO:14.

Embodiment 11. The method of embodiment 1, wherein the oligonucleotide comprises an expression vector.

Embodiment 12. The method of any one of embodiments 1-11, wherein the epithelial barrier function is modulating female genital barrier permeability or modulating vaginal atrophy.

Embodiment 13. The method of any one of embodiments 1-12, further comprising administering a progestin.

Embodiment 14. The method of embodiment 13, wherein the progestin comprises conjugated estrogens.

Embodiment 15. The method of any one of embodiments 1-12, wherein the method does not include administering a progestin.

Embodiment 16. The method of any one of embodiments 1-14, wherein the subject previously received progestin therapy.

Embodiment 17. The method of any one of embodiments 1-15, wherein the subject has not previously received progestin therapy.

Embodiment 18. The method of any one of embodiments 1-17, wherein the subject is peri-menopausal or post-menopausal.

Embodiment 19. The method of any one of embodiments 1-18, wherein the subject previously received or is receiving chemotherapy.

Embodiment 20. The method of any one of embodiments 1-11, wherein the epithelial barrier function is respiratory tract barrier function.

Embodiment 21. The method of any one of embodiments 1-11, wherein the epithelial barrier function is gastrointestinal tract barrier function.

Embodiment 22. The method of any one of embodiments 1-11, wherein the epithelial barrier function is skin barrier function.

Embodiment 23. The method of embodiment 22, wherein skin barrier function comprises decreased risk of skin diseases or allergic diseases.

Embodiment 24. The method of any one of embodiments 1-22, wherein the epithelial barrier function is decreased penetration by microbiota.

Embodiment 25. The method of embodiment 24, wherein the microbiota are bacterial, viral, protozoan, or fungal.

Embodiment 26. The method of embodiment 24 or 25, wherein the microbiota are bacterial and the bacterial species comprise *Neisseria gonorrhoeae, Chlamydia trachomatis, Mycoplasma hominis, Ureaplasma urealyticum, Treponema pallidum, Gardnerella vaginalis, Haemophilus ducreyi*, or *Klebsiella granulomatis.*

Embodiment 27. The method of embodiment 24 or 25, wherein the microbiota are viral and the viral species comprise human immunodeficiency virus type 1, human immunodeficiency virus type 2, herpes simplex virus type 1, herpes simplex virus type 2, human papillomavirus, hepatitis B virus, hepatitis C virus, molluscum contagiosum virus, human T-cell lymphotropic virus type I, human T-cell lymphotropic virus type II, human herpes virus type 8, Zika virus, or Ebola virus.

Embodiment 28. The method of embodiment 24 or 25, wherein the microbiota are protozoan and the protozoan species comprise *Trichomonas vaginalis.*

Embodiment 29. The method of embodiment 24 or 25, wherein the microbiota are fungal and the fungal species comprise *Candida albicans.*

Embodiment 30. A peptide comprising an amino acid sequence at least 90% identical to SEQ ID NO:1, SEQ ID NO:2, SEQ ID NO:3, or SEQ ID NO:4.

Embodiment 31. A peptide comprising an amino acid sequence at least 90% identical to SEQ ID NO:5 or SEQ ID NO:6.

Embodiment 32. The peptide of embodiment 30 or 31, comprising at least one non-natural amino acid residue.

Embodiment 33. A pharmaceutical composition comprising: a) a protein at least 90% identical to an EphrinA3 protein comprising the sequence of SEQ ID NO:1, a fusion thereof, or fragment thereof, or a oligonucleotide encoding the same; or b) a protein at least 90% identical to an EphrinA2 protein comprising the sequence of SEQ ID NO:2, a fusion thereof, or fragment thereof, or a oligonucleotide encoding the same.

Embodiment 34. The pharmaceutical composition of embodiment 33, wherein the fragment is a peptide at least 90% identical to the sequence of SEQ ID NO:5 or SEQ ID NO:6.

Embodiment 35. The pharmaceutical composition of embodiment 33 or 34, wherein the protein comprises at least one non-natural amino acid residue.

Embodiment 36. The pharmaceutical composition of embodiment 33, wherein the fusion is an Fc-fusion.

Embodiment 37. The pharmaceutical composition of embodiment 36, wherein the Fc-fusion is at least 90% identical to SEQ ID NO:13.

Embodiment 38. The pharmaceutical composition of embodiment 36, wherein the Fc-fusion is at least 90% identical to SEQ ID NO:14.

Embodiment 39. The pharmaceutical composition of embodiment 33, wherein the oligonucleotide comprises an expression vector.

Embodiment 40. The pharmaceutical composition of any one of embodiments 33-39, further comprising a progestin.

Embodiment 41. The pharmaceutical composition of embodiment 40, wherein the progestin comprises conjugated estrogens.

Embodiment 42. A method of treating or preventing a sexually transmitted disease in a subject in need thereof comprising administering to the subject an effective amount an effective amount of the pharmaceutical composition of any one of embodiments 33-41.

Embodiment 43. A method of treating or preventing vaginal atrophy in a subject in need thereof comprising administering to the subject an effective amount an effective amount of the pharmaceutical composition of any one of embodiments 33-41.

Embodiment 44. A method of treating or preventing a skin disease in a subject in need thereof comprising administering to the subject an effective amount an effective amount of the pharmaceutical composition of any one of embodiments 33-39.

Embodiment 45. A method of treating or preventing an allergic disease in a subject in need thereof comprising administering to the subject an effective amount an effective amount of the pharmaceutical composition of any one of embodiments 33-39.

Embodiment 46. A composition comprising: a) a protein at least 90% identical to an EphrinA3 protein comprising the sequence of SEQ ID NO:1, a fusion thereof, or fragment thereof, or a oligonucleotide encoding the same; or b) a protein at least 90% identical to an EphrinA2 protein comprising the sequence of SEQ ID NO:2, a fusion thereof, or fragment thereof, or a oligonucleotide encoding the same.

Embodiment 47. A fusion protein comprising an amino acid sequence at least 90% identical SEQ ID NO:13.

Embodiment 48. A fusion protein comprising an amino acid sequence at least 90% identical SEQ ID NO:14.

Embodiment 49. A peptide comprising an amino acid sequence at least 90% identical SEQ ID NO:5.

Embodiment 50. A peptide comprising an amino acid sequence at least 90% identical SEQ ID NO:6.

EXAMPLES

Example 1: Progestin Treatment Reduces Mucosal Barrier Function in the Female Genital Tract Effects of progestins on genital mucosal barrier permeability were evaluated by intravaginally (ivag) administering 457 Da and 70 KDa-sized fluorescent molecules to mice in estrus or diestrus-stage or after DMPA or LNG treatment. Mice were grouped as follows: untreated in estrus, untreated in diestrus, DMPA treated, or LNG treated. The mice were intravaginally administered a PBS solution containing Lucifer yellow (457 Da) and Texas-Red-conjugated dextran (70 KDa). Animals were euthanized 45 minutes later to assess vaginal tissue penetration of these molecules by confocal microscopy. Confocal images of vaginal tissue show greatest penetration of the 457 Da molecules in DMPA- or LNG-treated mice. These results are consistent with the differential survival of mice after genital HSV-2 infection. Mucosal permeability was increased moderately by diestrus, but dramatically by DMPA or LNG. Conversely, permeability increases were negligible in estrus-stage mice and mice treated with MePRDL or DMPA and RU486. This indicates exogenous progestins increase genital mucosal permeability.

DMPA also promoted leukocyte entry into genital tissue, as fluorescently labeled splenocytes penetrated tissue of DMPA-treated mice, but not mice in estrus (FIG. 1). These findings established progestin mediated increases in mucosal permeability promote both passive entry of low molecular weight molecules and incursion of larger-sized cells that are more reliant on energy-dependent processes.

Figure 2A:
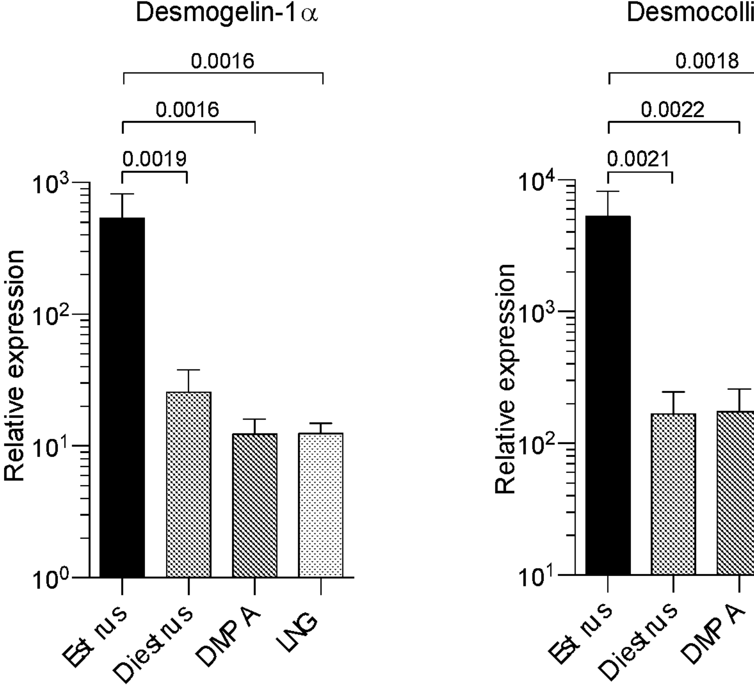
FIG. 2A-B are graphs showing DMPA or LNG treatment of mice reduces desmosomal expression in vaginal epithelial tissue.
Figure 2B:
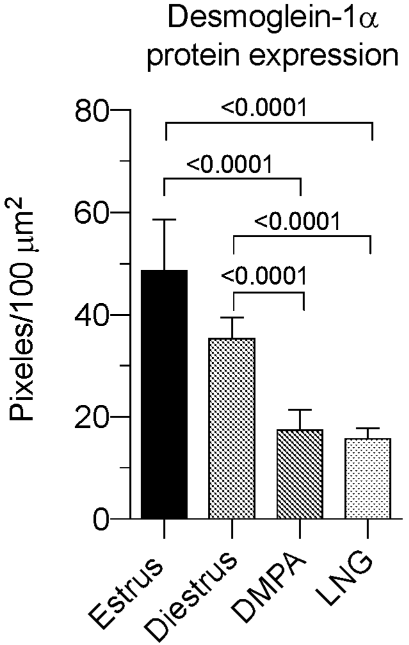

To define progestin-mediated changes in mucosal permeability, vaginal tissue from mice in estrus, diestrus, or after DMPA or LNG treatment was used to measure expression of the desmosomal cadherins desmoglein-1a (DSG1a) and desmocollin-1 (DSC1). These cell-cell adhesion molecules are found in many types of epithelium, including female genital epithelium and have been shown to promote barrier function in the skin and intestine. Compared to mice in estrus, there was significantly less DSG1a and DSC1 gene expression and DSG1 protein levels in vaginal tissue from diestrus-stage and progestin-treated mice (FIG. 2A-B). On the other hand, DMPA and LNG did not alter gene expression of other cell-cell adhesion molecules, including claudin-1, occludin, and tight junction protein 1.

While prior clinical studies identified increased inflammation in the genital tracts of women using DMPA, the underlying mechanism for this effect had been undefined. Because DMPA increased genital mucosal permeability, it was posited DMPA increases inflammation by promoting entry of the vaginal microbiota into mucosal tissue. In support of this hypothesis, more Gram-negative bacteria and higher levels of pro-inflammatory mediators in the mucosa of DMPA-treated vs. estrus-stage mice was observed. Moreover, DMPA treatment of germ-free mice (i.e., mice with no vaginal microbiota) increased permeability but not inflammation, indicating DMPA-induced changes in permeability are not sequelae to DMPA-mediated increases in inflammation. These findings with germ-free mice revealed genital inflammation induced by DMPA occurs downstream of DMPA-mediated compromise of genital mucosal barrier protection.

Figure 3:
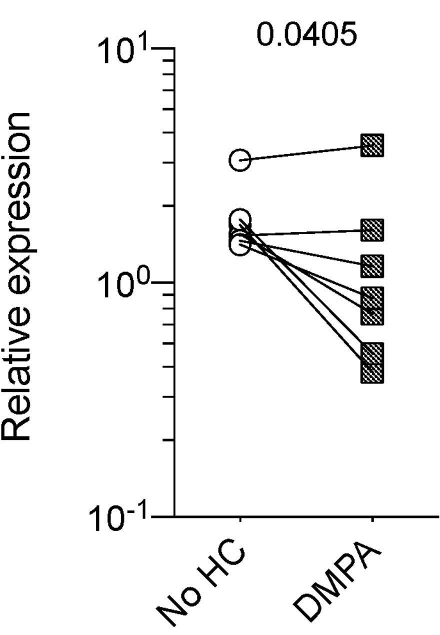
FIG. 3 is a graph showing the effect of DMPA on ectocervical DSG1 gene expression in women. Ectocervical biopsy tissue collected from the same women; before they started (No HC) and 1 month after they initiated DMPA.

To confirm the relevance of the mouse model findings, DMPA-mediated changes in mucosal permeability was explored with ectocervical biopsies from women using no hormonal contraceptive and again 1 month after they initiated DMPA. Compared to the first visit, there was significantly lower DSG1 expression, as shown in FIG. 3, and significantly higher expression of numerous markers of inflammation in the ectocervical tissue obtained women initiated DMPA. There was also identification of a strong positive correlation between serum DMPA levels and genital mucosal permeability. The increased mucosal permeability, and reduced cell-cell adhesion molecule expression, accompanied by increased pro-inflammatory marker expression in the specimens collected after initiating hormonal contraceptive confirm DMPA mediates changes. These results are analogous to those found in DMPA-treated mice.

Figure 4A:
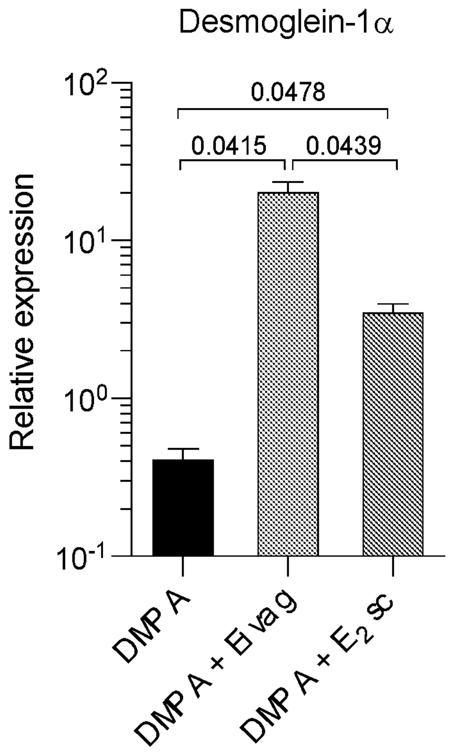
FIG. 4A-B are graphs showing exogenous estrogen (E) promotes DSG1a expression and reduces susceptibility of DMPA-treated mice to ivag HSV-2 infection.
Figure 4A:
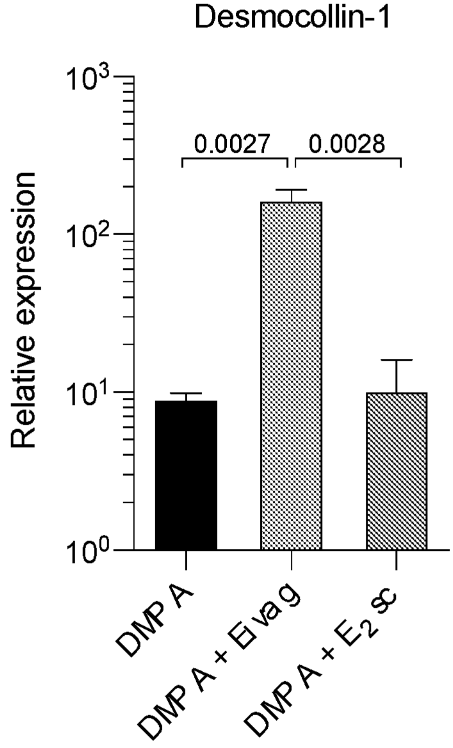
Figure 4B:
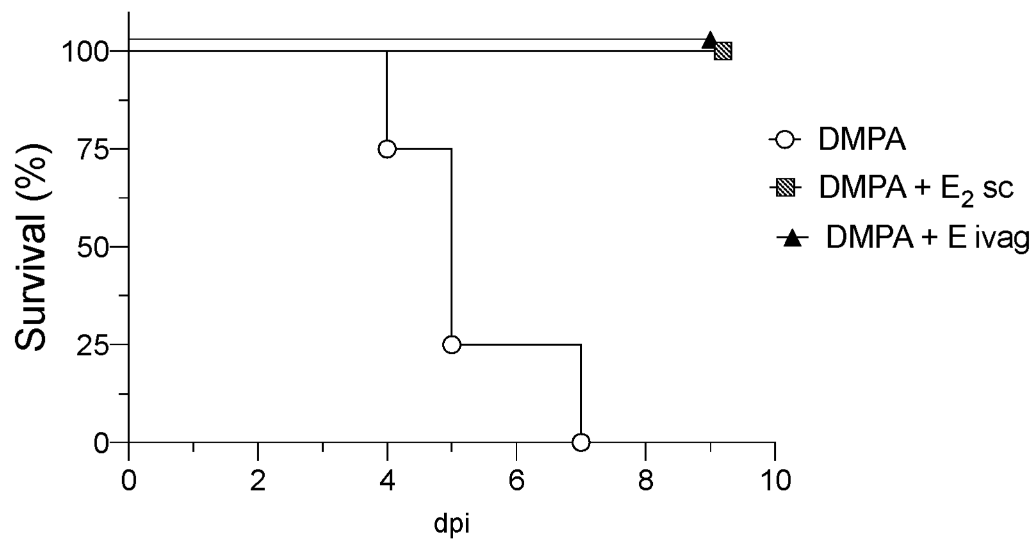

Because mice in estrus (the stage with highest effects of estrogen in genital tissue) displayed more genital DSG1 expression, enhanced mucosal barrier function, and resistance to genital HSV-2 infection, it was hypothesized that mice treated with DMPA and a commercially available vaginal estrogen (E) cream are resistant to genital HSV-2 infection. As posited, there was 100% survival in mice treated with DMPA and E (FIG. 4B). Systemic E administration also protected DMPA-treated mice from HSV-2, indicating protection conferred by the E cream was not an artifact of cream blocking virus access to mucosal surfaces. Exogenous E likewise increased vaginal DSG1a and DSC1 expression and reduced vaginal mucosal permeability (FIG. 4A). Whereas mice in estrus and mice treated with DMPA and E were resistant to HSV-2, vaginal epithelial keratinization was increased only in estrus-stage mice. Thus, while progestin-mediated loss of epithelial keratinization had been proposed as a mechanism by which DMPA promotes susceptibility to genital pathogens, data described herein shows that DMPA-mediated increase in mucosal permeability is the more important risk factor.

Because mice treated with DMPA and E were HSV-2 resistant and DMPA facilitated entry of leukocytes into vaginal tissue, it was posited that exogenous E blocks HIV-1 acquisition in a humanized mouse model of cell-associated HIV transmission. Human PBMC (hPBMCs)-engrafted NSG mice treated with DMPA or DMPA and E cream were ivag inoculated with CFSE-labeled activated hPBMCs. 15 h later, entry of these cells into vaginal tissue was examined by confocal microscopy. Comparison of PBMC incursion showed that activated hPBMCs more readily penetrated the genital mucosa in the mice treated with DMPA. Humanized NSG mice treated as described above were also ivag infected with cell-associated HIV-1 ($10^6$ hPBMCs infected with HIV-1 Ba-L). 10 days later, serum was collected to quantify HIV-1 load via qRT-PCR. As posited, treatment with DMPA and ivag E cream eliminated the increases in genital mucosal permeability and susceptibility to genital HIV-1 infection seen in humanized mice treated with DMPA alone. DMPA-administered mice treated with E cream or the pharmacologically active component of the cream alone (i.e., pure E) also had similar levels of DSG1 expression and reduction in genital mucosal permeability. These results show mice treated with DMPA and E cream were protected from infection with cell-associated HIV-1.

The above results established changes that occur in genital mucosa of women initiating DMPA are recapitulated in DMPA-treated mice, and these that changes include lower expression of the cell-cell adhesion molecule DSG1 and increased genital mucosal permeability. To investigate mechanisms for DMPA-mediated downregulation of DSG1, genome-wide gene expression studies were performed with vaginal tissue from estrus-stage mice (i.e., mice resistant to genital HSV infection) and DMPA-treated mice (i.e., mice highly susceptible to this virus). These studies showed DMPA enriches canonical pathways related to dermatological and inflammatory diseases (Table 1), findings that corroborated results in which DMPA impaired genital mucosal barrier function and increased inflammation. These studies also newly identified DMPA-mediated inhibition of signaling pathways that involve ephrin-A3 (EFNA3) and ROCK2, molecules that are ER-alpha (ESR1) target genes and upstream regulators of DSC1 and DSG1 (Table 1). EFNA molecules are involved in pathways that induce DSG1 expression and regulate epithelial cell responses and formation of intercellular adhesion complexes, and Eph receptors stimulate ROCK2-mediated actinomyosin contractility that increases keratinocyte differentiation via DSG1 upregulation. These gene expression analyses thus identified a potential mechanism by which progestins alter E-regulated expression of EFNA3 and ROCK2 and levels of DSG1. As EFNA3, DSG1, and ROCK2 are basally expressed in human genital epithelium, capacity of this E-regulated pathway to promote genital mucosal integrity in mice may also extend to results seen in the human female genital tract.

TABLE 1

Pathway analysis revealed DMPA-mediated enrichment of canonical pathways associated with dermatological and inflammatory diseases and inhibition of DSG1 expression. Genome-wide gene expression studies using vaginal tissue from estrus-stage and DMPA-treated mice delineate the (left panel) key biological functions and (right panel) upstream regulators affected by DMPA treatment.

Figure 7:
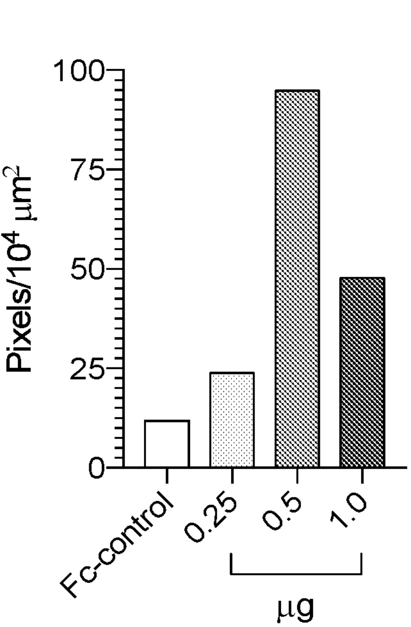
FIG. 7 is a bar graph showing increased levels of DSG1 protein in genital tissue from DMPA-treated mice intravaginally administered select doses of EFNA3. In these studies, mice were intravaginally treated with indicated doses of His-EFNA3 in 10 μL of PBS and euthanized 24 hours later to measure vaginal DSG1 protein levels.
Figure 8:
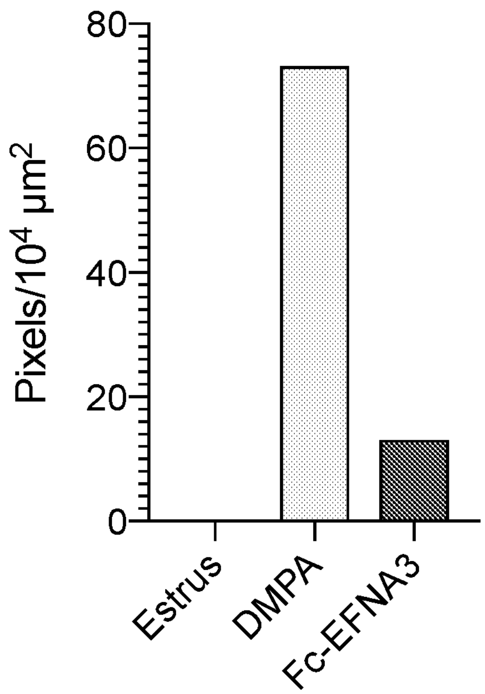
FIG. 8 is a bar graph showing decreased genital mucosal permeability in DMPA-treated mice intravaginally administered one dose of 1.5 ug/30 uL dose of recombinant mouse Fc-EFNA3. These studies compared in vivo vaginal permeability to LMW fluorescent molecules.
Figure 9A:
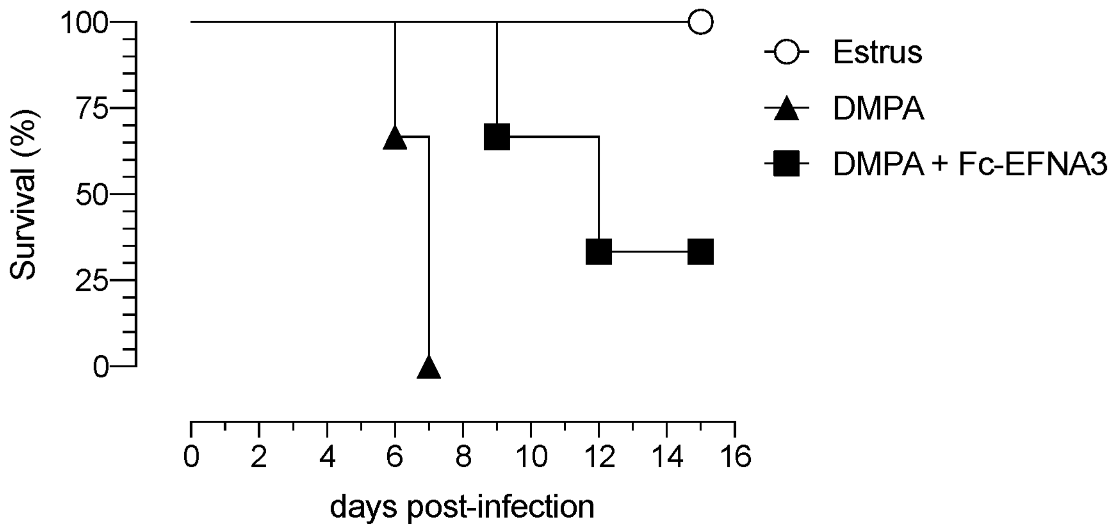
FIG. 9A-B shows EFNA3 treatment improves the survival of DMPA-treated mice. Survival curves depict survival of estrus-stage mice, DMPA-treated mice, and mice treated with DMPA- and Fc-EFNA3- (FIG. 9A) or His-EFNA3- (FIG. 9B) after genital infection with $10^4$ pfu of HSV-2.
Figure 9B:
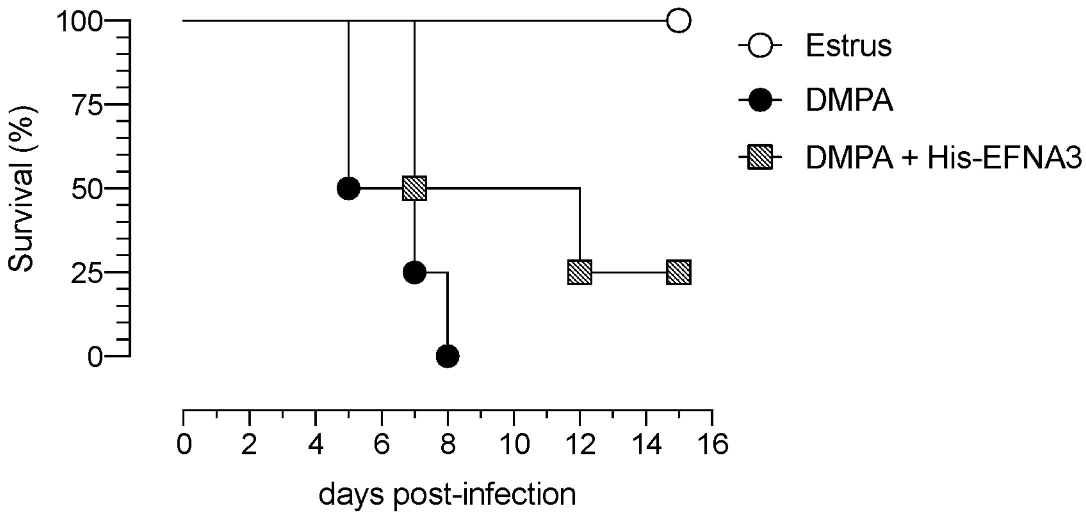
Figure 10A:
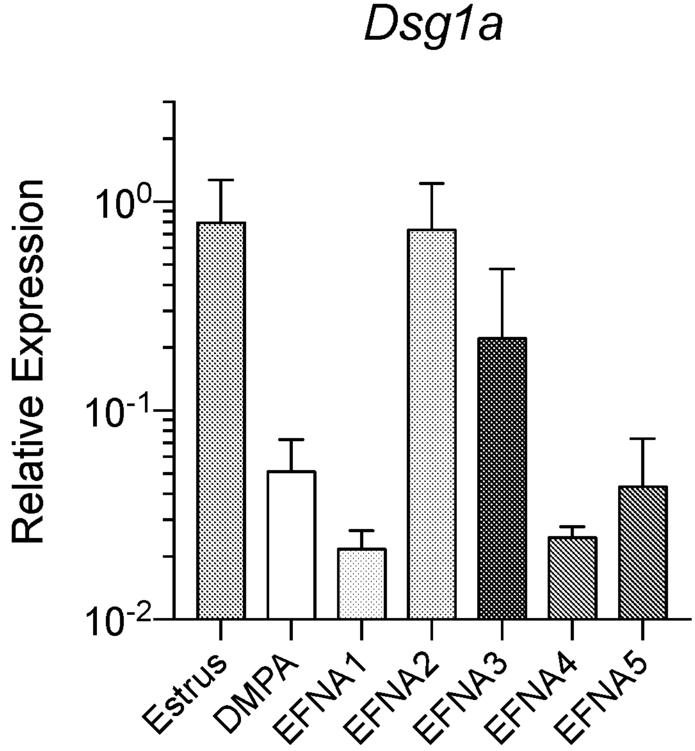
FIG. 10A-B show increased relative expression of Dsg1a as analyzed by RT-PCR (FIG. 10A) and increased levels of DSG1 protein (FIG. 10B) in mice treated with select doses of EFNA2 or EFNA3. Estrus-stage mice, DMPA-treated mice, and DMPA-treated mice intravaginally administered EFNA1, EFNA2, EFNA3, EFNA4, EFNA5 (all His-tagged at a concentration of 1.5 ug/30 uL) were examined. Mice were euthanized 24 h later and vaginas excised for RNA isolation and DSG1 protein level quantification using immunofluorescent staining and confocal microscopy.
Figure 10B:
Figure 10B:
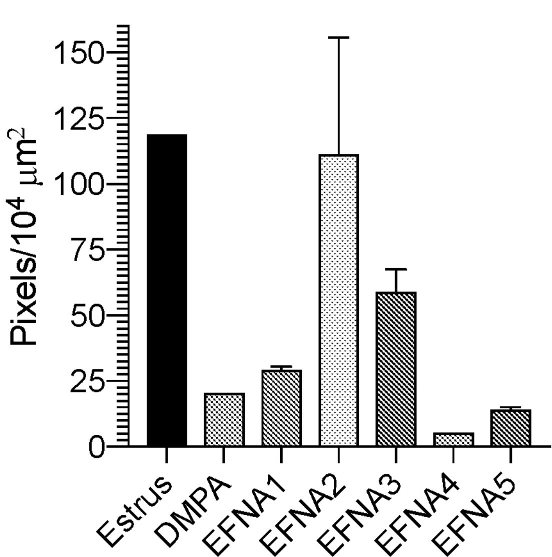

| Diseases and Disorders | p-value range | # Molecules | Upstream Regulator | Expr Log Ratio | z-score | p-value of overlap | Target molecules in dataset |
|---|---|---|---|---|---|---|---|
| Dermatological Diseases and Conditions | 2.38E−03-5.51E−14 | 439 | EFNA3 | −2.593 | −3.000 | 2.98E−05 | ABCA12, DSC1, DSG1, EFNA3, FOXA2, KLK7, KRT16, KRT7, UBE2C |
| Inflammatory Diseases | 2.27E−03-3.27E−08 | 83 | ROCK2 | | −1.387 | 6.05E−03 | DSC1, DSG1, FAS, PPL, SCEL |

rm-EphrinA3 was found to induce similar DSG1 expression as Fc-EphrinA3 (FIG. 7). Congruent with the increase in DSG1 protein levels, administration of rm-EphrinA3 enhanced genital mucosal barrier function in DMPA-treated mice (FIG. 8). Because rm-EphrinA3 treatment reduced vaginal tissue permeability (FIG. 8), its capacity to control genital HSV-1 infection was examined. Estrus-stage or DMPA-treated mice were intravaginally administered vehicle or recombinant mouse Fc-EFNA3 at 1.5 ug/30 uL 24 h prior to genital infection with $3\times10^3$ PFU HSV-1q GFP (fluorescent virus). Vaginal tissue was recovered 24 h after infection and evaluated for HSV-1 replication in the vaginal epithelium using confocal microscopy. Foci of virus replication was observed in DMPA-treated mice, but not in mice in estrus or in DMPA-treated mice treated with Fc-EFNA3. These results showed that HSV-1 replication in mouse genital tissue was reduced by rm-EphrinA3 treatment. To evaluate if treatment with rm-EphrinA3 protects mice from lethal HSV-2 infection, DMPA-treated mice were intravaginally administered Fc- or His-tagged versions of the rm-protein prior to infection. These studies showed that one dose of rm-EphrinA3 reduced mortality approximately 25% compared to mice treated with DMPA alone (FIGS. 9A-B). Because the microarray data indicated EphrinA1, EphrinA2, EphrinA3, EphrinA4, and EphrinA5 were upstream regulators of Dsg1 and Dsc1 expression in the mouse vagina, we hypothesized that capacity of EphrinA3 to increase cell-cell adhesion molecule expression may be shared by other members of the EphrinA family. In examining DSG1 gene and protein expression in DMPA-treated mice, treatment with EphrinA2 or EphrinA3 was found to similarly increase levels of DSG1 protein in vaginal tissue (FIGS. 10A-B).

Figure 5A:
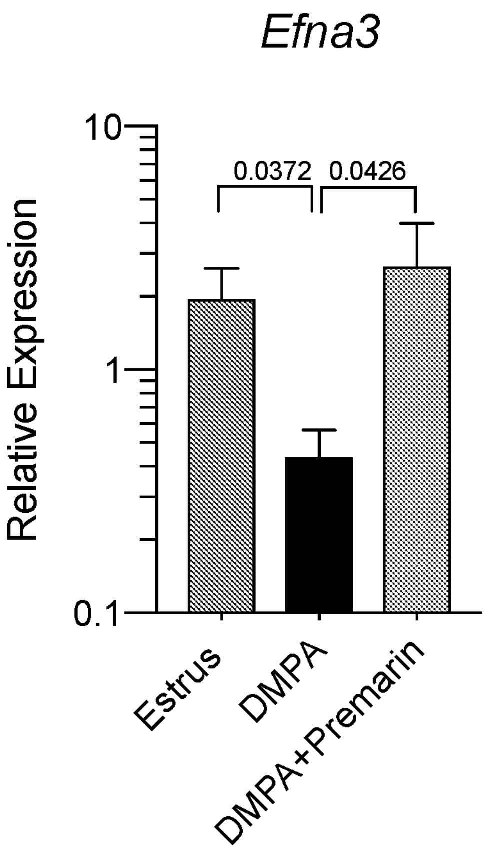
FIG. 5A-B show DMPA reduces EFNA3 expression in mouse vaginal tissue. Vaginal tissue was harvested from mice in estrus, DMPA-treated mice, and mice treated with DMPA and Premarin vaginal cream were placed in RNAlater® for RNA isolation or embedded in formaldehyde for histology analysis.
Figure 5B:
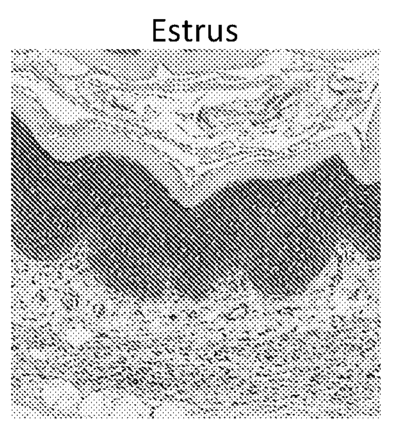
Figure 5B:
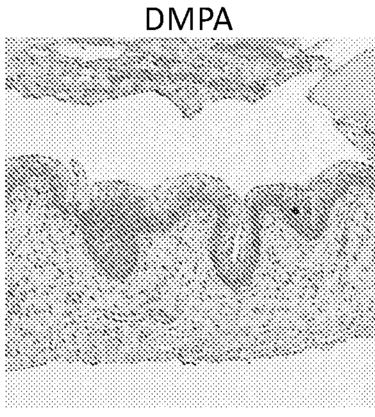
Figure 5B:
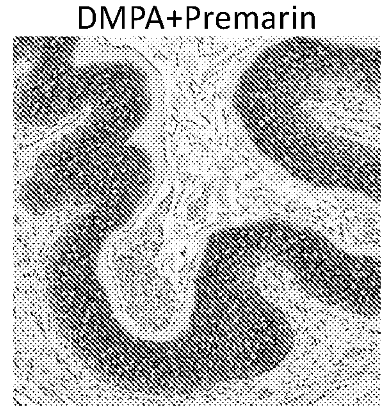
Figure 5B:
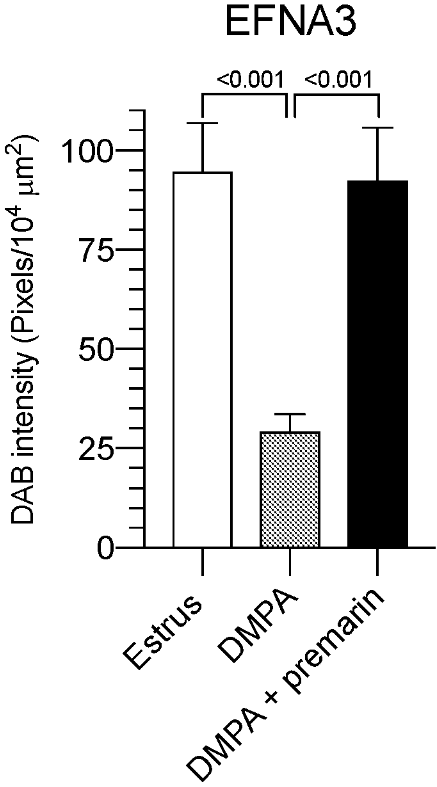
Figure 6:
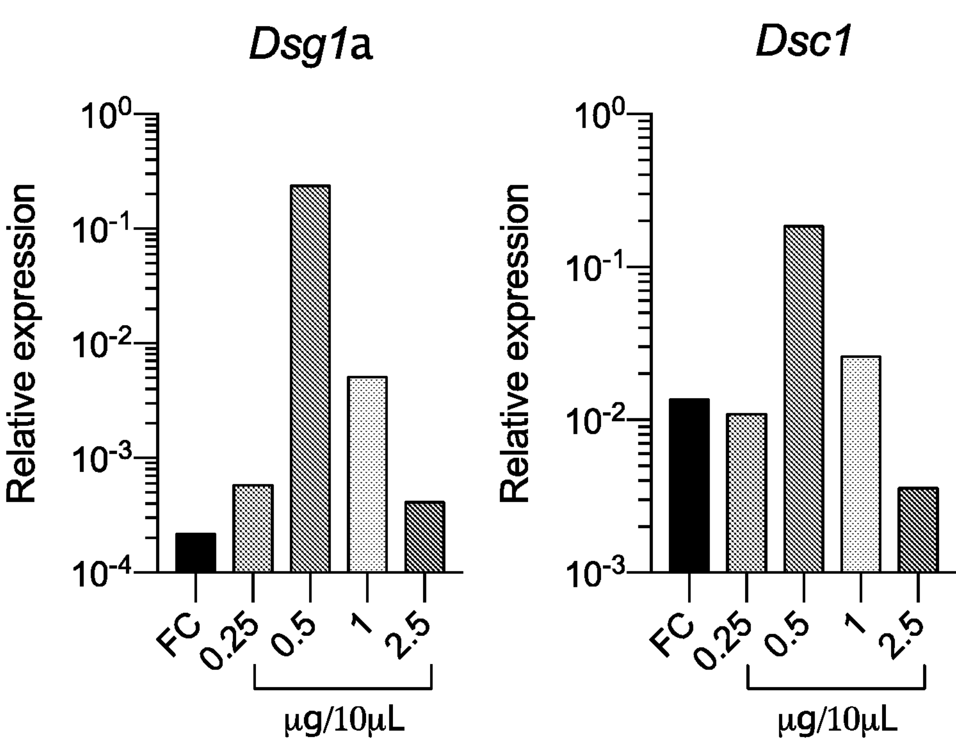
FIG. 6 is bar graphs shows increased expression of Dsg1a (left panel) and Dsc1 (right panel) in mice treated with select doses of EFNA3. DMPA treated-mice were intravaginally administered Fc-control or recombinant mouse Fc-EFNA3 at indicated doses. Vaginal tissues were collected at 6 h. qRT-PCR was used to define relative expression of Dsg1a and Dsc1 gene

To corroborate microarray results, EphrinA3 gene and protein expression were compared in estrus-stage and DMPA-treated mice. To also evaluate effects of exogenous estrogen, other DMPA-treated mice were treated intravaginally with the estrogen cream Premarin. Using RT-PCR and immunohistochemistry assays, DMPA was observed to dramatically impair expression of EphrinA3 in vaginal mucosal tissue whereas exogenous estrogen restored these levels (FIG. 5A-B). While the microarray analyses indicated EphrinA1, EphrinA2, EphrinA3, EphrinA4, and EphrinA5 are upstream regulators of Dsg1a and Dsc1, only EphrinA3 was downregulated by progestin treatment. Based on these results, it was posited that treatment with mouse recombinant EphrinA3 will at least partially reverse DMPA-diminished expression of Dsg1a. To test this hypothesis, DMPA treated-mice were intravaginally administered Fc-control or recombinant mouse Fc-EFNA3 at doses of 0.25 μg, 0.5 μg, 1 μg and 2.5 μg in a 10 μL volume. Six hours after treatment, Dsg1a and Dsc1 gene expression was shown to be optimized by the 0.5 ug dose of Fc-EFNA3 (FIG. 6). Likewise, the levels of DSG1 protein 24 hours after treatment were optimized by the 0.5 ug dose (FIG. 7). Twenty-four hours after treatment vaginal tissues were collected and formaldehyde-fixed for paraffin-embedding. The vaginal tissue was assessed for DSG1 protein levels using immunofluorescent staining and confocal microscopy. A dose-dependent increase in DSG1 protein expression was observed up to the 1 μg dose. However, DSG1 expression was reduced at higher doses. In follow-up studies, 1.5 ug of Fc-EphrinA3 in 30 uL of PBS was shown to induce more homogeneous expression of DSG1 protein than 0.5 ug of Fc-EphrinA3 in 10 uL of PBS.

Figure 11A:
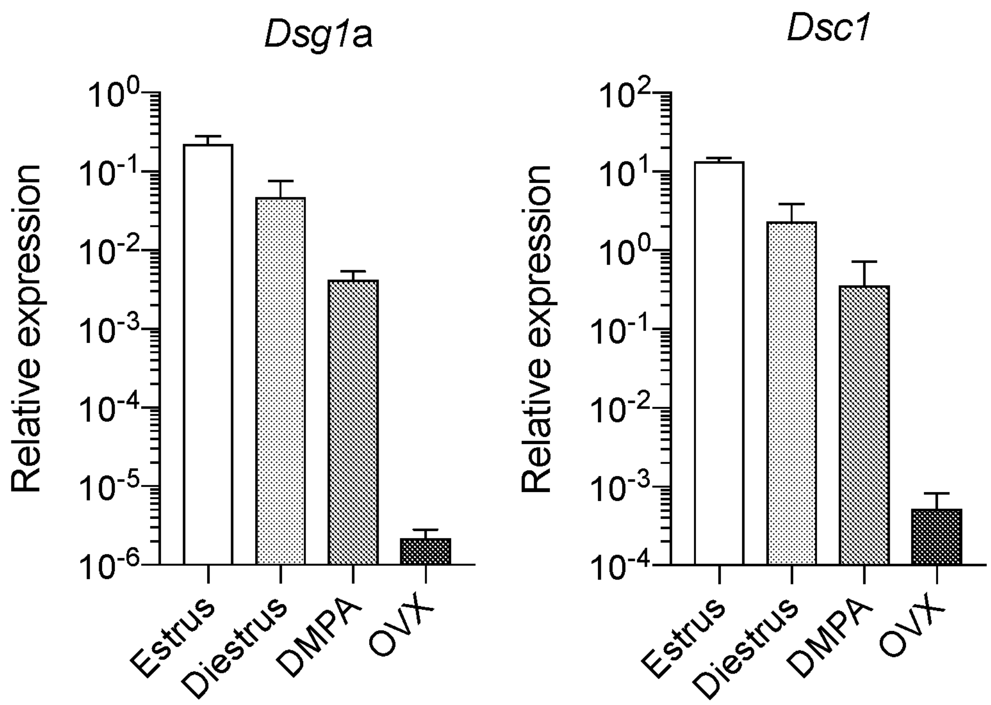
FIG. 11A-B are bar graphs showing decreased levels of select cell-cell adhesion molecules in the genital tract of OVX mice. Relative expression of Dsg1a and Dsc1 genes, left and right panel, respectively (FIG. 11A) and DSG1 protein levels in vaginal tissue (FIG. 11B). qRT-PCR assays measured the relative expression of Dsg1a and Dsc1 genes and DSG1 protein levels in vaginal tissue of mice in estrus, mice in diestrus, DMPA-treated mice, or mice after ovariectomization (OVX, i.e., mice that model the effects of menopause in women) (FIG. 11A). Confocal microscopy was used to define DSG1 protein levels in these same treatment groups (FIG. 11B).
Figure 11B:
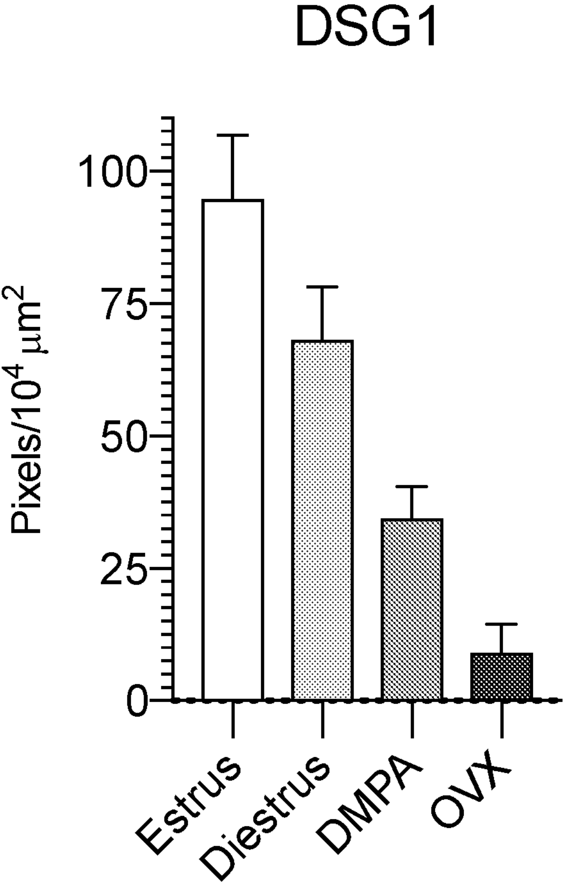
Figure 12A:
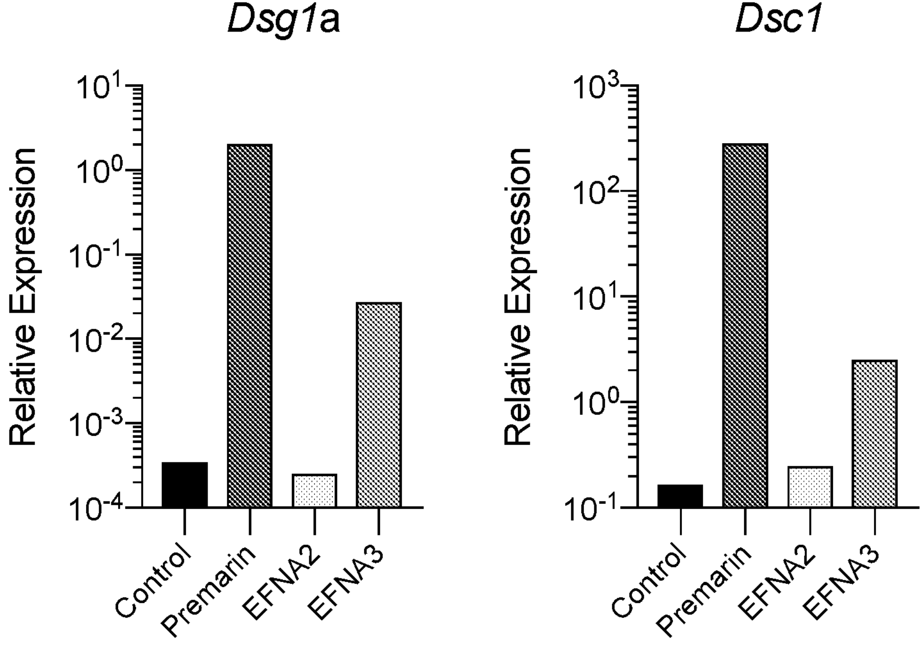
FIG. 12A-B are bar graphs showing that EFNA3 treatment increases Dsg1a and Dsc1 gene expression, left and right panel, respectively (FIG. 12A) and DSG1 protein levels (FIG. 12B) in vaginal tissue of OVX mice. OVX mice were treated with vehicle (Control), Premarin (a commercially available estrogen cream administered daily for 3 consecutive days), or a single dose of EFNA2 or EFNA3. 24 h later, vaginal tissue was obtained and RNA isolated for analysis of gene expression by qRT-PCR. Alternatively, tissue was fixed in formaldehyde and paraffin-embedded tissues for measurement of DSG1 protein levels.
Figure 12B:
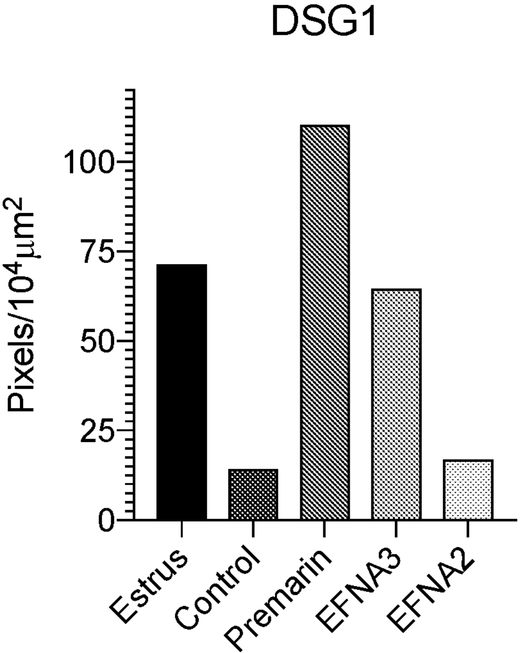
Figure 13:
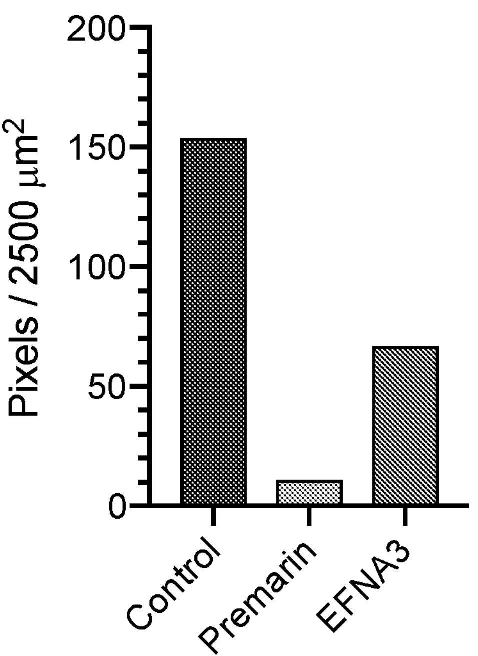
FIG. 13 is a bar graph illustrating that EFNA3 treatment improves genital mucosal barrier function in OVX mice. OVX mice received vehicle (Ctrl), Premarin (daily for 3 consecutive days), or a single dose of EFNA3, and confocal microscopy used to evaluate genital mucosal permeability to LMW fluorescent molecules. Quantification of the penetration of lucifer yellow (457 Da) showed that compared to untreated OVX controls, EFNA3 treatment enhanced genital mucosal barrier function.

The effects of another commercially available rm-EphrinA3 (i.e., a histidine [His]-tagged) were evaluated, and this Menopause is a physiological event connected to loss of ovarian function. In post-menopausal women, vaginal atrophy and painful intercourse are consequences of ovarian function loss. Ovariectomized (OVX) mice were used to model menopause. OVX mice have dramatically reduced gene expression of Dsc1a and Dsc1, leading to a decreased of DSG1 protein expression. Loss of ovarian function was found to be associated with significantly reduced vaginal tissue expression of Dsc1a and Dsc1 genes and DSG1 protein and that genital mucosal barrier function is dramatically compromised in OVX mice (FIGS. 11A-B). When genital mucosal permeability to LMW molecules was evaluated, it was clear that ovariectomized mice had a drastic reduction in mucosal barrier function. As vaginal tissue from OVX mice had less DSG1 protein and compromised genital mucosal barrier function, it was posited that compared to untreated controls, treatment of OVX mice with EphrinA2 or EphrinA3 will increase genital mucosal epithelial integrity. These studies showed that a single intravaginal dose of EphrinA3 greatly improved vaginal tissue levels of Dsg1a and DSG1 protein (FIGS. 12A-B). Likewise, EphrinA3 treatment improved function of the genital mucosal barrier compared to that seen in untreated OVX mice (FIG. 13).

Collectively, these studies demonstrate that recombinant Fc-EFNA3, and to some extent Fc-EFNA2, enhanced genital mucosal barrier function via increased expression of epithelial cell-cell adhesion molecules, especially DSG1.

Potential application for these discoveries includes use of EphrinA family molecules as a vaginal microbicide to lower risk of sexual transmission of HIV and other sexually transmitted infections. Another potential application is a nonhormonal treatment for vaginal atrophy and dyspareunia in perimenopausal and postmenopausal women. A third potential application is a treatment to boost wound healing and barrier function at non-genital epithelial sites (including as a treatment for individuals with atopic dermatitis, eosinophilic esophagitis or asthma).

Example 2: Agonist EFNA3-Derived Peptide Dimer Increases Expression of Cell-Cell Adhesion Molecules in Genital Mucosal Epithelium It was further proposed that peptides derived from EFNA3 could potentially enhance genital mucosal barrier function. Results from studies provided below show that topical administration of the agonist EFNA3-derived peptide dimer significantly increases expression of cell-cell adhesion molecules in genital mucosal epithelium. This effect improves epithelial integrity and barrier function in mice with impaired genital mucosal barrier function, such as ones treated with progestin-only hormonal contraceptives or ovariectomized (OVX) mice.

This effect may benefit women using progestin-only hormonal contraceptives, suffer from the genitourinary syndrome of menopause, or display ovarian failure due to chemotherapy. Reduced genital mucosal barrier function is also a significant risk factor for genital transmission of HIV and other microbial pathogens and this treatment effect may reduce this risk.

Figure 14:
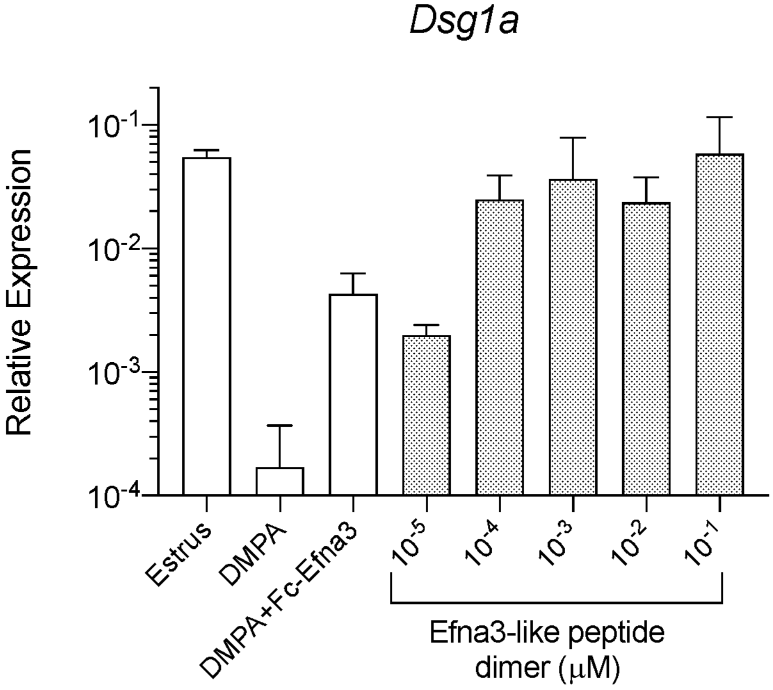
FIG. 14 is a bar graph showing that EFNA3-derived peptide dimer promotes Dsg1a mouse vaginal expression in DMPA-treated mice. In these experiments, female mice in estrus, female mice systemically treated with DMPA 5 days earlier, or treated with DMPA and intravaginally with Fc-EFNA3 (1 μM) or indicated concentrations of EFNA3-derived peptide dimer diluted in PBS, were euthanized 24 hours after treatment. Vaginal tissue was collected for RNA isolation and quantification of Dsg1a expression via qRT-PCR
Figure 15A:
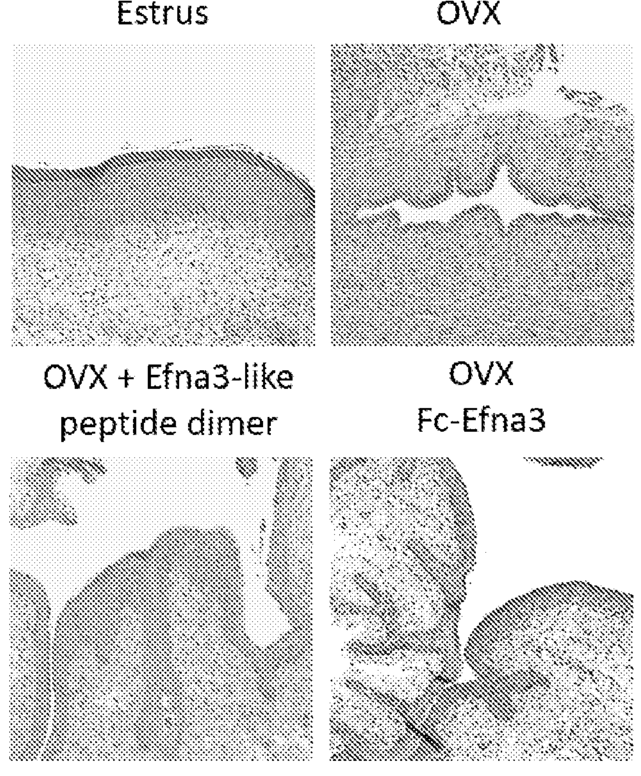
FIG. 15A-B are representative images of vaginal tissue (FIG. 15A) and a bar graph (FIG. 15B) illustrating that EFNA3-derived peptide dimer or Fc-EFNA3 improves vaginal epithelial integrity in OVX mice. Mice in estrus and OVX mice were used in these experiments. OVX mice received PBS alone, EFNA3-derived peptide dimer ($10^{-4}$ μM) or recombinant mouse Fc-EFNA3 (1 μM) via atraumatic intravaginal administration for 9 consecutive days. All mice were euthanized, and vaginal tissue processed for histological evaluation and measurement of vaginal epithelial thickness.
Figure 15B:
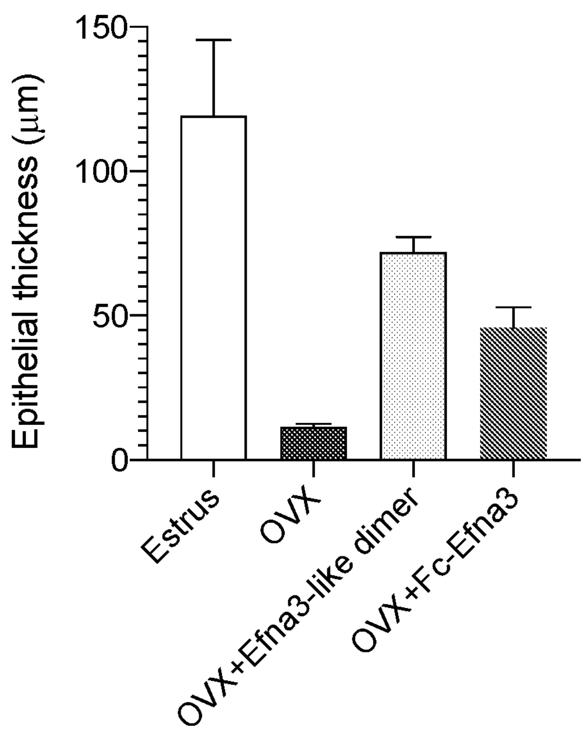
Figure 16:
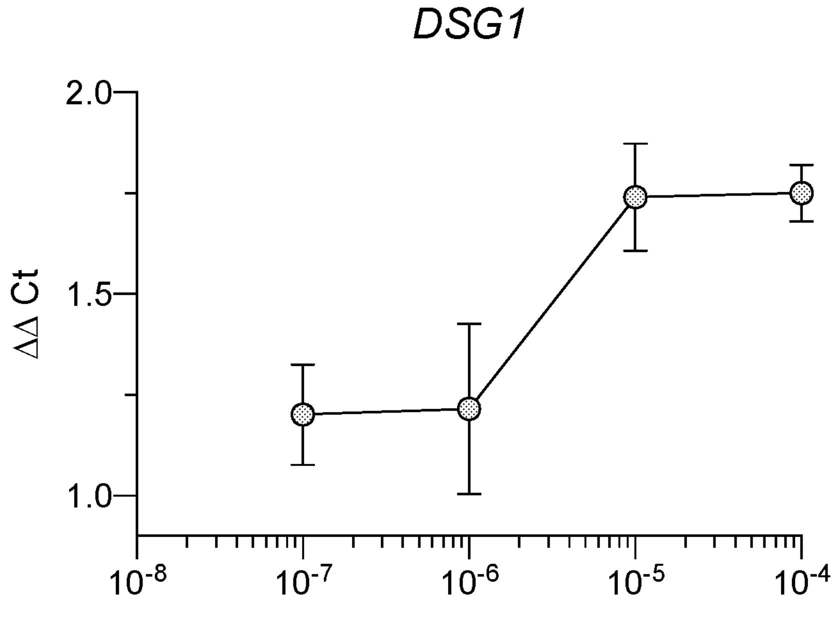
FIG. 16 is a bar graph illustrating that EFNA3-derived peptide dimer promotes DSG1 expression in immortalized human vaginal epithelial cells. VK2/E6E7 vaginal cells at 70-90% confluency were treated with indicated concentrations of EFNA3-derived peptide dimer for 24 h. Cells were harvested for RNA isolation and determination of relative DSG1 gene expression via qRT-PCR and $\Delta\Delta C_t$ analysis.

Topical administration of an EFNA3-derived peptide dimer (SEQ ID NO:6) promotes Dsg1a mouse vaginal expression in DMPA-treated mice (FIG. 14) with greater potency compared to recombinant mouse Fc-EFNA3. EFNA3-derived peptide dimer and Fc-EFNA3 also improved vaginal epithelial integrity in OVX mice (FIGS. 15A and 15B). These results thus indicate that EFNA3-derived peptide dimer and Fc-EFNA3 could represent a non-hormonal therapeutic option for women experiencing the genitourinary syndrome of menopause. Similarly, these 2 agents have potential to reverse the effects on the genital mucosal epithelium exerted by progestin-only contraceptives and help reduce susceptibility to sexually transmitted infections. To further support its potential effect in humans, studies provided herein show that EFNA3-derived peptide dimer can increase DSG1 expression in immortalized human vaginal epithelial cells in vitro (FIG. 16).

Example 3: Fc-EFNA3 Promotes Skin Epithelial Barrier Function

Figure 17:
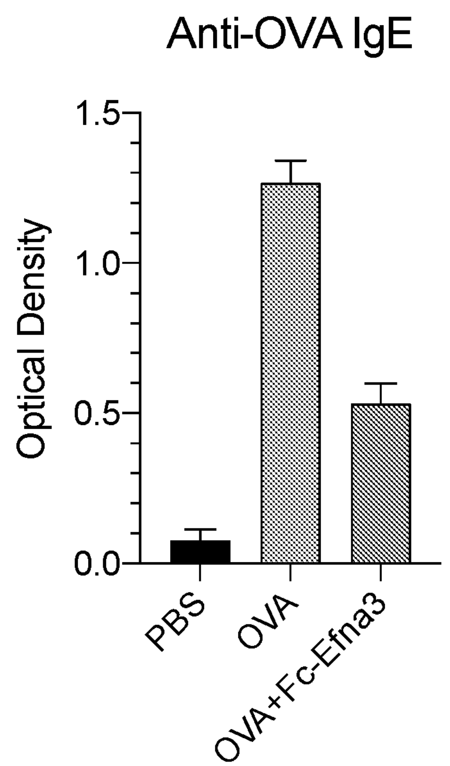
FIG. 17 is a bar graph showing Fc-EFNA3 promotes skin epithelial barrier function and reduces allergen sensitization in a mouse model of atopic dermatitis. Mice underwent epicutaneous sensitization with OVA alone or in combination with recombinant mouse Fc-EFNA3. After 3 sensitization cycles, animals were euthanized to obtain blood for serum isolation. Then, levels of serum anti-OVA IgE was determined via ELISA.

Topical administration of recombinant mouse Fc-EFNA3 also decreased allergen-specific IgE levels in a mouse model of epicutaneous sensitization-induced atopic dermatitis (FIG. 17). This first demonstration showcases Fc-EFNA3 or derived peptides as therapeutic agents capable of boosting epithelial barrier function in various clinically significant settings, including allergic diseases. The results provided herein indicate EFNA3 or EFNA3-like dimer could be useful in treatment of atopic dermatitis via improvement of skin barrier function, considered a key factor in the pathogenesis of this disease. Thus, there are applications in other similar conditions, such as eosinophilic esophagitis, in which downregulation of DSG1 expression is observed.

Example 4: Materials and Methods

Determining Estrous Cycle Stage:

A saline solution was used to collect cervicovaginal lavages from mice, and specimens placed on glass slides to dry. Slides were stained with a 0.1% crystal violet solution and evaluated by light microscopy. Estrus cycle stage identification was based on variable presence of cornified epithelial cells, nucleated epithelial cells, and neutrophils.

Murine Tissue Permeability Assays:

To evaluate mucosal permeability to low molecular weight molecules, indicated groups of mice were sedated, and 10 μL of a PBS solution containing 62.5 μg of dextran Texas-Red® (DR) (MW=70,000 Da) and 50 μg of Lucifer yellow CH, lithium salt (LY) (MW=457.2 Da) (both from Life Technologies) administered intravaginally. 45 minutes later, mice were euthanized, and excised vaginal tissue fixed in formaldehyde. Fixed tissue was embedded in agarose, and 200-300 μm specimens were sectioned with a vibratome. After counterstaining with 4,6-diamidino-2-phenylindole (DAPI), confocal microscopy images were acquired by sequential scanning to prevent fluorescence crossover.

To evaluate mucosal permeability to activated leukocytes, $10^6$ human peripheral blood mononuclear cells (hPBMC)/ml were plated in RPMI-1640 supplemented with 10% FBS, 2 mM L-glutamine, 1 mM sodium pyruvate, non-essential amino acids, 50 μM 2-mercaptoethanol, 100 U/ml penicillin, 100 μg/ml streptomycin and 50 μg/ml gentamycin (Mediatech, Manassas, VA) (henceforth termed complete medium). Plated cells were stimulated for 48 hours with 5 μg/ml of phytohemagglutinin (PHA) (Sigma-Aldrich, St. Louis MO), centrifuged, re-suspended ($2\times10^6$ cells/ml) in complete media supplemented with 10 IU/ml recombinant human IL-2 (rhIL-2) (PeproTech, Rocky Hill, NJ), and incubated another 5 days. These activated leukocytes were labelled with 5 μM of carboxyfluorescein succinimidyl ester (CellTrace CFSE; Life Technologies), resuspended in PBS ($10^8$ cells/ml), and mice intravaginally inoculated with 10 μl of this cell suspension. After 15 hours, mice were euthanized, and vaginal tissue fixed in formaldehyde, agarose-embedded, and DAPI stained. Fluorescent signal from CSFE-labelled hPBMC were used to assess depth of leukocyte infiltration into vaginal tissue via confocal microscopy and ImageJ software.

Human Tissue Permeability Assay:

Endocervical biopsy specimens obtained from women were placed in transport media, transferred into sterile 96-well plates, and incubated 45 minutes in a 20 μL solution of PBS containing LY and DR (at the same concentrations used in mouse studies). Tissue was likewise fixed and embedded as detailed for mice. Stratified squamous epithelium, lamina propria, and connective tissue were identified using light microscopy (at 100× magnification), while images obtained at 400× magnification were used to quantify penetration of LY into ectocervical tissue.

RNA Isolation and Quantitative Real Time (qRT)-PCR Assays:

Human ectocervical and murine vaginal tissues were immediately immersed in 1 mL of RNAlater® (Qiagen), stored for 24 h at 4° C., and stored long-term at −80° C. RNA isolated using the RNeasy Lipid Tissue Kit (Qiagen) using manufacturer's instructions was re-suspended in nuclease-free water and quantified using a NanoDrop spectrophotometer (Thermo Scientific). The following mouse primers were utilized: desmocollin 1 (Mm00496525_ml), desmoglein-1α (Mm00809994_s1), ephrinA3 (Mm01212723_g1) and pyruvate carboxylase (Mm00500992_ml) as housekeeping reference gene (all from Thermo Scientific). These human primers were used: desmoglein-1 (Hs00355084_m1) and glucose-6-phosphate isomerase (Hs00976711_m1) as a housekeeping reference gene. To define relative gene expression, 100 ng of RNA was mixed with TaqMan® RNA-to-Ct™ 1-Step Kit and adequate primer (final volume of 10 μL/well) using manufacturer's instructions (Life Technologies). qRT-PCR was performed using a Quantstudio3 Thermal Cycler, and data analyzed via Quanstudio Software (Applied Biosystems).

Immunofluorescence Assays:

Excised mouse vaginas were formaldehyde fixed and paraffin embedded (FFPE), and 10 μm sections mounted on glass slides and de-paraffinized by sequential immersion in 100% xylene, 100% ethanol, 96% ethanol, and sterile DEPC-treated water. Antigen retrieval was performed using 10 mM sodium citrate buffer (pH 6.0) containing 0.05% Tween 20 (both Sigma-Aldrich) (20 minutes at 95° C.). After 3 PBS washes, sections were incubated overnight in 10% normal goat serum (Abcam, Cambridge MA) at 4° C., then incubated for 1 h at ambient temperate with rabbit anti-desmoglein-1 (clone EPR6766(B)) antibody, washed and incubated for 1 h with AlexaFluor® 488-labeled goat anti-rabbit IgG (antibodies from Abcam) (all antibodies were diluted in PBS with 1% BSA and 0.05% Tween 20). Sections were stained with DAPI and evaluated for levels of DSG1 protein (defined by calculating pixel numbers per 100 $\mu m^2$) using confocal microscopy and ImageJ software.

Immunohistochemistry Assays:

10 μm sections of FFPE murine vaginal tissue were mounted on glass slides and de-paraffinized by sequential immersion in 100% xylene, 100% ethanol, 96% ethanol, and sterile DEPC-treated water. Antigen retrieval was performed using 10 mM sodium citrate buffer (pH 6.0) containing 0.05% Tween 20 for 20 minutes at 95° C. (endogenous peroxidase activity quenched using 3% hydrogen peroxidase). Blocking was performed in 10% normal goat serum (Cell Signaling Technology®) for 4 h at 4° C., and sections incubated for 1 h at 4° C. with rabbit anti-ephrinA3 (LifeSpan BioSciences) (in 1:200 dilutions using SignalStain® antibody diluent (Cell Signaling Technology®). Using manufacturer's instructions, slides were washed 3× in PBS, incubated with Signal Stain® Boost detection and Signal Stain® BAD Chromogen (both Cell Signaling Technology®), and counterstained with hematoxylin. Coverslips were placed using Signal Stain® mounting medium (Cell Signaling Technology®), and slides examined using a NanoZoomer 2.0-RS slide scanner (Hamamatsu Photonics K.K. Hamamatsu City, Japan). Quantitative analyses were performed using ImageJ software.

HSV-2 Infection:

Mice were sedated with xylazine (Lloyd Laboratories, Shenandoah IA) and ketamine hydrochloride (JHP Pharmaceuticals, LLC Rochester MI), and intravaginally infected with $10^4$ plaque-forming units (pfu) of WT HSV-2 333 in 10 μL of RPMI. Mouse mortality was evaluated daily for 15 days.

HIV-1 Infection:

hPBMCs activated as indicated above were inoculated with 600 $TCID_{50}$ of HIV-1 BaL for 24 hour and re-suspended in PBS ($10^8$ cells/ml) (portions of these HIV-1-infected hPBMC culture were used in a luciferase gene reporter assay to confirm HIV-1 infectivity). NSG mice reconstituted with non-activated hPBMC were anaesthetized with xylazine and ketamine hydrochloride, and intravaginally inoculated with $10^6$ (10 μl) of HIV-1-infected hPBMCs. Mice were euthanized 10 days later to assess HIV-1 infection status. At euthanasia, plasma was separated from blood and stored at −80° C. Approximately ⅔ of an excised spleen was transferred to chilled complete medium, with the rest placed in buffered 4% formaldehyde for 24 hours (Thermo Scientific). Splenic tissue in media was processed into single-cell suspension and cultured in complete medium supplemented with rhIL-2 (media replenished every 3 days). After 8 days, supernatants were incubated with TZM-bl indicator cells to detect infectious HIV-1 particles. In these assays, splenocytes from uninfected mice provided negative controls and HIV-1 BaL diluted in complete media served as positive controls. Plasma HIV-1 load was quantified using Abbott's real-time PCR assay (an FDA-approved test).

Mouse Ovariectomy:

8-10 weeks female C57BL/6J mice were anesthetized. Dorsal skin was shaved and cleaned with 70% ethanol followed by povidone-iodine. Following appropriate sterile technique, a single dorsal skin incision was performed, followed by dissection until ovarian fat pads were identified and ovaries removed. Peritoneal and abdominal walls were sutured, and mice recovered from anesthesia. After confirmation of suppression of estrous cycle, mice were used in experiments.

DSG1 Gene Expression in Human Vaginal Epithelial Cell Lines:

VK2/E6E7 (ATCC® CRL-2616™) vaginal epithelial cell line was grown using ReproLife™ Reproductive Medium Complete Kit for up to 4 passages. For experiments, $10^5$ cells were plated in 12-well plates. Cells reached 70-90% confluency after 24 hand were stimulated with EFNA3-like peptide dimer or vehicle. Cells were incubated for 24 h with indicated treatments. RNA was extracted and 500 ng of RNA used to generate cDNA using the SuperScript™ IV VILO™ Master Mix. Relative DSG1 (Hs00355084_m1) gene expression was calculated by normalization with the housekeeping gene glucose-6-phosphate isomerase (Hs00976711_m1) via qRT-PCR.

Mouse Epicutaneous Sensitization:

6-10 weeks old Balb/cJ mice were anesthetized. Dorsal skin was shaved, and skin tape-stripped 6 times. PBS alone, 100 μg of ovalbumin (OVA) in PBS or 100 μg OVA+recombinant mouse Fc-EFNA3 in 100 μl of PBS were added to a 1×1 cm sterile gauze that was applied directly to tape-stripped area of skin and covered with a transparent bio-occlusive dressing. This patch was left in place for a 1-week period and removed. This procedure was repeated twice with 2-week intervals between applications. After completing the $3^{rd}$ skin sensitization, mice were euthanized and serum samples obtained. Serum levels of anti-OVA IgE were was determined using an in-house ELISA.

Protein Expression

For Ephrin A3 protein Mouse (Recombinant with His Tag) expression, a DNA sequence encoding the mouse EFNA3 (NP_034238.1) without the pro peptide (Met 1-Ser 205) was expressed, with a polyhistidine tag at the C-terminus. The recombinant mouse EFNA3 consists of 194 amino acids and has a predicted molecular mass of 22.2 kDa.

For Ephrin A3 protein (Human, Recombinant with His Tag) expression, a DNA sequence encoding the human EphrinA3 (NP_004943.1) (Met 1-Ser 213) with the C-terminal propeptide removed was expressed, with a polyhistidine tag at the C-terminus. The recombinant human EphrinA3 consists of 202 amino acids after removal of the signal peptide and has a predicted molecular mass of 23 kDa.

For Ephrin A2/EFNA2 protein (Mouse, Recombinant with His Tag) expression, a DNA sequence encoding the mouse EFN A2 (NP_031935.3) without the pro peptide (Met 1-Asn 184) was expressed, with a polyhistidine tag at the C-terminus.

What is claimed is:

1. A synthetic or recombinant peptide comprising an amino acid sequence at least 90% identical to SEQ ID NO:6, SEQ ID NO:13 or SEQ ID NO: 14.

2. The peptide of claim 1, wherein the peptide comprises an amino acid sequence at least 90% identical to SEQ ID NO:6.

3. The peptide of claim 2, wherein the peptide comprises at least one non-naturally occurring amino acid.

4. The peptide of claim 1, wherein the peptide comprises an amino acid sequence at least 90% identical to SEQ ID NO:13 or SEQ ID NO:14.

5. A pharmaceutical composition comprising an oligonucleotide encoding the peptide of claim 1.

6. The pharmaceutical composition of claim 5, wherein the oligonucleotide comprises an expression vector.

7. A pharmaceutical composition comprising the peptide of claim 1 and a pharmaceutically acceptable carrier.

8. The pharmaceutical composition of claim 7, wherein the composition is formulated for topical administration.

9. The pharmaceutical composition of claim 7, wherein the composition comprises a progestin, optionally wherein the progestin comprises conjugated estrogens.

10. A method for modulating epithelial barrier function in a subject in need thereof, the method comprising administering to the subject an effective amount of the pharmaceutical composition of claim 7, wherein modulating epithelial barrier function is:

(i) reducing female genital tract barrier permeability or reducing vaginal atrophy;

(ii) increasing vaginal expression of desmoglein 1 (DSG 1) or desmocollin-1 (DSC1);

(iii) increasing skin barrier function; and/or (iv) decreasing penetration of antigens or microbiota through skin or vaginal epithelium.

11. The method of claim 10, wherein the modulating epithelial barrier function comprises reducing female genital tract barrier permeability or reducing vaginal atrophy.

12. The method of claim 10, wherein the modulating epithelial barrier function comprises increasing skin barrier function; and/or decreasing penetration of antigens or microbiota through skin or vaginal epithelium.

13. A method of treating a disease or condition in a subject in need thereof comprising administering to the subject an effective amount of the pharmaceutical composition of claim 7, wherein the disease or condition is vaginal atrophy or atopic dermatitis.

14. A method of reducing transmission of a sexually transmitted disease in a female subject in need thereof comprising administering to the female subject an effective amount of the pharmaceutical composition of claim 7.

15. A method for promoting wound healing in a subject in need thereof comprising administering to the subject an effective amount of the pharmaceutical composition of claim 7.

* * * * *

```
                              SEQUENCE LISTING


<160> NUMBER OF SEQ ID NOS: 20

<210> SEQ ID NO 1
<211> LENGTH: 238
<212> TYPE: PRT
<213> ORGANISM: Homo sapiens

<400> SEQUENCE: 1

Met Ala Ala Ala Pro Leu Leu Leu Leu Leu Leu Leu Val Pro Val Pro
1               5                   10                  15

Leu Leu Pro Leu Leu Ala Gln Gly Pro Gly Gly Ala Leu Gly Asn Arg
            20                  25                  30

His Ala Val Tyr Trp Asn Ser Ser Asn Gln His Leu Arg Arg Glu Gly
        35                  40                  45

Tyr Thr Val Gln Val Asn Val Asn Asp Tyr Leu Asp Ile Tyr Cys Pro
    50                  55                  60

His Tyr Asn Ser Ser Gly Val Gly Pro Gly Ala Gly Pro Gly Pro Gly
65                  70                  75                  80

Gly Gly Ala Glu Gln Tyr Val Leu Tyr Met Val Ser Arg Asn Gly Tyr
                85                  90                  95

Arg Thr Cys Asn Ala Ser Gln Gly Phe Lys Arg Trp Glu Cys Asn Arg
            100                 105                 110

Pro His Ala Pro His Ser Pro Ile Lys Phe Ser Glu Lys Phe Gln Arg
        115                 120                 125

Tyr Ser Ala Phe Ser Leu Gly Tyr Glu Phe His Ala Gly His Glu Tyr
    130                 135                 140

Tyr Tyr Ile Ser Thr Pro Thr His Asn Leu His Trp Lys Cys Leu Arg
145                 150                 155                 160

Met Lys Val Phe Val Cys Cys Ala Ser Thr Ser His Ser Gly Glu Lys
                165                 170                 175

Pro Val Pro Thr Leu Pro Gln Phe Thr Met Gly Pro Asn Val Lys Ile
            180                 185                 190

Asn Val Leu Glu Asp Phe Glu Gly Glu Asn Pro Gln Val Pro Lys Leu
        195                 200                 205

Glu Lys Ser Ile Ser Gly Thr Ser Pro Lys Arg Glu His Leu Pro Leu
    210                 215                 220

Ala Val Gly Ile Ala Phe Phe Leu Met Thr Phe Leu Ala Ser
225                 230                 235


<210> SEQ ID NO 2
<211> LENGTH: 213
<212> TYPE: PRT
<213> ORGANISM: Homo sapiens

<400> SEQUENCE: 2

Met Ala Pro Ala Gln Arg Pro Leu Leu Pro Leu Leu Leu Leu Leu Leu
1               5                   10                  15

Pro Leu Pro Pro Pro Pro Phe Ala Arg Ala Glu Asp Ala Ala Arg Ala
            20                  25                  30
```

Asn Ser Asp Arg Tyr Ala Val Tyr Trp Asn Arg Ser Asn Pro Arg Phe
35 40 45

His Ala Gly Ala Gly Asp Asp Gly Gly Gly Tyr Thr Val Glu Val Ser
50 55 60

Ile Asn Asp Tyr Leu Asp Ile Tyr Cys Pro His Tyr Gly Ala Pro Leu
65 70 75 80

Pro Pro Ala Glu Arg Met Glu His Tyr Val Leu Tyr Met Val Asn Gly
85 90 95

Glu Gly His Ala Ser Cys Asp His Arg Gln Arg Gly Phe Lys Arg Trp
100 105 110

Glu Cys Asn Arg Pro Ala Ala Pro Gly Gly Pro Leu Lys Phe Ser Glu
115 120 125

Lys Phe Gln Leu Phe Thr Pro Phe Ser Leu Gly Phe Glu Phe Arg Pro
130 135 140

Gly His Glu Tyr Tyr Tyr Ile Ser Ala Thr Pro Pro Asn Ala Val Asp
145 150 155 160

Arg Pro Cys Leu Arg Leu Lys Val Tyr Val Arg Pro Thr Asn Glu Thr
165 170 175

Leu Tyr Glu Ala Pro Glu Pro Ile Phe Thr Ser Asn Asn Ser Cys Ser
180 185 190

Ser Pro Gly Gly Cys Arg Leu Phe Leu Ser Thr Ile Pro Val Leu Trp
195 200 205

Thr Leu Leu Gly Ser
210

<210> SEQ ID NO 3
<211> LENGTH: 230
<212> TYPE: PRT
<213> ORGANISM: Mus musculus

<400> SEQUENCE: 3

Met Ala Ala Ala Pro Leu Leu Leu Leu Leu Leu Leu Val Pro Val Pro
1 5 10 15

Leu Leu Pro Leu Leu Ala Gln Gly Pro Gly Gly Ala Leu Gly Asn Arg
20 25 30

His Ala Val Tyr Trp Asn Ser Ser Asn Gln His Leu Arg Arg Glu Gly
35 40 45

Tyr Thr Val Gln Val Asn Val Asn Asp Tyr Leu Asp Ile Tyr Cys Pro
50 55 60

His Tyr Asn Ser Ser Gly Pro Gly Gly Gly Ala Glu Gln Tyr Val Leu
65 70 75 80

Tyr Met Val Asn Leu Ser Gly Tyr Arg Thr Cys Asn Ala Ser Gln Gly
85 90 95

Ser Lys Arg Trp Glu Cys Asn Arg Gln His Ala Ser His Ser Pro Ile
100 105 110

Lys Phe Ser Glu Lys Phe Gln Arg Tyr Ser Ala Phe Ser Leu Gly Tyr
115 120 125

Glu Phe His Ala Gly Gln Glu Tyr Tyr Tyr Ile Ser Thr Pro Thr His
130 135 140

Asn Leu His Trp Lys Cys Leu Arg Met Lys Val Phe Val Cys Cys Ala
145 150 155 160

Ser Thr Ser His Ser Gly Glu Lys Pro Val Pro Thr Leu Pro Gln Phe
165 170 175

Thr Met Gly Pro Asn Val Lys Ile Asn Val Leu Glu Asp Phe Glu Gly

```
            180                 185                 190

Glu Asn Pro Gln Val Pro Lys Leu Glu Lys Ser Ile Ser Gly Thr Ser
        195                 200                 205

Pro Lys Arg Glu His Leu Pro Leu Ala Val Gly Ile Ala Phe Phe Leu
    210                 215                 220

Met Thr Leu Leu Ala Ser
225                 230


<210> SEQ ID NO 4
<211> LENGTH: 209
<212> TYPE: PRT
<213> ORGANISM: Mus musculus

<400> SEQUENCE: 4

Met Ala Pro Ala Gln Arg Pro Leu Leu Pro Leu Leu Leu Leu Leu Leu
1               5                   10                  15

Pro Leu Arg Ala Arg Asn Glu Asp Pro Ala Arg Ala Asn Ala Asp Arg
            20                  25                  30

Tyr Ala Val Tyr Trp Asn Arg Ser Asn Pro Arg Phe Gln Val Ser Ala
        35                  40                  45

Val Gly Asp Gly Gly Gly Tyr Thr Val Glu Val Ser Ile Asn Asp Tyr
    50                  55                  60

Leu Asp Ile Tyr Cys Pro His Tyr Gly Ala Pro Leu Pro Pro Ala Glu
65                  70                  75                  80

Arg Met Glu Arg Tyr Ile Leu Tyr Met Val Asn Gly Glu Gly His Ala
                85                  90                  95

Ser Cys Asp His Arg Gln Arg Gly Phe Lys Arg Trp Glu Cys Asn Arg
            100                 105                 110

Pro Ala Ala Pro Gly Gly Pro Leu Lys Phe Ser Glu Lys Phe Gln Leu
        115                 120                 125

Phe Thr Pro Phe Ser Leu Gly Phe Glu Phe Arg Pro Gly His Glu Tyr
    130                 135                 140

Tyr Tyr Ile Ser Ala Thr Pro Pro Asn Leu Val Asp Arg Pro Cys Leu
145                 150                 155                 160

Arg Leu Lys Val Tyr Val Arg Pro Thr Asn Glu Thr Leu Tyr Glu Ala
                165                 170                 175

Pro Glu Pro Ile Phe Thr Ser Asn Ser Ser Cys Ser Gly Leu Gly Gly
            180                 185                 190

Cys His Leu Phe Leu Thr Thr Val Pro Val Leu Trp Ser Leu Leu Gly
        195                 200                 205

Ser


<210> SEQ ID NO 5
<211> LENGTH: 12
<212> TYPE: PRT
<213> ORGANISM: Homo sapiens

<400> SEQUENCE: 5

Arg Tyr Ser Ala Phe Ser Leu Gly Tyr Glu Phe His
1               5                   10


<210> SEQ ID NO 6
<211> LENGTH: 26
<212> TYPE: PRT
<213> ORGANISM: Artificial Sequence
<220> FEATURE:
<223> OTHER INFORMATION: Synthetic polypeptide
<220> FEATURE:
```

<221> NAME/KEY: MISC_FEATURE
<222> LOCATION: (13)..(13)
<223> OTHER INFORMATION: aminohexanoic acid

<400> SEQUENCE: 6

```
Arg Tyr Ser Ala Phe Ser Leu Gly Tyr Glu Phe His Xaa Lys His Phe
1               5                   10                  15

Glu Tyr Gly Leu Ser Phe Ala Ser Tyr Arg
            20                  25
```

<210> SEQ ID NO 7
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 7

```
Ile Glu Gly Arg Met Asp Pro
1               5
```

<210> SEQ ID NO 8
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 8

```
Ile Glu Gly Arg Met Asp
1               5
```

<210> SEQ ID NO 9
<211> LENGTH: 1817
<212> TYPE: DNA
<213> ORGANISM: Artificial Sequence
<220> FEATURE:
<223> OTHER INFORMATION: Synthetic polynucleotide

<400> SEQUENCE: 9

```
ggcctaaggc tgggggccga cggcggcggc agcagggagc tgggaagcgg agaagccggg     60

agcgcggggc tcagtcgggg ggcggcggcg gcggcggctc cggggatggc ggcggctccg    120

ctgctgctgc tgctgctgct cgtgcccgtg ccgctgctgc cgctgctggc ccaagggccc    180

ggaggggcgc tgggaaaccg gcatgcggtg tactggaaca gctccaacca gcacctgcgg    240

cgagagggct acaccgtgca ggtgaacgtg aacgactatc tggatattta ctgcccgcac    300

tacaacagct cgggggtggg ccccggggcg ggaccggggc ccggaggcgg ggcagagcag    360

tacgtgctgt acatggtgag ccgcaacggc taccgcacct gcaacgccag ccagggcttc    420

aagcgctggg agtgcaaccg gccgcacgcc ccgcacagcc ccatcaagtt ctcggagaag    480

ttccagcgct acagcgcctt ctctctgggc tacgagttcc acgccggcca cgagtactac    540

tacatctcca cgcccactca caacctgcac tggaagtgtc tgaggatgaa ggtgttcgtc    600

tgctgcgcct ccacatcgca ctccggggag aagccggtcc ccactctccc ccagttcacc    660

atgggcccca atgtgaagat caacgtgctg gaagactttg agggagagaa ccctcaggtg    720

cccaagcttg agaagagcat cagcgggacc agccccaaac gggaacacct gcccctggcc    780

gtgggcatcg ccttcttcct catgacgttc ttggcctcct agctctgccc cctcccctgg    840

ggggggagag atggggcggg gcttggaagg agcagggagc ctttggcctc tccaagggaa    900

gcctagtggg cctagacccc tcctcccatg gctagaagtg ggcctgcac catacatctg     960
```

```
tgtccgcccc ctctacccct tccccccacg tagggcactg tagtggacca agcacgggga   1020

cagccatggg tcccgggcgg ccttgtggct ctggtaatgt ttggtaccaa acttgggggc   1080

caaaaagggc agtgctcagg actccctggc ccctggtacc tttccctgac tcctggtgcc   1140

ctctcccttt gtccccccag agagacatat gcccccagag agagcaaatc gaagcgtggg   1200

aggcaccccc attgctctcc tccaggggca gaacatgggg aggggactag atgggcaagg   1260

ggcagcactg cctgctgctt ccttcccctg tttacagcaa taagcacgtc ctcctccccc   1320

actcccactt ccaggattgt ggtttggatt gaaaccaagt ttacaagtag acacccctgg   1380

gggggcgggc agtggacaag gatggcaagg ggtgggcatt ggggtgccag gcaggcatgt   1440

acagactcta tatctctata tataatgtac agacagacag agtcccttcc ctctttaacc   1500

ccctgacctt tcttgacttc cccttcagct tcagacccct tccccaccag gctaggcccc   1560

ccacacctgg gggacccccct ggcccctctt ttgtcttctg tgaagacagg acctatgcaa   1620

cgcacagaca cttttggaga ccgtaaaaca acaacgcccc ctcccttcca gccctgagcc   1680

gggaaccatc tcccaggacc ttgccctgct caccctatgt ggtcccacct atcctcctgg   1740

gcctttttca agtgctttgg ctgtgacttt catactctgc tcttagtcta aaaaaaataa   1800

actggagata aaaataa                                                  1817
```

```
<210> SEQ ID NO 10
<211> LENGTH: 2424
<212> TYPE: DNA
<213> ORGANISM: Artificial Sequence
<220> FEATURE:
<223> OTHER INFORMATION: Synthetic polynucleotide

<400> SEQUENCE: 10

ggagcccggg cccctccccg gcgggtgcgg cggcggcggc ccgcgctccg acagtccgcg     60

cggccgggtc ctgcgcccgg ggcgaccccg gcgccccgcc ccgccgccgc ctgacttctc    120

ggcgcccgag gtcgcgcgcg cggaggcggg ggcggcccgg gatctccaag cgccgccgcg    180

ccctcctccc gcccgccctc cgcccgcccg ctcggcggcg gcggcggcgg cggaggaggc    240

ggagaaggct ggcaggcggc ggccgggaga gcgagcgcgg cggccggacc ggggccatgg    300

cgcccgcgca gcgcccgctg ctcccgctgc tgctcctgct gttaccgctg ccgccgccgc    360

ccttcgcgcg cgccgaggac gccgcccgcg ccaactcgga ccgctacgcc gtctactgga    420

accgcagcaa ccccaggttc cacgcaggcg cgggggacga cggcgggggc tacacggtgg    480

aggtgagcat caatgactac ctggacatct actgcccgca ctatggggcg ccgctgccgc    540

cggccgagcg catggagcac tacgtgctgt acatggtcaa cggcgagggc cacgcctcct    600

gcgaccaccg ccagcgcggc ttcaagcgct gggagtgcaa ccggcccgcg gcgcccgggg    660

ggccgctcaa gttctcggag aagttccagc tcttcacgcc cttctccctg ggcttcgagt    720

tccggcccgg ccacgagtat tactacatct ctgccacgcc tcccaatgct gtggaccggc    780

cctgcctgcg actgaaggtg tacgtgcggc cgaccaacga gaccctgtac gaggctcctg    840

agcccatctt caccagcaat aactcgtgta gcagcccggg cggctgccgc ctcttcctca    900

gcaccatccc cgtgctctgg accctcctgg gttcctagtc ccagccccgc aggacgccga    960

ccctgcctgg acggccccgc ctggaccgcc tgacctcggc cctccggacc cggctgcggc   1020

ccccgcctcc gagaccaaat agagacgctg cttctccctc gcctggtgcc gcccccgccg   1080

ggcaggggcc atccacccgc cccaggacca gccctcaggg aggggaaacg gccgagagcc   1140
```

```
ccccccccgga ggcccgaggg gccggggtgt ggatgcggac cgtggccagg ccatctcctc   1200

tggggcgtcg gagaacccgg gaacctcttg gcgatttttt tttttttttt tttttttttt   1260

ttttttttta gtgtattttt cgtggttgga tcaaaaagac ttgagttttt aatttaattt   1320

attccctgcc gttgtagcgg ggcggggtcc ctgtgccctg gcctggggga ggggaacgcg   1380

gaacatgggg tcgggaacac agccgctccc ctctgctctg caccccactc gtgggggaac   1440

acagccgctc ccctctgctc tgcaccccac tcgtggggga acacagccgc tcccctctgc   1500

tctgcacccc actcgtgggg gaacacagcc gctcccctct gctctgcacc ccactcgtgg   1560

gggaacacag ctgcagccca ccgcggaccc ccctggtgct ccaggttggg tgagtctgag   1620

ccggaagggg tacgtggtgg gcgcccctca ttgtggctgg ggagacctca taccccatcg   1680

cccacccccg tcctcctggt catttcctcc cagacactgt tttgccccag cgcccttcgg   1740

aatcacagtc ccgccgtgtc ttagaaactg ctttggccga tgcaaacagc cccctacccg   1800

tccccctcgc ctcacacggt ccctctccga ggccgagaag accttctgtt cctgtaaata   1860

cagccagcaa gtgcaaactg tgatttttatt ttccacgtat tcctgaggac ggactggacc   1920

gtctatgttt tttcagccct tcataggggg tcttttattt tggtgggggg gtggggtgga   1980

cttttagagt agaagctgca cttggcaata agctcgtgtc gtctgtcaga gcccctctct   2040

caactctgtg acctgataat gtttctaaga aaaagaaaaa aaggacaaaa gggagggaac   2100

cactaccaaa aaaaaaaaaa gaaactcctc cccgaagaca ctttaatgaa ggaaacaaca   2160

catttatacg gatttcatat ttctacccgc ctttcctgac tctgtgtttt atatatatta   2220

tatataaata tatattgtgt acggccgccg gccggcggct cgaggcacgc ccggtggtgg   2280

ggggtgggca gagggctttt gtagggggtc ggcggggcgg gccgcgttgc caggcctgga   2340

gctggcgacc gggcctccct cttcccgtca caatcaactt tggattctgt attttttttat   2400

aataaaatga gcataaacct caaa                                         2424
```

<210> SEQ ID NO 11
<211> LENGTH: 1225
<212> TYPE: DNA
<213> ORGANISM: Artificial Sequence
<220> FEATURE:
<223> OTHER INFORMATION: Synthetic polynucleotide

<400> SEQUENCE: 11

```
gagtgcgggg ctcagtcggg gggcggcggc ggcggcggct ccggggatgg cggcggctcc     60

gctgctgctg ctgctgctgc tcgtgcccgt gccgctgctg ccgctgctgg cccaggggcc    120

tgggggcgca ctgggaaacc ggcatgcggt atactggaac agctccaatc agcacctgcg    180

gcgagagggc tacaccgtgc aggtgaacgt gaacgactat ctggatattt actgtccgca    240

ctacaacagc tcagggcctg gcggcggggc ggagcagtac gtgctgtaca tggtgaacct    300

gagcggctac cgcacctgca acgccagcca aggctccaag cgctgggaat gcaaccggca    360

gcacgcctcg cacagcccca tcaagttctc cgagaagttc cagcgttaca gcgccttctc    420

gctgggctat gaattccatg ccggccaaga atactactac atctccacgc ccactcacaa    480

cctgcactgg aagtgtctga ggatgaaggt gttcgtctgc tgcgcctcca catcgcactc    540

cggggagaag ccggtcccca ctctccccca gttcaccatg ggccccaatg tgaagatcaa    600

cgtgttggaa gactttgagg gagagaatcc ccaggtgccc aagcttgaga agagcatcag    660

tgggaccagc cccaagcggg aacacctgcc tctggccgtg ggcatcgcct tcttcctcat    720

gacgctcttg gcctcctagc tctgcccctt cctatgacag agagaggtgg gaagggctga    780
```

```
gaaggagcag ggagcttgct gtggggccta catccttctt cccatggttg ggagcggggt    840

ctgcactgta catctctctg ggcctgccct ctttgcccac acactctcta ggacaggcac    900

cgtagtggat caggcacagg gacagccaca ggtcccaggt ggcctgtggc tttggtaatg    960

tttggtacca aacctggggg ctataaaggc agtgctcagg actccctggc ccctggtacc   1020

tttccctgac ccttggtgcc ctccctcttt gtcccccaag aggcaaatat gccccagaga   1080

gaacaaacga agcatgggag gtgccccctg tcctctcctc tggggcagaa catggggagg   1140

ggactaggtg ggtgaggggt ggagcctcag gctgcccctc cccctgttta cagcaataag   1200

catgtcctct ccctccactc ccaca                                         1225
```

<210> SEQ ID NO 12
<211> LENGTH: 2153
<212> TYPE: DNA
<213> ORGANISM: Artificial Sequence
<220> FEATURE:
<223> OTHER INFORMATION: Synthetic polynucleotide

<400> SEQUENCE: 12

```
ggggagcccc cgcgcccggg gaacccggga gagcgccttg cgcagtgcac cgctcgggcc     60

tctgccccgc gccgccgtcg ccgccgccgc cgccgccgcc gccgccgcct ggtttctcgg    120

cgcccgcggt ctacggcggg ggccgcgcgc agaggcgggg cggcagatct ccaagcgcgc    180

gcggcgctcc gcccgctcgg cggcggaggc ggaggcggag acggcggggc caggcggcgg    240

ctggagagcg agggagcgag cgcggcggca gcaccggggc catggcgccc gcgcagcgcc    300

cgctgctgcc gctgctgctg ctgctgctgc cgctgcgtgc gcgcaacgag gacccggccc    360

gggccaacgc tgaccgatac gcagtctact ggaaccgtag caaccccagg tttcaggtga    420

gcgctgtggg tgatggcggc ggctataccg tggaggtgag catcaacgac tacctggata    480

tctactgccc acactacggg gcgccgctgc ccccggctga gcgcatggag cggtacatcc    540

tgtacatggt gaatggtgag ggccacgcct cctgtgacca ccggcagcga ggcttcaagc    600

gctgggaatg caaccggccc gcagcgcccg gggacccct caagttctca gagaagttcc     660

aactcttcac cccctttcc ctgggctttg agttccggcc tggccacgaa tactactaca     720

tctctgccac acctcccaac ctcgtggacc gaccctgcct gcgactcaag gtttatgtgc    780

gtccaaccaa tgagaccctg tatgaggctc cagagcccat cttcaccagt aacagctcct    840

gcagcggcct gggtggctgc cacctcttcc tcaccaccgt ccctgtgctg tggtcccttc    900

tgggctccta gtgtcaggcc ggagaacacc agccccacct ggaccccgtg acctttgccc    960

tctgacctgc cacggccacc tccgagacaa aatccttgct gcttctcttt catggtgctg   1020

tcccgccgga ggaggccatc catccgtccc tgggatgcaa catggggtcc caatgcctga   1080

ggagaagacc ccccccaag gctgactcgc tttcaccagg gccaccaggg ccatccagtg    1140

ttgtttaatt acagtcggaa agacttaagg tttttctttt aatttaattt attccctgac   1200

attgctggtg acactgggaa gggaacaagc cacagggatg aggtgaagcc atctctgtcc   1260

ttcctggaat accggagatc caggggcctc cagctgctcc tttcttctgt gtcctgttat   1320

ttgggtccca gatggagccc accgcggact tgccttgcat tcctcaggcc aggcaagcct   1380

gagccagaaa gggcgcacgg tgccagcccc tctcggggac tctgggggtg ccatccccca   1440

ctcttcttcc agccactctc gggccccact cccacatcat ctcagaaacc cttcagccct   1500

cgcaactcgc ccctccgggc ccccccacca ggcacaacca tccccggggc cagccgggac   1560
```

```
gttgtcggtt tatttctgta aatagaaacc agcaagtgta tactgtgatt tattttaatg   1620

tattcttaag gacagaatgg aaattcttta aaaaaaattt tttttccgac cttcaattca   1680

aggggtcatt tattttggtg gggggagtgg ggtggacttt ttaggataga agcaacactt   1740

tgcaataaac tcattttttt ttgttccgtt ggagccctcc cccttgatca tgtgacctag   1800

taatgtttat aacaaaaaaa attaaaaaaa aaaaaagaag aaggaaaaaa aatacaggac   1860

tggaaaggaa ggggagctac ctaccaaaaa tacagcaggc aaaggactga gtgaagctgg   1920

ccacaccaca cgtttatacg gatttcggat ttctacccac gtttcctcac tctgttttct   1980

atatattcta tataaatata tattgtggat ggccgccatg gcgagtggtg gctggggctt   2040

ttctaggggc gggggacggg tggcccggcc ccctcatcac aatcagcttt gaagtctgta   2100

ttttttata ataaaatgga caaactgtta aaaaaaaaaa aaaaaaaaaa aaa          2153
```

<210> SEQ ID NO 13
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 13

```
Gln Gly Pro Gly Gly Ala Leu Gly Asn Arg His Ala Val Tyr Trp Asn
1               5                   10                  15

Ser Ser Asn Gln His Leu Arg Arg Glu Gly Tyr Thr Val Gln Val Asn
            20                  25                  30

Val Asn Asp Tyr Leu Asp Ile Tyr Cys Pro His Tyr Asn Ser Ser Gly
        35                  40                  45

Pro Gly Gly Gly Ala Glu Gln Tyr Val Leu Tyr Met Val Asn Leu Ser
    50                  55                  60

Gly Tyr Arg Thr Cys Asn Ala Ser Gln Gly Ser Lys Arg Trp Glu Cys
65                  70                  75                  80

Asn Arg Gln His Ala Ser His Ser Pro Ile Lys Phe Ser Glu Lys Phe
                85                  90                  95

Gln Arg Tyr Ser Ala Phe Ser Leu Gly Tyr Glu Phe His Ala Gly Gln
            100                 105                 110

Glu Tyr Tyr Tyr Ile Ser Thr Pro Thr His Asn Leu His Trp Lys Cys
        115                 120                 125

Leu Arg Met Lys Val Phe Val Cys Cys Ala Ser Thr Ser His Ser Gly
    130                 135                 140

Glu Lys Pro Val Pro Thr Leu Pro Gln Phe Thr Met Gly Pro Asn Val
145                 150                 155                 160

Lys Ile Asn Val Leu Glu Asp Phe Glu Gly Glu Asn Pro Gln Val Pro
                165                 170                 175

Lys Leu Glu Lys Ser Ile Ser Gly Ile Glu Gly Arg Met Asp Pro Ala
            180                 185                 190

Lys Thr Thr Ala Pro Ser Val Tyr Pro Leu Ala Pro Val Cys Gly Asp
        195                 200                 205

Thr Thr Gly Ser Ser Val Thr Leu Gly Cys Leu Val Lys Gly Tyr Phe
    210                 215                 220

Pro Glu Pro Val Thr Leu Thr Trp Asn Ser Gly Ser Leu Ser Ser Gly
225                 230                 235                 240

Val His Thr Phe Pro Ala Val Leu Gln Ser Asp Leu Tyr Thr Leu Ser
                245                 250                 255

Ser Ser Val Thr Val Thr Ser Ser Thr Trp Pro Ser Gln Ser Ile Thr
```

```
            260                 265                 270

Cys Asn Val Ala His Pro Ala Ser Ser Thr Lys Val Asp Lys Lys Ile
        275                 280                 285

Glu Pro Arg Gly Pro Thr Ile Lys Pro Cys Pro Pro Cys Lys Cys Pro
    290                 295                 300

Ala Pro Asn Leu Leu Gly Gly Pro Ser Val Phe Ile Phe Pro Pro Lys
305                 310                 315                 320

Ile Lys Asp Val Leu Met Ile Ser Leu Ser Pro Ile Val Thr Cys Val
                325                 330                 335

Val Val Asp Val Ser Glu Asp Asp Pro Asp Val Gln Ile Ser Trp Phe
            340                 345                 350

Val Asn Asn Val Glu Val His Thr Ala Gln Thr Gln Thr His Arg Glu
        355                 360                 365

Asp Tyr Asn Ser Thr Leu Arg Val Val Ser Ala Leu Pro Ile Gln His
    370                 375                 380

Gln Asp Trp Met Ser Gly Lys Glu Phe Lys Cys Lys Val Asn Asn Lys
385                 390                 395                 400

Asp Leu Pro Ala Pro Ile Glu Arg Thr Ile Ser Lys Pro Lys Gly Ser
                405                 410                 415

Val Arg Ala Pro Gln Val Tyr Val Leu Pro Pro Pro Glu Glu Glu Met
            420                 425                 430

Thr Lys Lys Gln Val Thr Leu Thr Cys Met Val Thr Asp Phe Met Pro
        435                 440                 445

Glu Asp Ile Tyr Val Glu Trp Thr Asn Asn Gly Lys Thr Glu Leu Asn
    450                 455                 460

Tyr Lys Asn Thr Glu Pro Val Leu Asp Ser Asp Gly Ser Tyr Phe Met
465                 470                 475                 480

Tyr Ser Lys Leu Arg Val Glu Lys Lys Asn Trp Val Glu Arg Asn Ser
                485                 490                 495

Tyr Ser Cys Ser Val Val His Glu Gly Leu His Asn His His Thr Thr
            500                 505                 510

Lys Ser Phe Ser Arg Thr Pro Gly Lys
        515                 520


<210> SEQ ID NO 14
<211> LENGTH: 521
<212> TYPE: PRT
<213> ORGANISM: Artificial Sequence
<220> FEATURE:
<223> OTHER INFORMATION: Synthetic polypeptide

<400> SEQUENCE: 14

Asn Arg His Ala Val Tyr Trp Asn Ser Ser Asn Gln His Leu Arg Arg
1               5                   10                  15

Glu Gly Tyr Thr Val Gln Val Asn Val Asn Asp Tyr Leu Asp Ile Tyr
            20                  25                  30

Cys Pro His Tyr Asn Ser Ser Gly Ala Gly Pro Gly Pro Gly Gly Gly
        35                  40                  45

Ala Glu Gln Tyr Val Leu Tyr Met Val Ser Arg Asn Gly Tyr Arg Thr
    50                  55                  60

Cys Asn Ala Ser Gln Gly Phe Lys Arg Trp Glu Cys Asn Arg Pro His
65                  70                  75                  80

Ala Pro His Ser Pro Ile Lys Phe Ser Glu Lys Phe Gln Arg Tyr Ser
                85                  90                  95

Ala Phe Ser Leu Gly Tyr Glu Phe His Ala Gly His Glu Tyr Tyr Tyr
```

-continued

```
            100                 105                 110

Ile Ser Thr Pro Thr His Asn Leu His Trp Lys Cys Leu Arg Met Lys
        115                 120                 125

Val Phe Val Cys Cys Ala Ser Thr Ser His Ser Gly Glu Lys Pro Val
    130                 135                 140

Pro Thr Leu Pro Gln Phe Thr Met Gly Pro Asn Val Lys Ile Asn Val
145                 150                 155                 160

Leu Glu Asp Phe Glu Gly Glu Asn Pro Gln Val Pro Lys Leu Glu Lys
                165                 170                 175

Ser Ile Ser Ile Glu Gly Arg Met Asp Ala Ser Thr Lys Gly Pro Ser
            180                 185                 190

Val Phe Pro Leu Ala Pro Ser Ser Lys Ser Thr Ser Gly Gly Thr Ala
        195                 200                 205

Ala Leu Gly Cys Leu Val Lys Asp Tyr Phe Pro Glu Pro Val Thr Val
    210                 215                 220

Ser Trp Asn Ser Gly Ala Leu Thr Ser Gly Val His Thr Phe Pro Ala
225                 230                 235                 240

Val Leu Gln Ser Ser Gly Leu Tyr Ser Leu Ser Ser Val Val Thr Val
                245                 250                 255

Pro Ser Ser Ser Leu Gly Thr Gln Thr Tyr Ile Cys Asn Val Asn His
            260                 265                 270

Lys Pro Ser Asn Thr Lys Val Asp Lys Lys Val Glu Pro Lys Ser Cys
        275                 280                 285

Asp Lys Thr His Thr Cys Pro Pro Cys Pro Ala Pro Glu Leu Leu Gly
    290                 295                 300

Gly Pro Ser Val Phe Leu Phe Pro Pro Lys Pro Lys Asp Thr Leu Met
305                 310                 315                 320

Ile Ser Arg Thr Pro Glu Val Thr Cys Val Val Val Asp Val Ser His
                325                 330                 335

Glu Asp Pro Glu Val Lys Phe Asn Trp Tyr Val Asp Gly Val Glu Val
            340                 345                 350

His Asn Ala Lys Thr Lys Pro Arg Glu Glu Gln Tyr Asn Ser Thr Tyr
        355                 360                 365

Arg Val Val Ser Val Leu Thr Val Leu His Gln Asp Trp Leu Asn Gly
    370                 375                 380

Lys Glu Tyr Lys Cys Lys Val Ser Asn Lys Ala Leu Pro Ala Pro Ile
385                 390                 395                 400

Glu Lys Thr Ile Ser Lys Ala Lys Gly Gln Pro Arg Glu Pro Gln Val
                405                 410                 415

Tyr Thr Leu Pro Pro Ser Arg Asp Glu Leu Thr Lys Asn Gln Val Ser
            420                 425                 430

Leu Thr Cys Leu Val Lys Gly Phe Tyr Pro Ser Asp Ile Ala Val Glu
        435                 440                 445

Trp Glu Ser Asn Gly Gln Pro Glu Asn Asn Tyr Lys Thr Thr Pro Pro
    450                 455                 460

Val Leu Asp Ser Asp Gly Ser Phe Phe Leu Tyr Ser Lys Leu Thr Val
465                 470                 475                 480

Asp Lys Ser Arg Trp Gln Gln Gly Asn Val Phe Ser Cys Ser Val Met
                485                 490                 495

His Glu Ala Leu His Asn His Tyr Thr Gln Lys Ser Leu Ser Leu Ser
            500                 505                 510

Pro Gly Lys His His His His His His
        515                 520
```

<210> SEQ ID NO 15
<211> LENGTH: 211
<212> TYPE: PRT
<213> ORGANISM: Artificial Sequence
<220> FEATURE:
<223> OTHER INFORMATION: Synthetic polypeptide

<400> SEQUENCE: 15

```
Met Ala Ala Ala Pro Leu Leu Leu Leu Leu Leu Leu Val Pro Val Pro
1               5                   10                  15

Leu Leu Pro Leu Leu Ala Gln Gly Pro Gly Gly Ala Leu Gly Asn Arg
            20                  25                  30

His Ala Val Tyr Trp Asn Ser Ser Asn Gln His Leu Arg Arg Glu Gly
        35                  40                  45

Tyr Thr Val Gln Val Asn Val Asn Asp Tyr Leu Asp Ile Tyr Cys Pro
    50                  55                  60

His Tyr Asn Ser Ser Gly Pro Gly Gly Gly Ala Glu Gln Tyr Val Leu
65                  70                  75                  80

Tyr Met Val Asn Leu Ser Gly Tyr Arg Thr Cys Asn Ala Ser Gln Gly
                85                  90                  95

Ser Lys Arg Trp Glu Cys Asn Arg Gln His Ala Ser His Ser Pro Ile
            100                 105                 110

Lys Phe Ser Glu Lys Phe Gln Arg Tyr Ser Ala Phe Ser Leu Gly Tyr
        115                 120                 125

Glu Phe His Ala Gly Gln Glu Tyr Tyr Tyr Ile Ser Thr Pro Thr His
    130                 135                 140

Asn Leu His Trp Lys Cys Leu Arg Met Lys Val Phe Val Cys Cys Ala
145                 150                 155                 160

Ser Thr Ser His Ser Gly Glu Lys Pro Val Pro Thr Leu Pro Gln Phe
                165                 170                 175

Thr Met Gly Pro Asn Val Lys Ile Asn Val Leu Glu Asp Phe Glu Gly
            180                 185                 190

Glu Asn Pro Gln Val Pro Lys Leu Glu Lys Ser Ile Ser His His His
        195                 200                 205

His His His
    210
```

<210> SEQ ID NO 16
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 16

```
Met Ala Ala Ala Pro Leu Leu Leu Leu Leu Leu Leu Val Pro Val Pro
1               5                   10                  15

Leu Leu Pro Leu Leu Ala Gln Gly Pro Gly Gly Ala Leu Gly Asn Arg
            20                  25                  30

His Ala Val Tyr Trp Asn Ser Ser Asn Gln His Leu Arg Arg Glu Gly
        35                  40                  45

Tyr Thr Val Gln Val Asn Val Asn Asp Tyr Leu Asp Ile Tyr Cys Pro
    50                  55                  60

His Tyr Asn Ser Ser Gly Val Gly Pro Gly Ala Gly Pro Gly Pro Gly
65                  70                  75                  80

Gly Gly Ala Glu Gln Tyr Val Leu Tyr Met Val Ser Arg Asn Gly Tyr
```

```
                85                  90                  95

Arg Thr Cys Asn Ala Ser Gln Gly Phe Lys Arg Trp Glu Cys Asn Arg
            100                 105                 110

Pro His Ala Pro His Ser Pro Ile Lys Phe Ser Glu Lys Phe Gln Arg
        115                 120                 125

Tyr Ser Ala Phe Ser Leu Gly Tyr Glu Phe His Ala Gly His Glu Tyr
    130                 135                 140

Tyr Tyr Ile Ser Thr Pro Thr His Asn Leu His Trp Lys Cys Leu Arg
145                 150                 155                 160

Met Lys Val Phe Val Cys Cys Ala Ser Thr Ser His Ser Gly Glu Lys
                165                 170                 175

Pro Val Pro Thr Leu Pro Gln Phe Thr Met Gly Pro Asn Val Lys Ile
            180                 185                 190

Asn Val Leu Glu Asp Phe Glu Gly Glu Asn Pro Gln Val Pro Lys Leu
        195                 200                 205

Glu Lys Ser Ile Ser His His His His His His
    210                 215


<210> SEQ ID NO 17
<211> LENGTH: 190
<212> TYPE: PRT
<213> ORGANISM: Artificial Sequence
<220> FEATURE:
<223> OTHER INFORMATION: Synthetic polypeptide

<400> SEQUENCE: 17

Met Ala Pro Ala Gln Arg Pro Leu Leu Pro Leu Leu Leu Leu Leu Leu
1               5                   10                  15

Pro Leu Arg Ala Arg Asn Glu Asp Pro Ala Arg Ala Asn Ala Asp Arg
            20                  25                  30

Tyr Ala Val Tyr Trp Asn Arg Ser Asn Pro Arg Phe Gln Val Ser Ala
        35                  40                  45

Val Gly Asp Gly Gly Gly Tyr Thr Val Glu Val Ser Ile Asn Asp Tyr
    50                  55                  60

Leu Asp Ile Tyr Cys Pro His Tyr Gly Ala Pro Leu Pro Pro Ala Glu
65                  70                  75                  80

Arg Met Glu Arg Tyr Ile Leu Tyr Met Val Asn Gly Glu Gly His Ala
                85                  90                  95

Ser Cys Asp His Arg Gln Arg Gly Phe Lys Arg Trp Glu Cys Asn Arg
            100                 105                 110

Pro Ala Ala Pro Gly Gly Pro Leu Lys Phe Ser Glu Lys Phe Gln Leu
        115                 120                 125

Phe Thr Pro Phe Ser Leu Gly Phe Glu Phe Arg Pro Gly His Glu Tyr
    130                 135                 140

Tyr Tyr Ile Ser Ala Thr Pro Pro Asn Leu Val Asp Arg Pro Cys Leu
145                 150                 155                 160

Arg Leu Lys Val Tyr Val Arg Pro Thr Asn Glu Thr Leu Tyr Glu Ala
                165                 170                 175

Pro Glu Pro Ile Phe Thr Ser Asn His His His His His His
            180                 185                 190


<210> SEQ ID NO 18
<211> LENGTH: 22
<212> TYPE: PRT
<213> ORGANISM: Mus musculus

<400> SEQUENCE: 18
```

-continued

```
Met Ala Ala Ala Pro Leu Leu Leu Leu Leu Leu Leu Val Pro Val Pro
1               5                   10                  15

Leu Leu Pro Leu Leu Ala
            20


<210> SEQ ID NO 19
<211> LENGTH: 22
<212> TYPE: PRT
<213> ORGANISM: Homo sapiens

<400> SEQUENCE: 19

Met Ala Ala Ala Pro Leu Leu Leu Leu Leu Leu Leu Val Pro Val Pro
1               5                   10                  15

Leu Leu Pro Leu Leu Ala
            20


<210> SEQ ID NO 20
<211> LENGTH: 20
<212> TYPE: PRT
<213> ORGANISM: Mus musculus

<400> SEQUENCE: 20

Met Ala Pro Ala Gln Arg Pro Leu Leu Pro Leu Leu Leu Leu Leu Leu
1               5                   10                  15

Pro Leu Arg Ala
            20
```